(12) United States Patent
Tata et al.

(10) Patent No.: US 6,420,376 B1
(45) Date of Patent: Jul. 16, 2002

(54) AMIDO SPIROPIPERIDINES PROMOTE THE RELEASE OF GROWTH HORMONE

(75) Inventors: James R. Tata; Arthur A. Patchett, both of Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/614,193

(22) Filed: Jul. 10, 2000

Related U.S. Application Data

(60) Provisional application No. 60/143,571, filed on Jul. 13, 1999.

(51) Int. Cl.$^7$ ................. C07D 401/06; A61K 31/438
(52) U.S. Cl. ........................... 514/278; 546/17
(58) Field of Search ................. 546/17; 514/278

(56) References Cited

U.S. PATENT DOCUMENTS 5,578,593 A * 11/1996 Chen et al.

\* cited by examiner

*Primary Examiner*—Alan L. Rotman
*Assistant Examiner*—Rita Desai
(74) *Attorney, Agent, or Firm*—J. Eric Thies; Melvin Winokur

(57) ABSTRACT

The present invention is directed to certain spiropiperidines of the general structural formula:

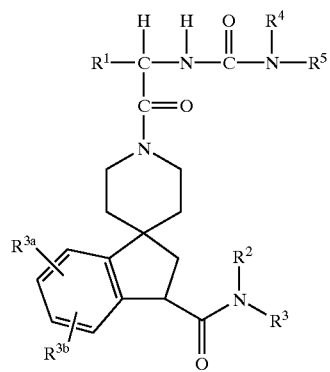

wherein $R^1$, $R^2$, $R^3$, $R^{3a}$, $R^{3b}$, $R^4$ and $R^5$ are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such compounds as the active ingredient thereof are also disclosed.

7 Claims, No Drawings

AMIDO SPIROPIPERIDINES PROMOTE THE RELEASE OF GROWTH HORMONE

CROSS REFERENCE TO RELATED APPLICATIONS

This application claims priority under 35 U.S.C. 119(e) from Provisional Application No. 60/143,571, filed Jul. 13, 1999.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues are disclosed in e.g., U.S. Pat. Nos. 5,206,235, 5,283,241, 5,284,841, 5,310,737, 5,317,017, 5,374,721, 5,430,144, 5,434,261, 5,438,136, 5,494,919, 5,494,920, 5,492,916, 5,536,716 and 5,578,593. Other growth hormone secretagogues are disclosed e.g., in PCT Patent Publications WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, and WO 96/02530. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain spiropiperidines which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the piperidine compounds. It is a further object of this invention to describe procedures for the preparation of such compounds. A still further object is to describe the use of such compounds to increase the secretion of growth hormone in humans and animals. A still further object of this invention is to describe compositions containing the piperidine compounds for the use of treating humans and animals so as to increase the level of growth hormone secretions. Further objects will become apparent from a reading of the following description.

DESCRIPTION OF THE INVENTION

The novel spiropiperidines of the instant invention are described by structural Formula I:

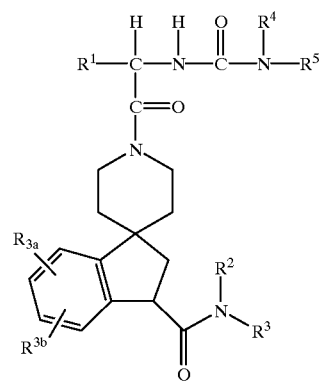

Formula I wherein:

$R^1$ is selected from the group consisting of:

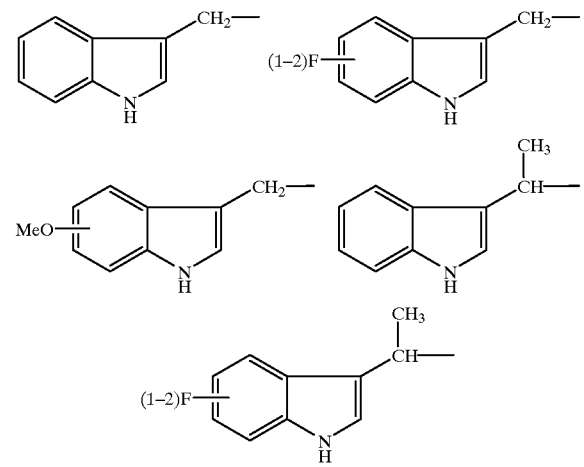

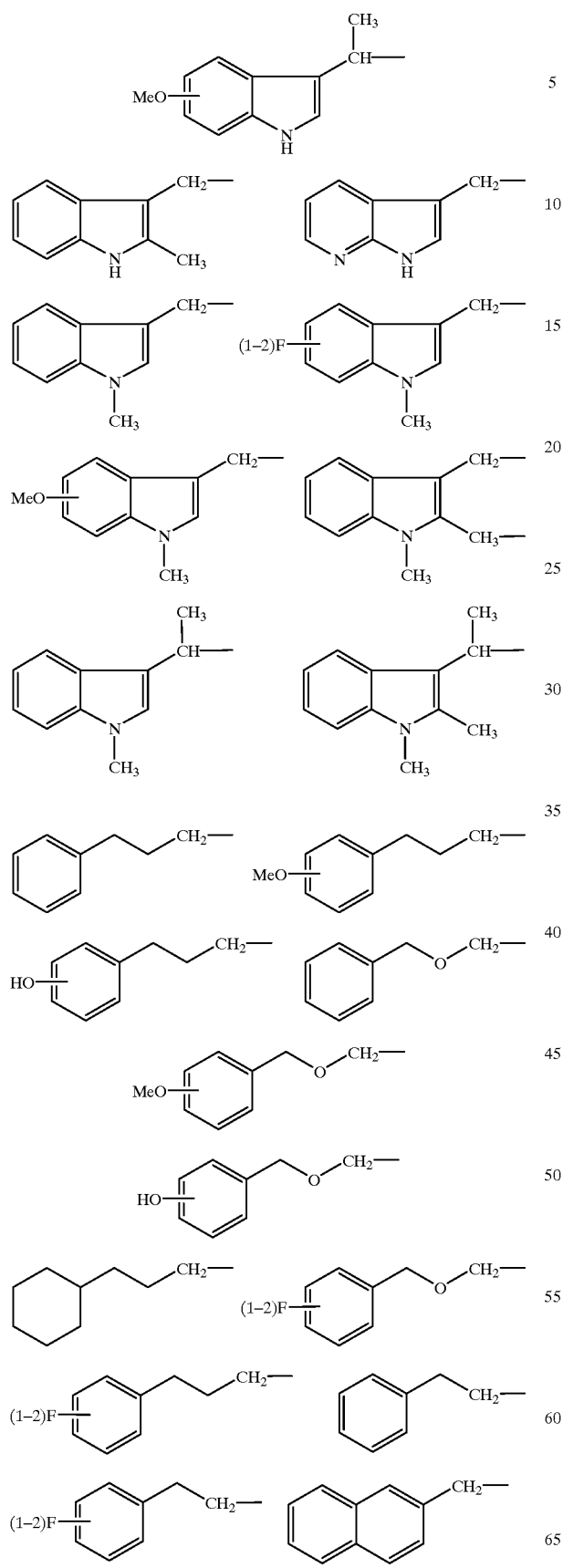
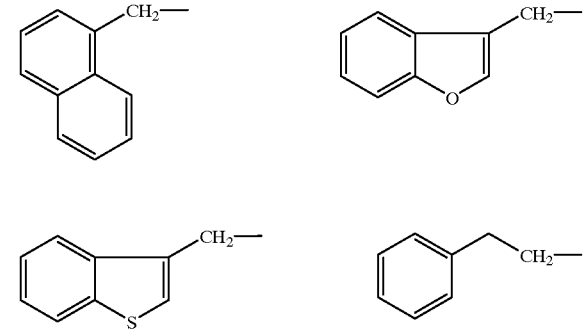
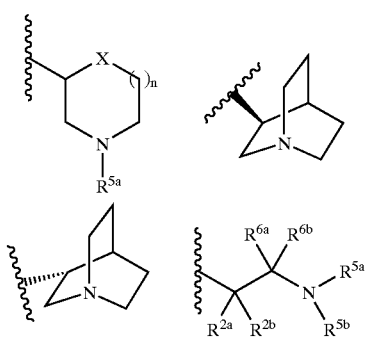

or their regioisomers where not specified;

R$^2$ and R$^3$ are independently selected from the group consisting of:
hydrogen, —C$_1$–C$_6$ alkyl, —C$_3$–C$_7$ cycloalkyl, and —CH$_2$-phenyl, wherein the alkyl, the cycloalkyl and the phenyl are unsubstituted or substituted with —OR$^{2a}$, —C(O)OR$^{2a}$, —C(O)N(R$^{2a}$)(R$^{2b}$), halogen, —C$_1$–C$_4$ alkyl, —S(O)$_n$R$^{2a}$, —NHS(O)2 (R$^{2a}$), and wherein R$^2$ and R$^2$ are optionally joined to form a C$_4$–C$_5$ cyclic ring being selected from the group consisting of pyrrolidine, piperidine, piperazine, morpholine, and thiomorpholine;

R$^{2a}$ and R$^{2b}$ are independently selected from: hydrogen and C$_1$–C$_6$ alkyl;

R$^{3a}$ and R$^{3b}$ are independently selected from: hydrogen, —C$_1$–C$_6$ alkyl, —OR$^2$, and halogen;

R$^4$ is selected from: hydrogen, C$_1$–C$_6$ alkyl, and substituted C$_1$–C$_6$ alkyl where the substituents on alkyl are selected from halo, —OR$^2$, phenyl, C$_1$–C$_6$ alkoxycarbonyl, —S(O)$_n$R$^{2a}$, and —NHS(O)$_n$(R$^{2a}$);

R$^5$ is selected from:
hydrogen,
C$_1$–C$_6$ alkyl,
substituted C$_1$–C$_6$ alkyl where the substituents on alkyl are selected from halo, —OR$^2$, phenyl, —S(O)$_n$R$^{2a}$, —NHS(O)$_n$(R$^{2a}$), R$^{5a}$ and R$^{5b}$ are independently selected from: hydrogen, C$_1$–C$_6$ alkyl, or substituted C$_1$–C$_6$ alkyl where the substituents are selected from: halo, —OR$^2$, C$_1$–C$_6$ alkoxy, phenyl, C$_1$–C$_6$ alkoxycarbonyl, —S(O)$_n$R$^{2a}$, —NHS(O)$_n$(R$^{2a}$);

R$^{6a}$ and R$^{6b}$ are independently selected from: hydrogen, C$_1$–C$_6$ alkyl, or trifluoromethyl;

X is selected from —CH$_2$—, —O— and —S—;
n is independently 0, 1 or 2;
and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halo" or "halogen" is intended to include any of the halogen atoms fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1$–$C_6$ alkyl, 1 to 3 of halogen, 1 to 2 of $OR_2$, methylenedioxy, —$S(O)_mR_2$, 1 to 2 of —$CF_3$, —$OCF_3$, nitro, —$N(R_2)C(O)(R_2)$, —$C(O)OR_2$, —$C(O)N(R_2)(R^2)$, -1H-tetrazol-5-yl, —$SO_2N(R_2)(R_2)$, —$N(R_2)SO_2$ phenyl, or —$N(R_2)SO_2R_2$, wherein $R_2$ is as defined herein.

Certain of the above defined terms may occur more than once in the above formula and upon such occurrence each term shall be defined independently of the other.

Preferred compounds of the instant invention include those of Formula I wherein:

$R^1$ is selected from the group consisting of:

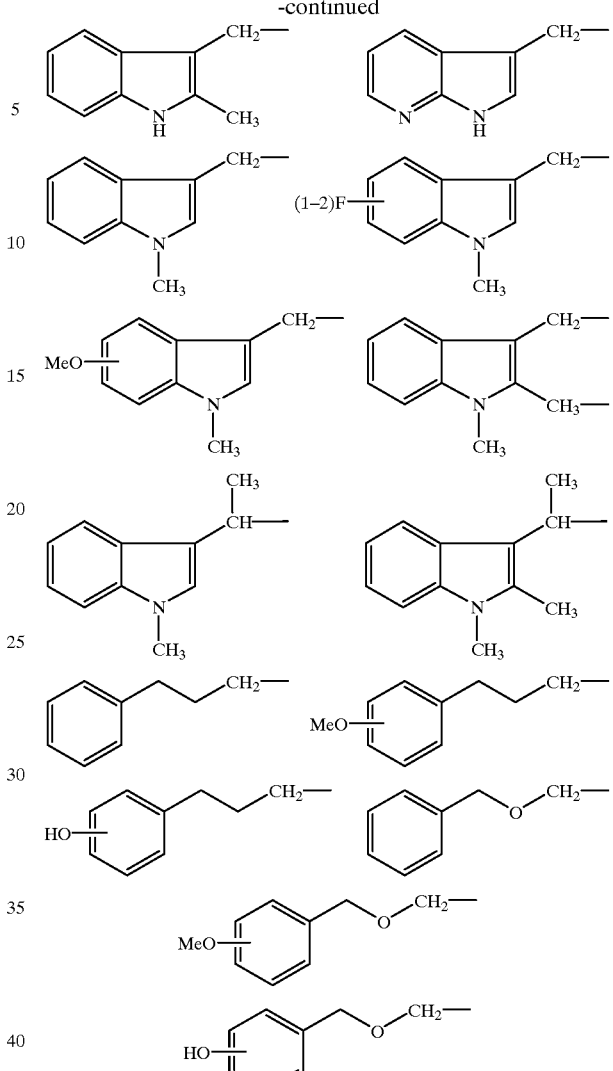
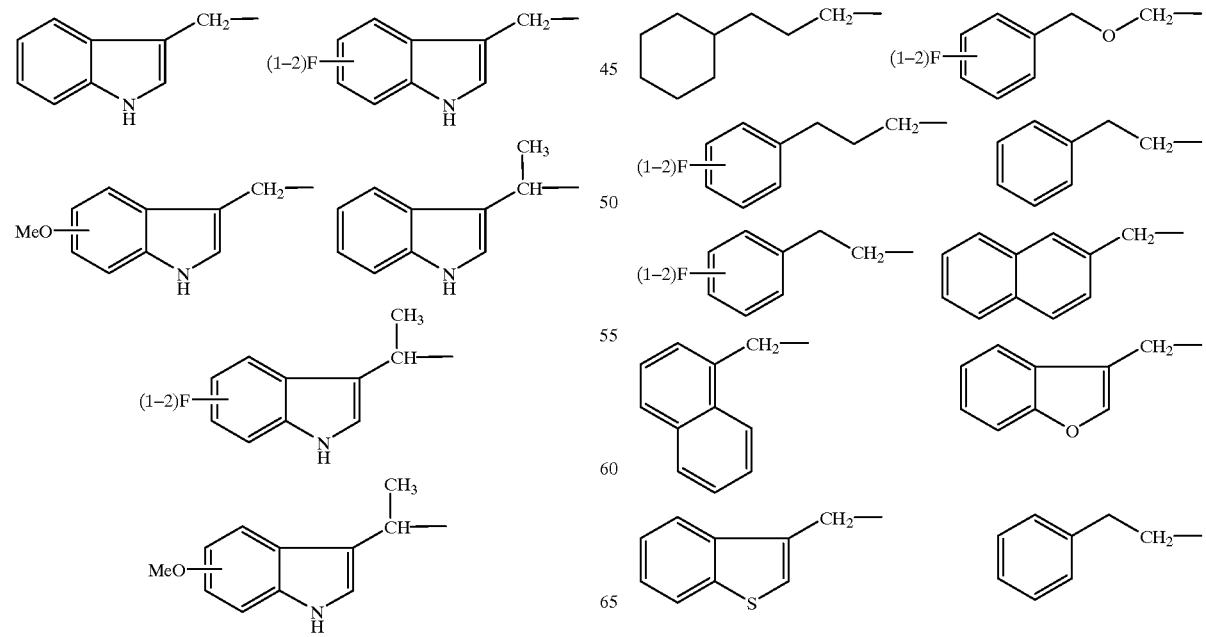

or their regioisomers where not specified;

$R^2$ and $R^3$ are independently selected from the group consisting of:
hydrogen, —$C_1$-$C_6$ alkyl, —$C_3$-$C_7$ cycloalkyl, and —$CH_2$-phenyl, wherein the alkyl, the cycloalkyl and the phenyl are unsubstituted or substituted with —$OR^{2a}$, —$C(O)OR^{2a}$, —$C(O)N(R^{2a})(R^{2b})$, halogen, —$C_1$-$C_4$ alkyl, —$S(O)_nR^{2a}$, —$NHS(O)_2(R^{2a})$, and wherein $R^2$ and $R^2$ are optionally joined to form a $C_4$-$C_5$ cyclic ring being selected from the group consisting of pyrrolidine, piperidine, piperazine, and morpholine;

$R^{2a}$ and $R^{2b}$ are independently selected from: hydrogen and $C_1$-$C_4$ alkyl;

$R^{3a}$ and $R^{3b}$ are independently selected from: hydrogen, —$C_1$-$C_6$ alkyl, —$OR^2$, and halogen;

$R^4$ is selected from: hydrogen, $C_1$-$C_6$ alkyl, and substituted $C_1$-$C_6$ alkyl where the substituents on alkyl are selected from halo, hydroxy, and —$S(O)_nR^{2a}$;

$R^5$ is selected from:
hydrogen,
$C_1$-$C_6$ alkyl,
substituted $C_1$-$C_6$ alkyl where the substituents on alkyl are selected from halo, hydroxy, phenyl, $S(O)_nR^{2a}$, —$NHS(O)_n(R^{2a})$,

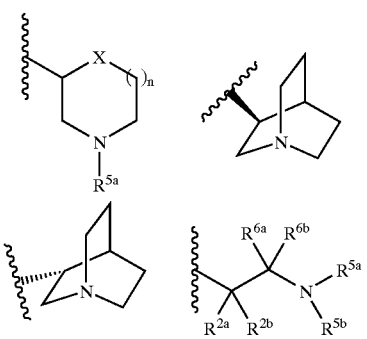

$R^{5a}$ and $R^{5b}$ are independently selected from: hydrogen, $C_1$-$C_6$ alkyl, or substituted $C_1$-$C_6$ alkyl where the substituents are selected from: halo, hydroxy, $C_{1-6}$ alkoxy, phenyl, —$S(O)_nR^{2a}$, and —$NHS(O)_n(R^{2a})$;

$R^{6a}$ and $R^{6b}$ are independently selected from: hydrogen, $C_1$-$C_6$ alkyl, or trifluoromethyl;

X is selected from —$CH_2$—, —O— and —S—;

n is independently 0, 1 or 2;

and pharmaceutically acceptable salts and individual diastereomers thereof.

More preferred compounds of the instant invention include those of Formula I wherein:

$R^1$ is selected from the group consisting of:

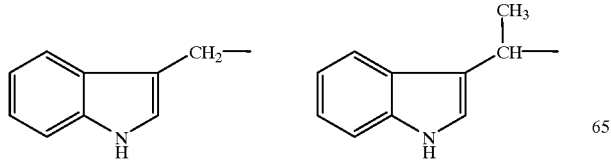

-continued

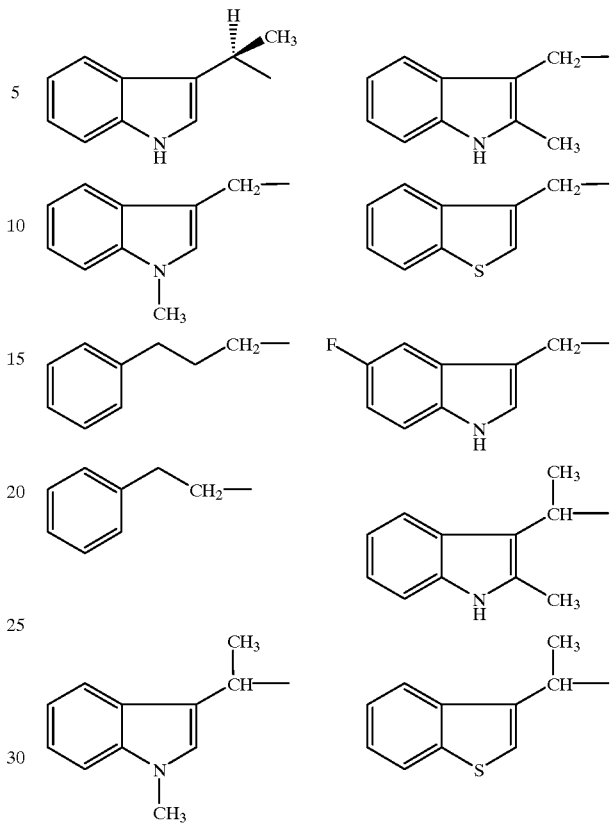

$R^2$ and $R^3$ are independently selected from the group consisting of:
hydrogen and —$C_1$-$C_6$ alkyl, wherein the alkyl is unsubstituted or substituted with —$OR^{2a}$, —$S(O)_2R^{2a}$, and —$NHS(O)_2CH_3$, and wherein $R^2$ and $R^2$ are optionally joined to form a 5- or 6-membered ring selected from the group consisting of pyrrolidine, piperidine, piperazine, and morpholine;

$R^{2a}$ and $R^{2b}$ are independently selected from: hydrogen and $C_1$-$C_4$ alkyl;

$R^{3a}$ and $R^{3b}$ are independently selected from: hydrogen and halogen;

$R^4$ is selected from: hydrogen or $C_1$-$C_4$ alkyl;

$R^5$ is selected from:
hydrogen,
$C_1$-$C_6$ alkyl,
substituted $C_1$-$C_6$ alkyl where the substituents on alkyl are selected from halo, hydroxy, phenyl, —$NHS(O)_2(R^{2a})$,

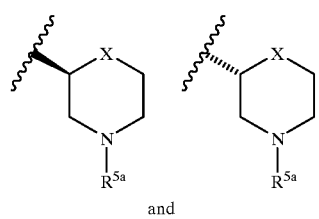

and

-continued

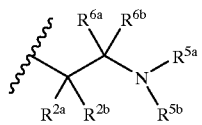

R$^{5a}$ and R$^{5b}$ are independently selected from: hydrogen, C$_1$–C$_6$ alkyl, or substituted C$_1$–C$_6$ alkyl where the substituents are selected from: halo, hydroxy, C$_1$–C$_6$ alkoxy, phenyl, —S(O)$_n$R$^{2a}$, and —NHS(O)$_n$(R$^{2a}$);

R$^{6a}$ and R$^{6b}$ are independently selected from: hydrogen, C$_1$–C$_6$ alkyl, or trifluoromethyl;

X is selected from —CH$_2$— and —O—;

n is 0, 1 or 2;

and pharmaceutically acceptable salts and individual diastereomers thereof.

Specific compounds within the instant invention include

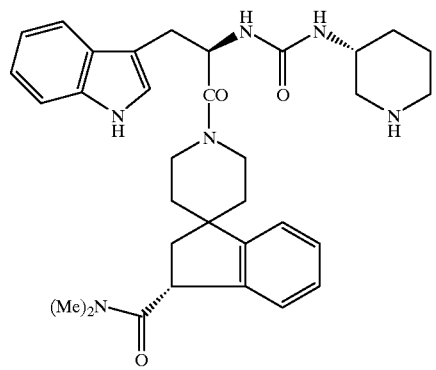

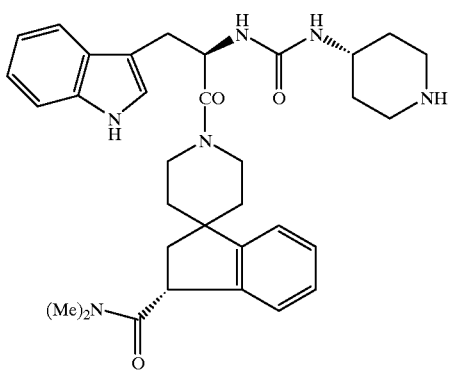

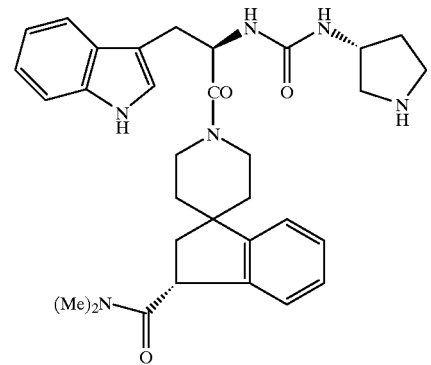

-continued

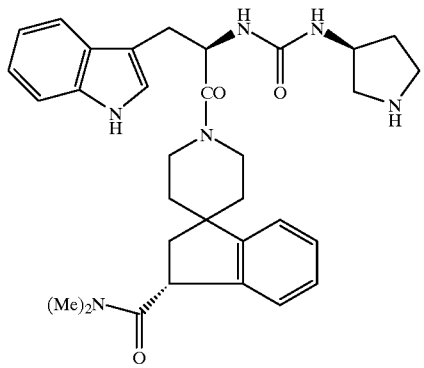

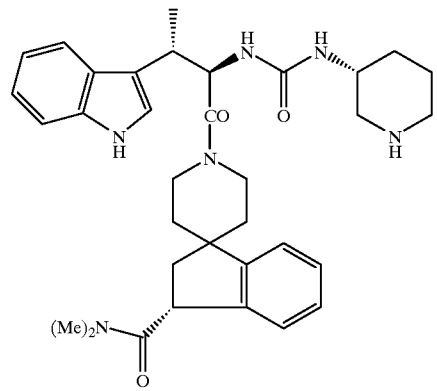

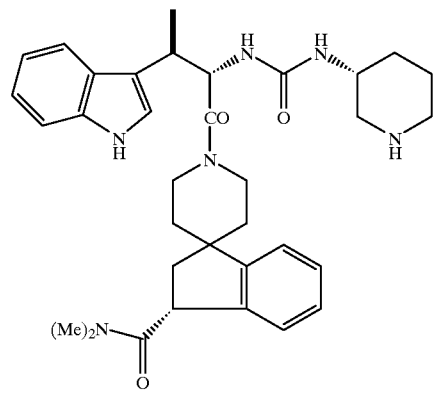

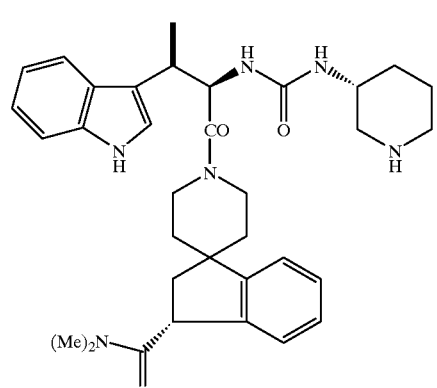

-continued
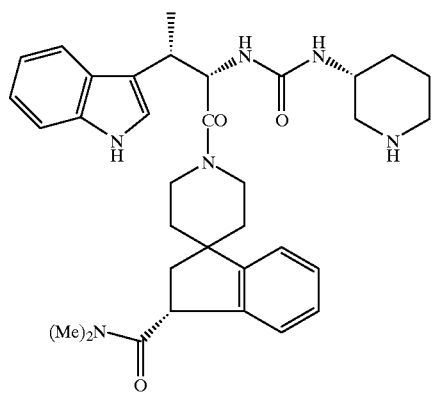
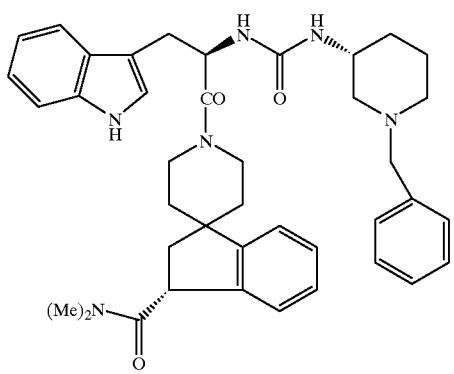
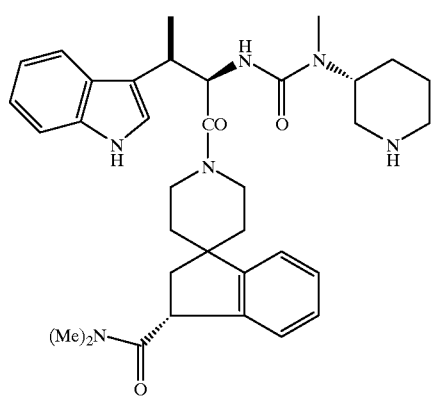
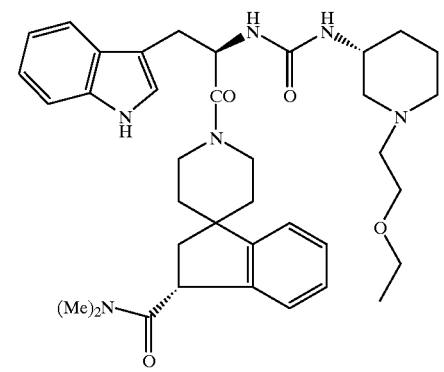
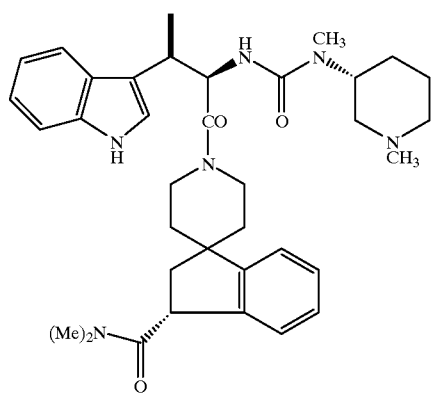
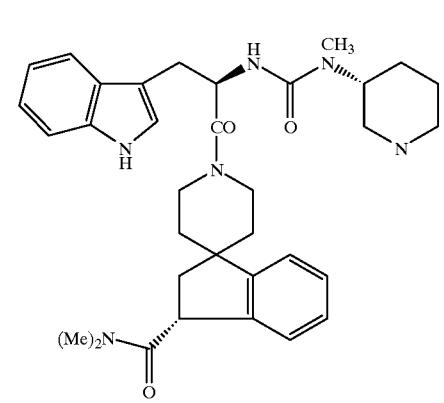
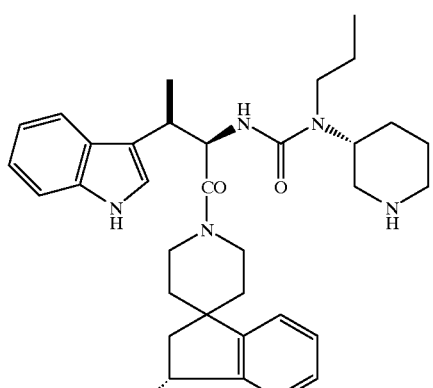
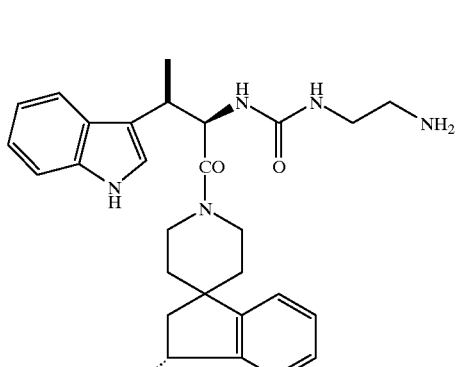

-continued
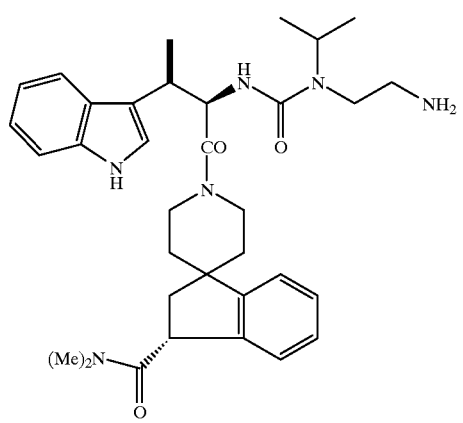
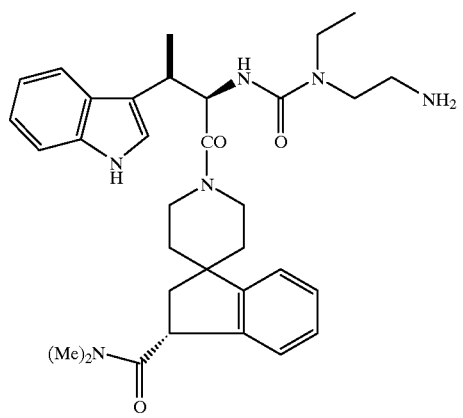
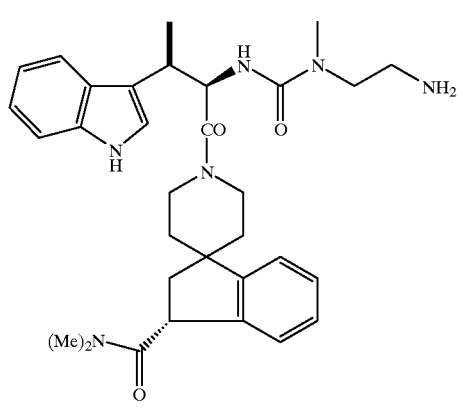
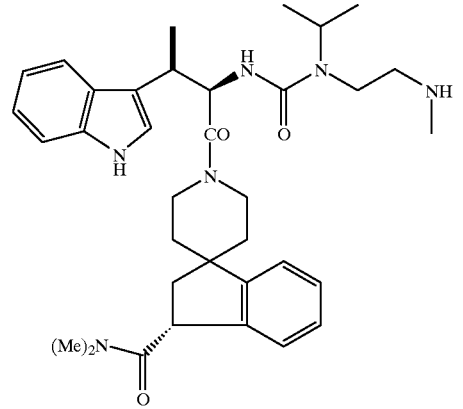
-continued
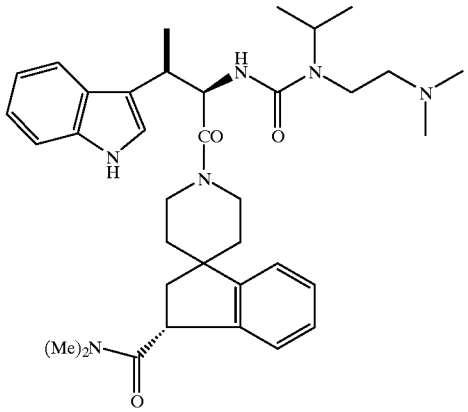
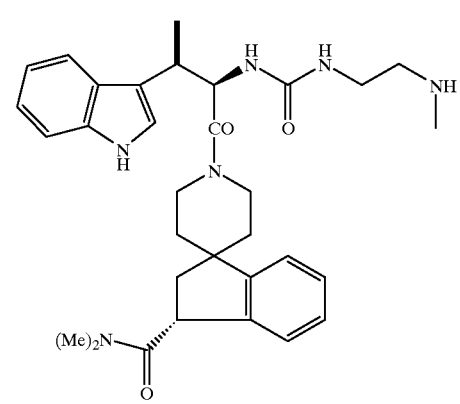
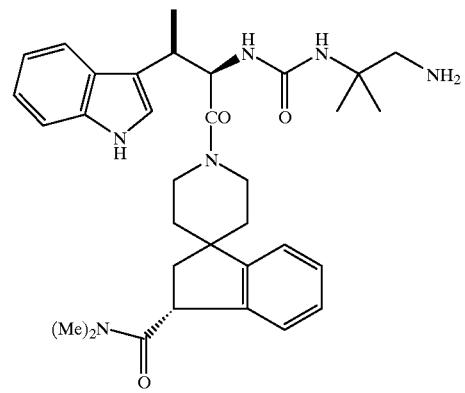
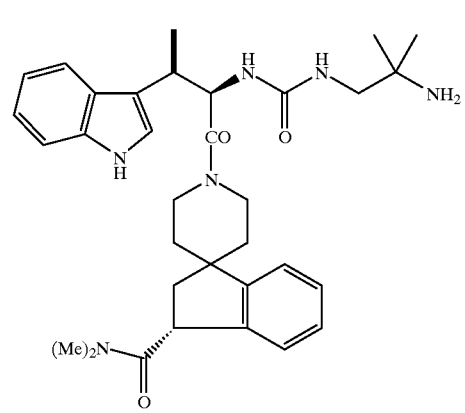

-continued
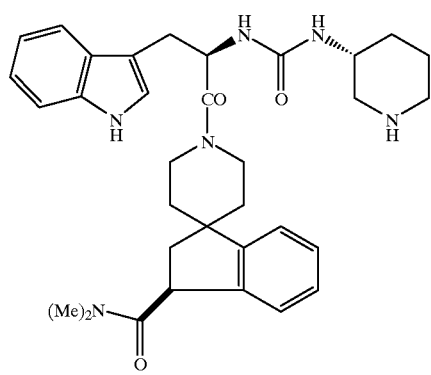
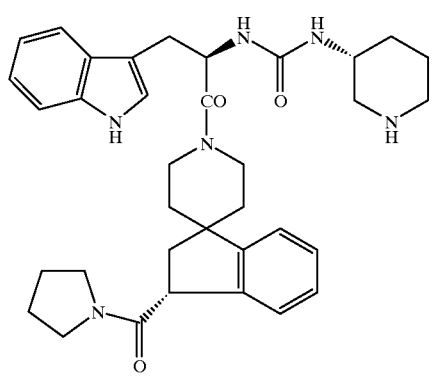
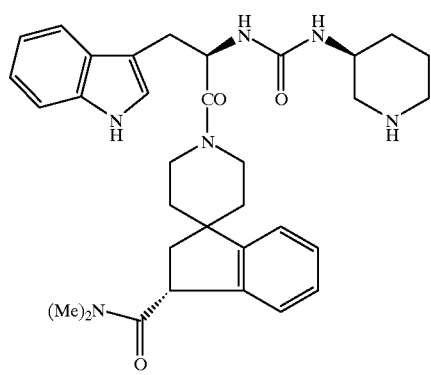
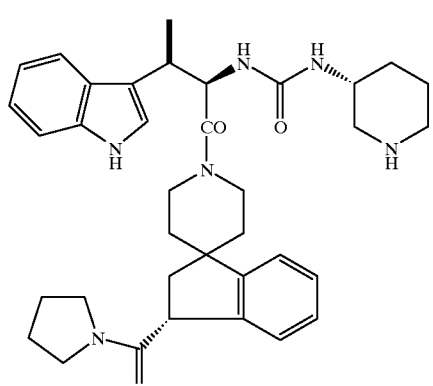
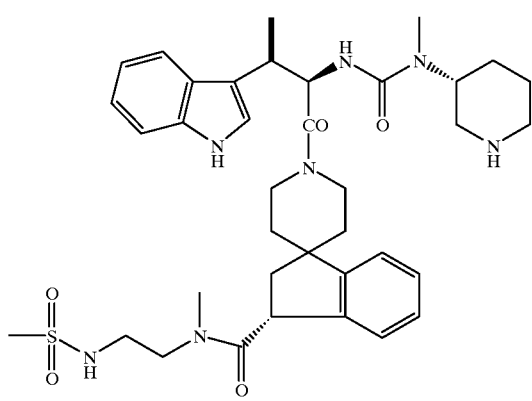
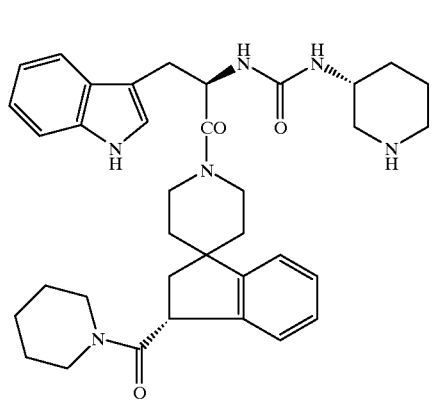
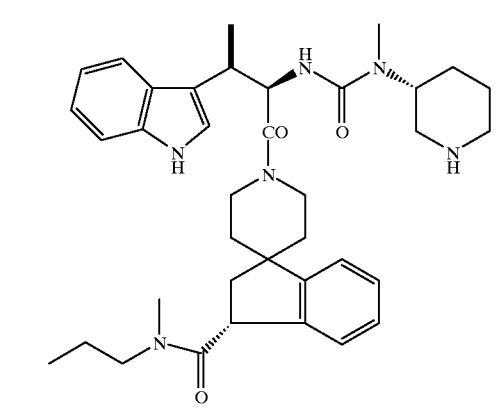
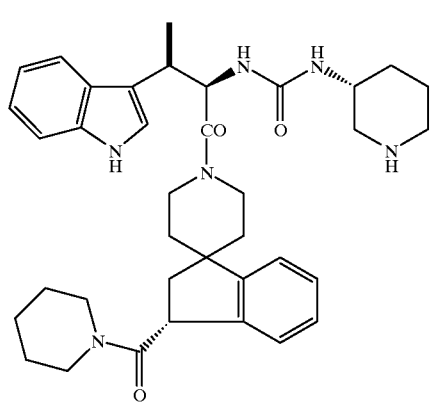

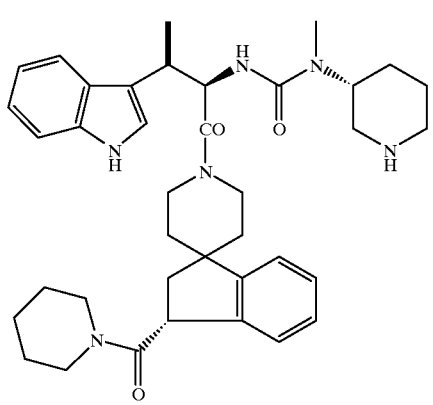
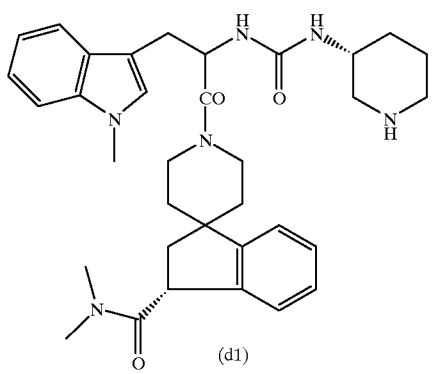
(d1)
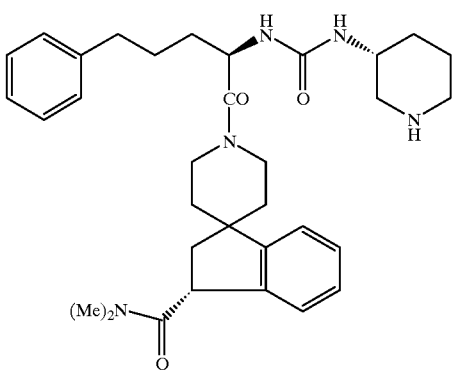
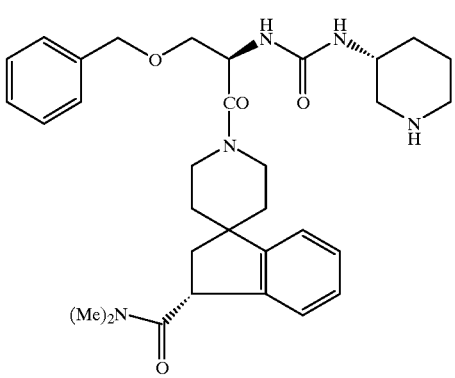
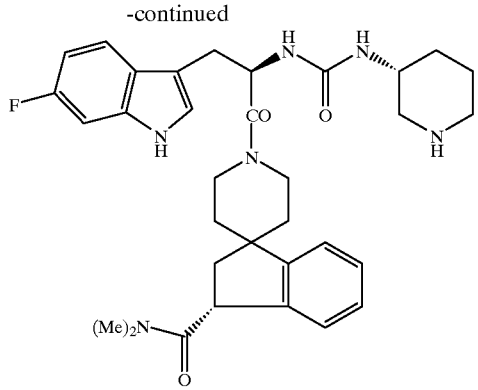
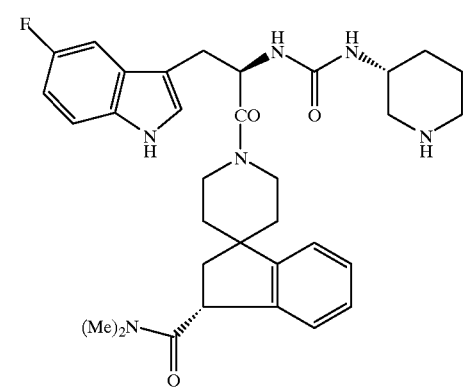
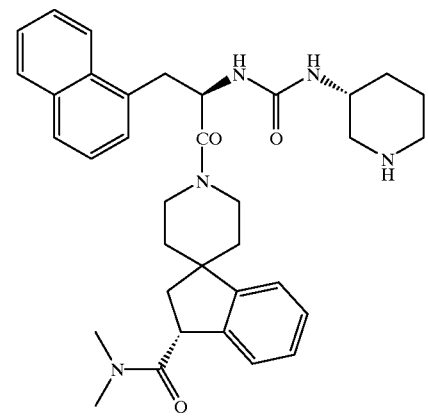
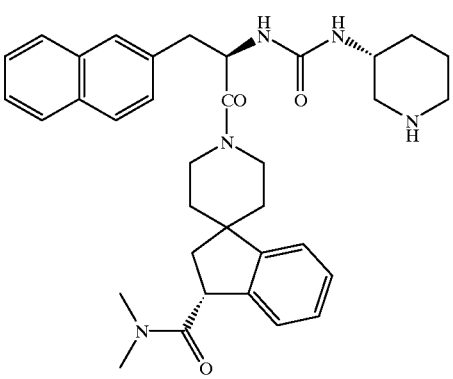

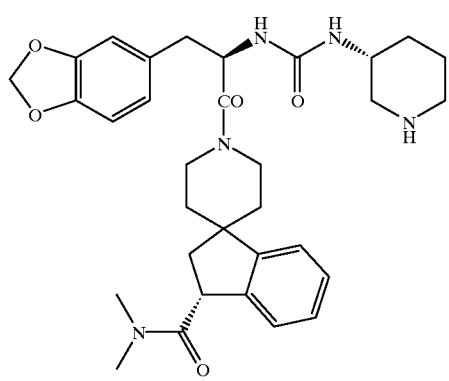
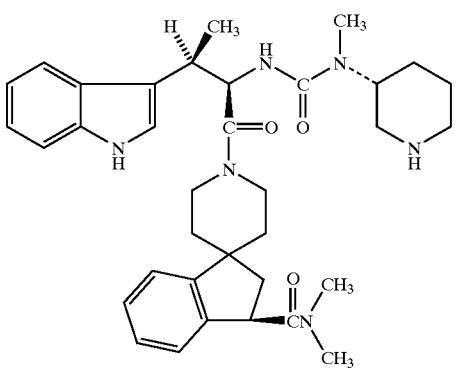
and pharmaceutically acceptable salts and individual diastereomers thereof where not otherwise specified.
Preferred specific compounds within the instant invention include
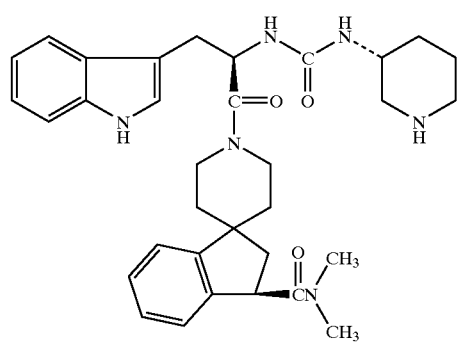
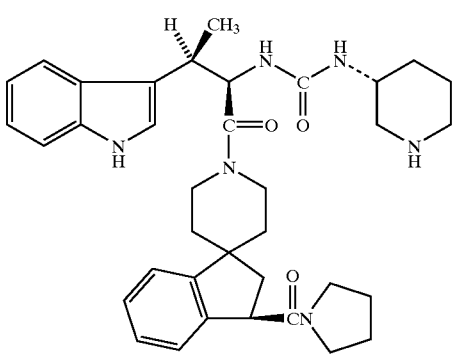
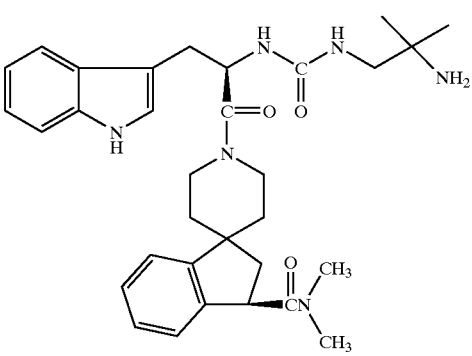
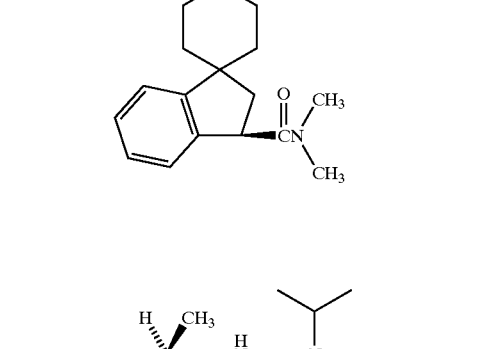
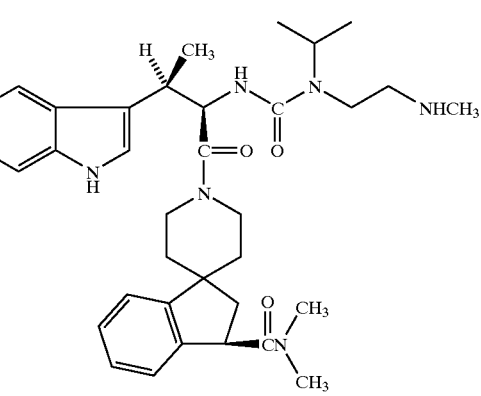

-continued

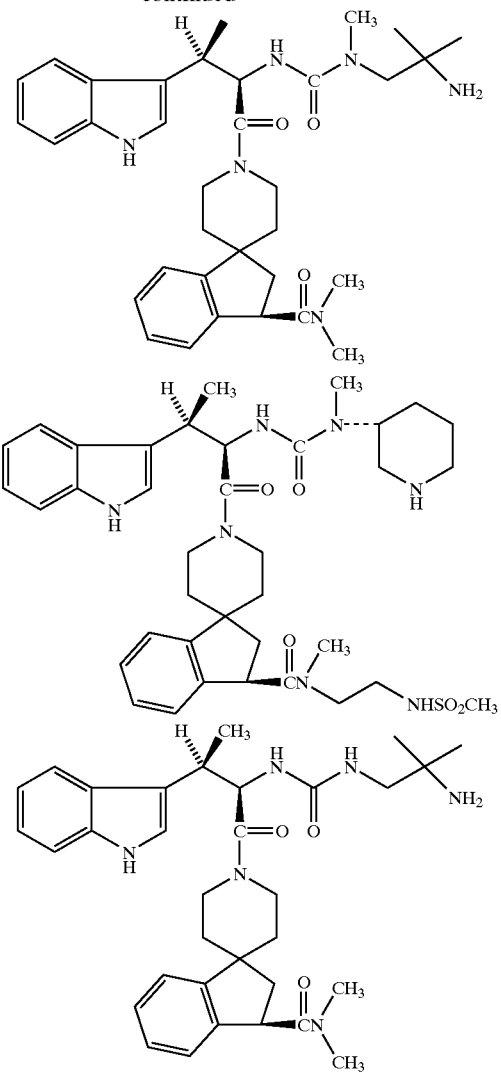

and pharmaceutically acceptable salts and individual diastereomers thereof where not otherwise specified.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris/dimethylamino)-phosphonium hexafluorophosphate |
| calc. | calculated |
| CBZ, Cbz | Benzyloxycarbonyl |
| DCC | Dicyclohexylcarbodiimide |
| DMF | N,N-dimethylformamide |
| DMAP | 4-Dimethylaminopyridine |
| EDC | 1-(3-dimethylaminopropyl)-3-ethylcarbodi-imide hydrochloride |
| EI-MS | Electron ion-mass spectroscopy |
| Et | ethyl |
| eq. | equivalent(s) |
| FAB-MS | Fast atom bombardment-mass spectroscopy |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

The compounds of the instant invention have at least two asymmetric centers. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric center which bears the X and Y groups, in most cases, both R- and S-configurations are consistent with useful levels of growth hormone secretagogue activity. In addition configurations of many of the most preferred compounds of this invention are:

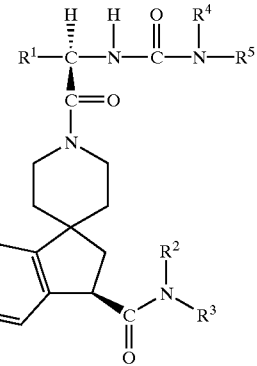

Formula I indicated. When diastereomers result in a synthetic process they are arbitrarily referred to as diastereomer 1 ($d_1$) and diastereomer 2 ($d_2$) in this invention and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion-can be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC were used extensively in the synthesis, and their removal conditions are known to those skilled in the art. For example, removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines, pyrrolidines, and hexahydro-1H-azepines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures includes crystallization, normal phase or reverse phase chromatography.

SCHEME 1

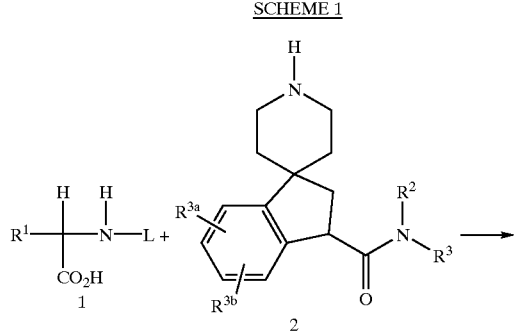

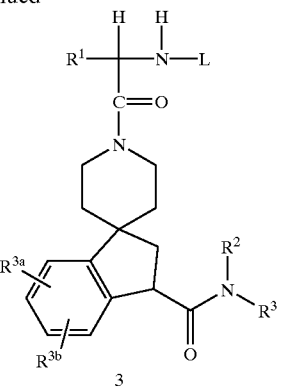

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

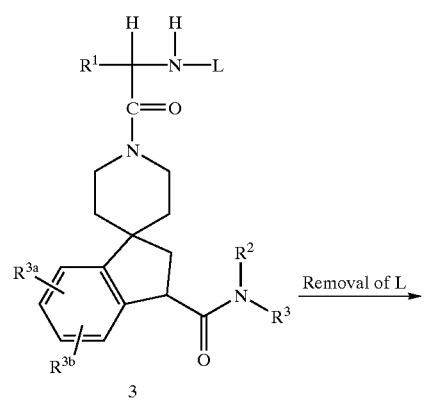

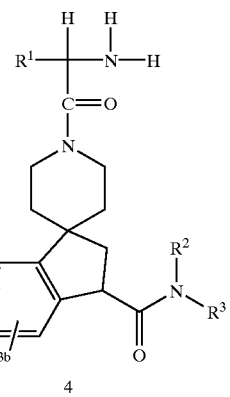

Conversion of 3 to intermediate 4 can be carried out as illustrated in Scheme 2 by removal of the protecting group L (CBZ, BOC, etc.)

SCHEME 3

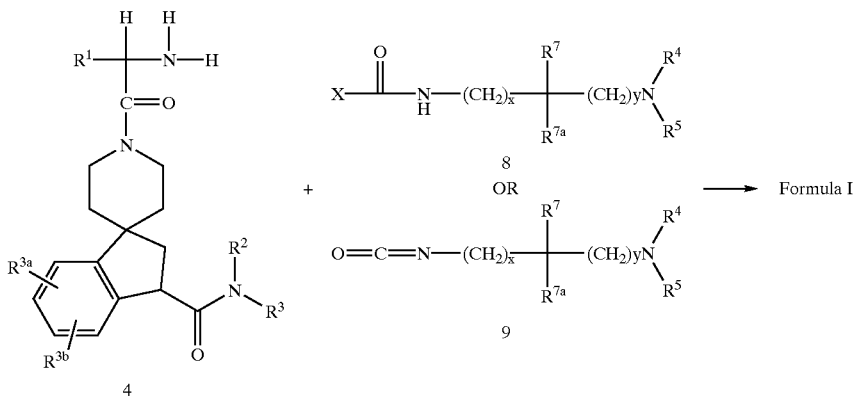

Compounds of Formula I may be prepared as shown in Scheme 3 by reacting 4 with reagents 8, wherein X is a good leaving group such as Cl, Br, I, or imidazole. Alternatively, 4 may be reacted with an isocyanate of Formula 9 in an inert solvent such as 1,2-dichloroethane to provide compounds of Formula I where Z is NH.

In cases where a sulfide is present in the molecule, it may be oxidized to a sulfoxide or to a sulfone with oxidizing agents such as sodium periodate, m-chloroperbenzoic acid or Oxone® in an solvent such as dichloromethane, alcohol or water or their mixtures.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "Synthesis of Optically Active α-Amino Acids" Pergamon Press: Oxford, 1989; Vol. 7). Several methods exist to resolve (DL)-

amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("Asymmetric Synthesis, Chiral Catalysis; Morrison, J. D., Ed; Academic Press: Orlando, Fla., 1985; Vol 5); and (6) enzymatic syntheses (*Angew. Chem. Int. Ed. Engl.* 1978, 17, 176).

SCHEME 4

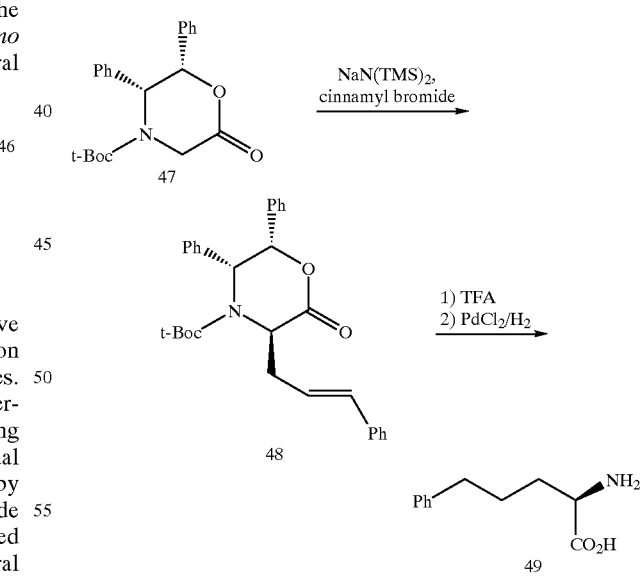

For example, alkylation of the enolate of diphenyloxazinone 47 (*J. Am. Chem. Soc.* 1991, 113, 9276) with cinnamyl bromide in the presence of sodium bis(trimethylsilyl)amide proceeds smoothly to afford 48 which is converted into the desired (D)-2-amino-5-phenylpentanoic acid 49 by removing the N-t-butyloxycarbonyl group with trifluoroacetic acid and hydrogenation over a $PdCl_2$ catalyst (Scheme 4).

SCHEME 5

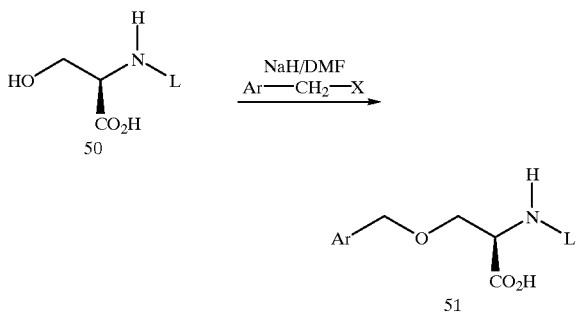

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 5.

The O-alkyl-(D)-serine derivatives may also be prepared using an alkylation protocol. Other methods that could be utilized to prepare (D)-serine derivatives of formula 51 include the acid catalyzed benzylation of carboxyl protected intermediates derived from 50 with reagents of formula $ArCH_2OC(=NH)CCl_3$ (O. Yonemitsu et al., Chem. Pharm. Bull. 1988, 36, 4244). Alternatively, alkylation of the chiral gylcine enolates (J. Am. Chem. Soc. 1991, 113, 9276; J. Org. Chem. 1989, 54, 3916) with $ArCH_2OCH_2X$ where X is a leaving group affords 51. In addition D,L-O-aryl(alkyl) serines may be prepared and resolved by methods described above.

The spiro indanes of formula 52 may be prepared by a number of methods, including the syntheses described below.

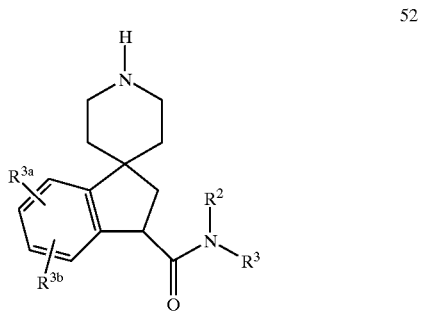

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

SCHEME 7

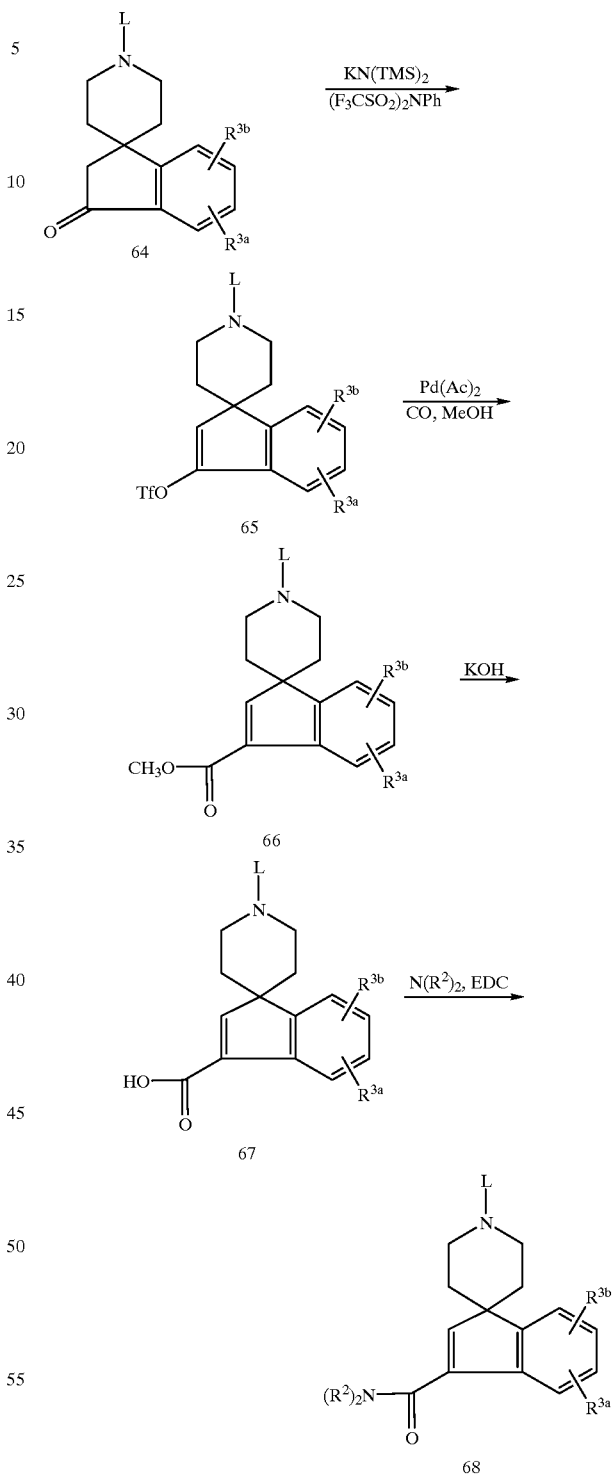

Homologation of the spiroindanone 64 provides easy access to spiroindanyl intermediates containing acid and ester groups. This chemistry is described in Scheme 26. Treatment of 64 with a base in an inert solvent such as THF followed by the addition of a triflating agent provides the enol triflate. Carboxylation of the enol triflate according to the procedure of Cacchi, S. Tetrahedron Letters, 1985, 1109–1112 provides the ester 66. The protecting group can then be removed as described above and the resulting amine can be incorporated into the subject compound via the chemistry depicted in the Schemes above.

Saponification of the ester of 66 provides an acid which can be conveniently derivatized as for example reaction with an amine in the presence of a coupling agent such as EDC gives amides which can then be incorporated into final compounds following the chemistry detailed in Schemes 1 and 8.

Hydrogenation of 66 using a palladium catalyst in an inert solvent provides the saturated compounds which can then either be derivatized as above or carried on to the final products via the chemistry described above. Reductive alkylation of the aldehyde with ammonium acetate and sodium cyanoborohydride affords an amino methyl analog. The aminomethyl analogs may then be further reacted to afford additional growth hormone secretagogues of the general formula I. Chiral acids are available by a variety of methods known to those skilled in the art including asymmetric catalytic hydrogenation and resolution of a pair of diastereomeric salts formed by reaction with a chiral amine such as D or L α-methylbenzylamine. The absolute stereochemistry can be determined in a number of ways including X-ray crystallography of a suitable crystalline derivative.

Chiral esters and acids are available by a variety of methods known to those skilled in the art including asymmetric catalytic hydrogenation, chomatographic resolution of a pair of diasteromers, and via crystallization of salts formed from chiral amines such as D or L-α-methylbenzylamine. The absolute stereochemistry can be determined in a number of ways including X-ray crystallography of a suitable crystalline derivative.

In some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay disclosed by Smith , et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

With respect to the compounds disclosed in U.S. Pat. No. 5,578,593, the present compounds exhibit unexpected properties, such as with respect to duration of action and/or metabolism, such as enhanced oral bioavailability.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, amino acids, estrogens, b-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox. or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or a-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrody-splasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; prevention and treatment of congestive heart failure; protection of cardiac structure and/or cardiac function; enhancing of recovery of a mammal following congestive heart failure; enhancing and/or improving sleep quality as well as the prevention and treatment of sleep disturbances; enhancing or improving sleep quality by increasing sleep efficiency and augmenting sleep maintenance; prevention and treatment of mood disorders, in particular depression; improving mood and subjective well being in a subject suffering from depression; reducing insulin resistance in humans and animals; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. In general, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T. Role of Bisphosphonates in Metabolic Bone Diseases. *Trends in Endocrinol. Metab.*, 4, 19–25(1993): Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, estrogen agonists/antagonists such as raloxifene and droloxifene, and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the disclosed invention.

EXAMPLE 1

N-[1(R,S)-[2,3-Dihydrospiro[1H-indene-1,4'-piperidin]-1'yl)carbonyl]-2-(indazol-3-yl)ethyl]-2-amino-2-methylpropanamide Hydrochloride Step A: [1(R,S)-[2,3-Dihydrospiro[1H-indene-1,4'piperidin]-1'yl)carbonyl]-2-(indazol-3-yl)ethyl]carbamic acid 1,1-dimethylethyl Ester To a mixture of 81 mg (0.265 mmol) of DL-2-amino-3-(3-indazole)propionic acid (J. Am. Chem. Soc., 1952,2009), 74 mg (0.33 mmol) of 3,4-dihydrospiro[1H-indene-1,4'-piperidine] hydrochloride [Chambers, et al, J. Med. Chem., 1992, 35, 2036] 45 mg (0.33 mmol) of HOBT, and 0.0 47 ml (0.33 mmol) of NMM in 1.0 ml of dichloromethane and 0.5 ml of DMF was added 63 mg (0.33 mmol) of EDC. The reaction mixture was strirred at room temperature over night and then poured into ethyl acetate, washed sequentually with saturated aqueous sodium bicarbonate and brine. The organic layer was dried over anhydrous sodium sulfate filtered and then concentrated. Purification by flash chromatography (silica gel, dichloromethane/ethyl acetate 3:1) gave 42 mg (34%) of the title compound. $^1$H NMR (200 MHz, CDCl$_3$,60/40 mixture of conformers): 7.80–7.65 (m, 1H), 7.50–7.31 (m, 2H), 7.22–7.04 (m, 5H), 6.81–6.60 (m, 1H), 5.88–5.72 (m, 1H), 5.26–5.08 (m, 1H), 4.58–4.38 (m, 1H), 3.92–3.70 (m, 1H), 3.51–3.38 (m, 2H), 3.10 (dt, 2/5H), 2.90–2.56 (m, 3 3/5H), 1.92–1.58 (m, 3H), 1.51–1.12 (m,1 2/5H), 0.78 (dt, 3/5H)

Step B: N-[1(R,S)-[2,3-Dihydrospiro[1H-indene-1,4'-piperidin]-1'yl)carbonyl]-2-(indazol-3-yl)ethyl]-2-[[1,1-dimethyl-ethyloxy)carbonyl]amino-2-methylpropanamide A solution of 37 mg (0.078 mmol) of the intermediate obtained in Step A in a 1:1 mixture of trifluroacetic acid and dichloromethane with 0.050 ml of anisole was stirred at room temperature for 1 hour. The solution was concentrated and azeotroped with toluene. The residue was dissolved in dichloromethane and cooled to 0° C. To this solution was added 18.5 mg (0.091 mmol) of Boc alpha methyl alanine, 12.2 mg (0.091 mmol) of HOBT, 0.013 ml (0.091 mmol) of NMM, and 17.3 mg (0.091 mmol) of EDC. The mixture was stirred at room temperature for 16 hours. The solution was then diluted with ethyl acetate and then washed with saturated sodium bicarbonate followed by brine. The organic layer was dried over sodium sulfate and concentrated. Purification by flash chromatography (silica gel, dichloromethane/ethyl acetate 2:1) gave 29 mg (69%) of the title compound. $^1$H NMR (400 MHz, CD$_3$OD, 2:1 mixture of conformers) 7.83 (d, 2/3H), 7.74 (d, 1/3H), 7.54–7.34 (m, 2H), 7.18–7.07 (m, 5 1/H), 6.60–6.51 (m, 2/3H), 5.48–5.40 (m, 1H), 4.33–4.28 (m, 2/3H), 3.89–3.81 (m, 1/3H), 3.79–3.71 (m, 2/3H), 3.10-(dt, 2/3H), 2.84 (t, 2/3H), 2.78 (t, 1H), 2.69–2.61 (m, 4/3), 1.92 t, 1H), 1.90–1.80 (m, 2/3H), 1.67 (dt, 1/3H), 1.44 (s, 8H), 1.38 (s, 4H), 1.29 (s, 2H), 1.24 (s, 1H), 1.30–1.18 (m, 2/3H), 1.10–1.09 (m, 4/3H), 0.41 (dt, 2/3H).

Step C: N-[1(R,S)-[2,3-Dihydrospiro[1H-indene-1,4'-piperidin]-1'yl)-carbonyl]-2-(indazol-3-yl)ethyl]-2-amino-2-methylpropanamide Hydrochloride A solution of 1.3 N HCl/methanol and 26 mg (0.046 mmol) of the intermediate obtained from Step B was stirred at room temperature for 3 hours and then concentrated. Purification by flash chromatography (silica gel, dichoromethane/methanol/ammonium hydroxide 94:5:1) gave 18.3 mg (85%) of the free amine. The free amine was dissolved in 0.5 ml of 1.3 N HCl/methanol and then concentrated to provide the title compound. $^1$H NMR (400 MHz CD$_3$OD, 60/40 mixture of rotatomers): 7.78 (t, 1H), 7.63–7.51 (m, 2H), 7.25 (t, 1H), 7.17–7.04 (m, 4 2/5H), 6.65

(d, 3/5H), 5.48–5.35 (m, 1H), 4.42 (d, 2/5H), 4.33 (d, 3/5H), 3.91–3.81 (m, 1H), 3.65–3.41 (m, 2H), 3.16 (t, 3/5H), 2.90 (t, 2/5H), 2.88 (t, 1H), 2.72 (t, 1H), 2.77–2.68 (m, 1H), 2.02–1.95 (m, 4H), 1.81 (dt, 2/5H), 1.68 (dt, 2/5H), 1.58 (s, 3H), 1.49 s, 2H), 1.39 (s, 1H), 1.30–1.23 (m, 2H), 1.05 (dt, 3/5H), 0.73 (dt, 3/5H). FAB-MS: m/e 460 (m+1).

EXAMPLE 2

N-[1(R,S)-[(2,3-Dihydro-3-oxospiro [1H-indene-1, 4'-piperidin]1'-yl)-carbonyl]-2-(indol-3-yl)ethyl]-2-amino-2-methylpropanamide Hydrochloride Step A: 1'-(t-Butyloxycarbonyl)-3,4-dihydro-3-oxospiro [1H-indene-1,4'-piperidine]

To a solution of 661 mg (2.31 mmol) of 1'-(t-butyloxycarbonyl)spiro[1H-indene-1,4'-piperidine] [prepared by the method of Chambers, et al, J. Med. Chem., 1992, 35, 2036] in 5.0 ml of THF was added 5.8 ml (1.0 M THF, 2.9 mmol) of 9-BBN. The reaction mixture was heated at 70° C. until TLC analysis indicated that the starting material was consumed. The solution was concentrated and the residue was dissolved in dichloromethane. The solution was cooled to 0° C. and 4.1 g (19.2 mmol) of PCC was added slowly over 15 minutes. The reaction mixture was warmed to room temperature and then to reflux for 30 minutes The solution was then diluted with ether and filtered through a pad of a mixture of celite and florisil. Purification by flash chromotgraphy (silica gel, hexane/ethyl acetate, 4:1) gave 326 mg (47%) of the title compound. $^1$H NMR (200 MHz, CDCl$_3$): 7.75–7.60 (m, 2H), 7.50–7.44 (m, 2H), 4.30–4.15 (m, 2H), 2.85 (dt, 2H), 2.63 (s, 2H), 1.98 (dt, 2H), 1.53–1.40 (m, 2H), 1.49 (s, 9H).

Step B: Spiro[1H-indene-1,4'-piperidin]-3(2H)-one Trifluoro-acetamide

A solution of the intermediate from Step A in a 1:1:0.5 mixture of trifluoroacetic acid, dichloromethane and anisole was stirred for 1 hour and then concentrated and azeotroped from toluene to give the title compound. $^1$H NMR (200 MHz, CDCl$_3$): 7.81–7.70 (m, 1H), 7.62–7.45 (m, 2H), 7.22–7.15 (m, 1H), 3.72–3.58 (m, 2H), 3.29–3.04 (m, 2H), 2.70 (s, 2H), 2.47 (m, 2H), 1.85–1.75 (m, 2H).

Step C: (2R)-[[-2-[[1,1-Dimethylethoxy)carbonyl]amino]-2,2-dimethyl-1-oxoethyl]amino]-1H-indole-3-propanoic Acid Benzyl Ester To 5.0 g (16.5 mmol) of the commercially available N-tBOC-D-tryptophan in 100 mL of chloroform was added 1.80 mL (16.5 mmol) of benzyl alcohol, 0.20 g (1.65 mmol) of 4-N,N-dimethylamino pyridine (DMAP), and 3.20 g of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organics were washed with brine (100 mL), dried over potassium carbonate, filtered, and concentrated to give 5.46 g of the amine as a brown oil which was used without purification.

To 5.46 g of the above product. in 100 mL of chloroform was added 3.40 g (22.2 mmol) of HOBT, 4.60 g (22.2 mmol) of N-BOC-α-methyl alanine, and 5.32 g (28.0 mmol) of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam. $^1$H NMR(CDCl$_3$, 200 MHz) δ 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H).

Step D: (2R)-[[-2-[[1,1-Dimethylethoxy)carbonyl]amino]-2,2-dimethyl-1-oxoethyl]amino]-1H-indole-3-propanoic Acid To a solution of 4.75 g of the material from step B in 100 mL of ethanol was added 1.0 g of 10% Pd/C and stirred at RT under a H$_2$ balloon for 18 h: The catalyst was filtered off through a pad of celite and washed with ethyl acetate. The filtrate was concentrated to give 2.96 g of the acid as a colorless foam. $^1$H NMR (CDCl$_3$, 200MHz) δ 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H).

Step E: N-[1(R,S)-[(2,3-Dihydro-3-oxospiro[1H-indene-1,4'-piperidin]-1'-yl)carbonyl]-2-(indol-3-yl)ethyl]-2-[[1,1-dimethylethyloxy-carbonylamino-2-methylpropanamide The title compound (763 mg, 1.33 mmol) was prepared from 720 mg (2.39 mmol) of the intermediate from Step B and 929 mg (2.39 mmol) of the intermediate from Step D according to the procedure described for Example 1 (Step A). $^1$H NMR (400 MHz, CD$_3$OD, 2:1 mixture of conformers): 7.7–7.54 (m, 3H), 7.45–7.39 (m, 2 1/3H), 7.23 (s, 2/3H), 7.17–7.07 (m, 2 1/3H), 6.93–6.91 (m, 2/3H), 5.33–5.29 (m, 2/3H), 5.26–5.24 (m, 1/3H), 4.48–4.43 (m, 1H), 3.85–3.72 (m, 1H), 3.19–3.12 (m, 1H), 2.99–2.92 (dt, 2/3H) 2.60–2.36 (m, 2 2/3H), 2.20–1.89 (m, 2/3H), 1.45–1.38 (m, 15H), 1.31–1.21 (m, 1H), 1.12 (dt, 2/3H), 0.80–0.76 (m, 2/3H ), 0.10 (dt, 2/3H).

Step F: N-[1(R,S)-[(2,3-Dihydro-3-oxospiro[1H-indene-1, 4'-piperidin]-1'-yl)carbonyl]-2-(indol-3-yl)ethyl]-2-amino-2-methylpropanamide Hydrochloride A solution of 121 mg (0.211 mmol) of the intermediate from Step. E in a 1:1:0.1 mixture of dichloromethane, trifluroacetic acid and anisole was stirred for 30 minutes and then concentrated and azeotroped from toluene. Purification by flash chromatography (silica gel, dichloromethane/methanol/ammonium hydroxide 94:4:1) gave the amine. A 26 mg portion of this amine was dissolved in dioxane and 1.0 equivalent of 4 N HCl was added. The solution was concentrated to give the title compound. $^1$H NMR (400 MHz, CD$_{30}$OD, 3/1 mixture of conformers): 7.70–7.64 (m, 2H), 7.59–7.53 (m, 1H), 7.47–7.35 (m, 2 1/3H), 7.23 (s, 2/3H) 7.17–6.98 (m, 3H), 5.28–5.24 (m, 2/3H), 5.18 (t, 1/3H), 4.56–4.50 (m, 1/3H), 4.47–4.32 (m, 2/3H), 3.87–3.83 (m, 1H), 3.39–3.30 (m, 2/3H), 3.29–3.18 (m, 1 2/3H), 2.98 (dt, 2/3H). 2.59–2.44 (m, 2H), 2.10 (dt, 1/3H), 1.85 (dt, 1/3H), 1.63 (s, 1H), 1.62 (s, 2H), 1.61 (s, 2H), 1.51 (s, 1H), 1.50–1.34 (m, 2/3H), 1.27–1.26 (m, 2/3H), 1.10 (dt, 2/3H).

EXAMPLE 3

1'-[2-[(2-amino-2-methyl-1-oxopropyl)amino]-1-oxo-3-(phenyl-methoxy)propyl]spiro [1,H-indene-1,4'-piperidine]-3-carboxylic Acid Methylester Hydrochloride Step A: 3-[[Trifluoromethyl)sulfonyl]oxy]spiro[1H-indene-1,4'-piperidine]-1'-carboxylic acid-1,1-dimethylethylester To a solution of 420 mg (1.46 mmol) of the intermediate obtained from Example 2 (Step A) in 3.2 ml of THF at 0° C.

was added 3.2 ml (1.60 mmol 0.5 M in hexane) of potassium bis(trimethylsilyl)-amide. The reaction mixture was stirred for one hour and then 571 mg (1.60 mmol) of N-phenyltrifluromethane sulfonamide was added. After 4 hours the reaction was quenched with water and extracted with ethyl acetate. The organic layer was dried over sodium sulfate and concentrated. Purification by flash chromatography (silica gel, hexane/ethyl acetate 3:1) provided 483 mg (1.15 mmol) of the title compound as a white solid. $^1$HNMR (200 MHz, CDCl$_3$): 7.65–7.14 (m, 4 H), 6.66 (s, 1 H), 4.30–4.15 (m, 2 H), 3.24–2.96 (m, 2H), 2.06 (dt, 2 H), 1.50 (s, 9 H), 1.49–1.38 (m, 2 H).

Step B: Spiro[1H-indene-1,4'-piperidine]-3,1'-dicarboxylic acid-1'-(1,1dimethylethyl)-3-methyl Ester A solution of 434 mg (1.0 mmol) of the intermediate from Step A, 0.28 ml (2.0 mmol) of triethylamine, 16 mg (0.06 mmol) of triphenylphosphine, and 6.0 mg (0.03 mmol) of palladium acetate in 1.8 ml of methanol and 4.0 ml of DMF was purged for 5 minutes with carbon monoxide and then stirred under a carbon monoxide atmosphere for 5 hours. The reaction mixture was diluted with water and extracted repeatedly. with ethyl acetate. The ethyl acetate layer was dried over sodium sulfate and concentrated. Purification by flash chromatography (silica gel, hexane/ethyl acetate 6:1) provided 187 mg (0.54 mmol) of the title compound as a colorless oil. $^1$HNMR (200 MHz, CDCl$_3$): 7.99–7.94 (m, 1 H), 7.71 (s, 1 H), 7.34–7.26 (m, 3 H), 4.24–4.18 (m, 2 H), 3.91 (s, 3 H), 3.13 (dt, 2 H), 2.03 (dt, 2 H), 1.51 (s, 9 H), 1.46–1.25 (m, 2 H).

Step C: 2(R)-[[-2-[1,1-Dimethylethoxy)carbonyl]amino]-2, 2-dimethyl-1-oxoethyl]amino-2-(phenylmethoxy)ethyl)-1-propanoic Acid Allyl Ester The title compound was prepared from commerically available BOC-O-BEN-D-Serine and allyl alcohol, followed by TFA treatment and coupling to Boc-α-methylalanine following the procedure described in Example 2, Step C.

Step D: (2R)-[[-2-(1,1-Dimethylethoxy)carbonyl]amino]-2, 2-dimethyl-1-oxoethyl]amino-2-(phenylmethyloxy)ethyl)-1-propanoic Acid To a stirred solution of the crude intermediate obtained in Step A (6.7 g, 15.9 mmol), tetrakis (triphenylphosphine) palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1h and then diluted with ether (100 mL) and poured into ice-water. The organic layer was separated and the aqueous fraction was acidified with citric acid (20%), then extracted with EtOAc. The EtOAc extracts were washed with brine, dried over magnesium sulfate, filtered and evaporated to give the title compound as a solid. $^1$H NMR (400 Hz, CD$_3$OD) δ 7.3 (s, 5H), 4.7 (m, 1H), 4.5 (s, 2H), 4.0 (m, 1H), 3.6 (m, 1H), 1.4 (d, 6H), 1.3 (s, 9H).

Step E: 1'-[2-[[(1,1-Dimethylethyloxycarbonyl)-2-amino-2-methyl-1-oxopropyl)amino]-1-oxo-3-(phenylmethoxy) propyl]spiro-[1H-indene-1,4'-piperidine]-3-carboxylic Acid Methyl Ester The title compound (88 mg, 0.132 mmol) was prepared from the intermediate obtained in Step B (180 mg, 0.524 mmol) and the intermediate prepared in Step D (212 mg, 0.576 mmol) according to the procedure described in Example 1 Step B.

Step F: 1'-[2-[(2-Amino-2-methyl-1-oxopropyl)amino]-1-oxo-3-(phenylmethoxy)propyl]spiro[1H-indene-1,4'-piperidine]-3-carboxylic Acid Methyl Ester Hydrochloride The title compound (88 mg, 0.132 mmol)was prepared from the intermediate obtained in Step E (117 mg, 0.193 mmol) according to the procedure described in Example 1 Step C. $^1$HNMR (400 MHz, CD$_3$OD 1:1 mixture of conformers): 7.92–7.84 (m, 1 H), 7.86 (d, 1 H), 7.40–7.18 (m, 7 1/2 H), 6.98 (d, 1 H), 5.22–5.15 (m, 1 H), 4.61–4.52 (m, 3 H), 4.18 (d, 1 H), 3.90+3.88 (s, 3 H total), 3.81–3.73 (m, 2 H), 3.55–3.42 (m, 1 H), 3.15–3.08 (m, 1 H), 2.20–2.06 (m, 1/2 H), 2.03–1.92 (m, 1 1/2 H), 1.57+1.54+1.53+1.52 (s, 6 H total), 1.38–1.27 (m, 2 H).

EXAMPLE 4

N-[1(R)-[[3-(Hydroxymethyl)-2,3-dihydrospiro[1H-indene-1,4'-piperidin]-1'-yl]carbonyl]-2-(phenylmethoxy)ethyl]-2-amino-2-methylpropananmide Hydrochloride Step A: 1'-[2-[[(1,1-Dimethylethyloxycarbonyl)-2-amino-2-methyl- 1-oxopropyl)amino]-1-oxo-3-(phenylmethoxy) propyl]-2,3-dihydrospiro[1H-indene-1,4'-piperidine]-3-carboxylic Acid Methyl Ester To a suspension of Tellurium (52.6 mg, 0.412 mmol) in ethanol (2.0 ml) was added sodiumborohydride (36.6 mg, 0.99 mmol) and the mixture was refluxed for 10 minutes. A solution of the title compound from Example 3, Step E (100 mg, 0.165 mg) in ethanol (1.0 ml) was cannulated into the reaction mixture at room temperature. The reaction mixture was then stirred over night, filtered and concentrated. The residue was dissolved in ethyl acetate and 1 N KOH was added. The aqueous layer was then extracted with ethyl acetate (3×1 vol). The organic layers were dried over anhydrous sodium sulfate, filtered and concentrated. Flash chromatography (silica gel, methylene chloride/ethyl acetate 2:1) gave the title compound (91 mg, 0.15 mmol) as a clear glass.

Step B: N-[(R)-[[3-(Hydroxymethyl)-2,3-dihydrospiro[1H-indene-1,4'-piperidin]-1'-yl]carbonyl]-2-(phenylmethoxy) ethyl]-2-[[(1,1-dimethylethoxycarbonyl]amino-2-methylpropanamide A portion of the intermediate from Step A (42.1 mg, 0.069 mmol) was dissolved in methylene chloride and cooled to −10° C. DIBALH (0.172 ml, 0.172 mmol) was added and the reaction mixture was stirred until the starting material was consumed. The reaction was quenched with 3 drops of water and then a spatula of KF on alumina was added. The mixture was stirrred for 3 h, filtered and then stripped. The residue was purified by flash chromatography (silica gel, methylene chloride/acetone 4:1) to give the title compound (22.6 mg, 0.039 mmol).

Step C: N-[1(R)-[[3-(hydroxymethyl-)-2,3-dihydrospiro [1H-indene-1,4'-piperidin]-1'-yl]carbonyl]-2-(phenylmethoxy)ethyl]-2-amino-2-methylpropananmide Trifluroacetamide A solution of the intermediate prepared in Step B (12.1 mg, 0.21 mol) in a 1:1 mixture of methylene chloride and TFA was stirred at room temperature for 3 h. The solution was concentrated and the residue was azeotroped from toluene. MPLC (LH20 column, methanol ) gave the title compound (4.8 mg, 008 mmol). $^1$HNMR (400 MHz, CD$_3$OD 1:1 mixture of diastereomers and a 1:1 mixture of conformers): 7.40–7.09 (m, 8.5 H), 6.87–6.68 (m, 0.5 H), 5.20–5.14 (m, 1 H), 4.62–4.45 (m, 3 H), 4.09–3.95 (m, 1 H), 3.88–3.81 (m, 1 H), 3.78–3.61 (m 3 H), 2.95–2.86 (m, 1 H), 2.48–2.39 (m, 1 H), 2.13–2.09 (m, 0.5 H), 1.95–1.71(m, 2.5 H), 1.59–1.48 (m, 8 H).

EXAMPLE 5

N-[[1(R)-[[3-[(dimethylamino)carbonyl]-2,3-dihydrospiro[1H-indene-1,4'-piperidine]]-1'-yl]carbonyl]-2-(phenylmethoxy)ethyl]-2-amino-2-methylpropanamide Hydrochloride Step A: 1'-[2-[[(1,1-Dimethylethoxycarbonyl)-2-amino-methyl-1-oxopropylamino]-1-oxo-3-(phenylmethoxy)propyl]-2,3-dihydrospiro[1H-indene-1,4'-piperidine]-3-carboxylic Acid A portion of the intermediate from Example 4A, Step A (312 mg, 0.502 mmol) was dissloved in methanol (3.0 ml)/H$_2$O (1.0 ml) and lithium hydroxide was added (14.4 mg, 0.602 mmol) and the solution was stirred overnight. The solution was concentrated to dryness and the residue was dissolved in ethylacetate/1 N HCL. Extraction with ethyl acetate followed by drying and concentration gave the title compound (289 mg, 0.47 mmol).

Step B: N-[[1(R)-[[3-[(Dimethylamino)carbonyl]-2,3-dihydrospiro-[1H-indene-1,4'-piperidine]-1-yl]carbonyl]-2-(phenyl-methoxy)ethyl]-2-[[(2,2-dimethylethoxylcarbonyl]amino]-2-methylpropanamide The intermediate from Step A (17.5 mg, 0.028 mmol) was reacted with EDC (8.2 mg, 0.043 mmol), HOBT (5.8 mg, 0.043 ), NMM (4.5 mM, 0.043 mmol) and dimethyl amine hydrochloride (3.4 mg, 0.043 mmol) according to the procedure described in Example 1, Step A. Flash chromatography (silica gel, methylene chloride acetone 2:1) provided the title compound (15.2 mg, 0.023).

Step C: N-[[1(R)-[[3-[(Dimethylamino)carbonyl[-2,3-dihydrospiro-[1H-indene- 1,4'-piperidin]-1'-yl]carbonyl-2-(phenyl-methoxy)ethyl]-2-amino-2-methylpropanamide Hydrochloride The intermediate from Step B was stirred in a mixture of methanol, con HCL and water. The solution was concentrated and azeotroped from toluene and finally dried under vacuum to give the title compound (12.1 mg, .021 mmol).

EXAMPLE 6

Resolution of 1'[(1,1-Dimethylethoxy)carbonyl]-2,3-dihydrospiro(1H-indene-1,4'-piperidine]-3-carboxylic Acid Ethyl Ester Method A Enantiomer 1

Step A: 1'-[1,1-(Dimethylethoxy)carboxyl]-[1H-indene-1,4'-piperidine]-3-carboxylic Acid Ethyl Ester The title compound was prepared following the procedure described in Example 3, Step B except that ethanol was used instead of methanol.

$^1$HNMR (200 MHz, CDCl$_3$): 8.0–7.9 (m, 1 H), 7.7 (s, 1 H), 7.4–7.2 (m, 3 H), 4.39 (q, 2 H) 4.3–4.2 (m, 2 H), 3.13 (dt, 2 H), 2.03 (dt, 2 H), 1.51 (s, 9 H), 1.46–1.25 (m, 2 H), 1.44 (t,3 H).

Step B: 1'-(1,1-Dimethylethyloxy)carbonyl]-2,3-dihydrospiro[1H-indene-1,4'-piperidine]-3-carboxylic Acid To a solution of the title compound from Step A (4.0 g, 11.2 mmol) in methanol (30 ml) at 0° C. was added 2 N KOH (16.8 ml, 33.6 mmol). The reaction was warmed to room temperature and stirred for 3 h at which time TLC analysis showed that the starting material had been consumed. The methanol was removed under vacuum and the residue was dissloved in ethyl acetate. 1 N HCl was added and the layers were separated and the aqueous layer was extracted with ethyl acetate (3×1 vol). The combined organic layers were washed with saturated aqueous NaCl, dried over anhydrous sodium sulfate, filtered and concentrated to provide the title compound (3.28 g, 9.9 mmol) as a white solid.

$^1$HNMR (200 MHz, CDCl$_3$): 8.06–7.80 (m, 1 H), 7.86 (s, 1 H), 7.4–7.3 (m, 3 H), 4.32–4.18 (m, 2 H), 3.18 (dt, 2 H), 2.06 (dt, 2 H), 1.51 (s, 9 H), 1.46–1.25 (m, 2 H), H).

Step C: 1'-[(1,1-Dimethylethoxy)carbonyl]-2,3-dihydrospiro(1H-indene-1,4'-piperidine]-3-carboxylic Acid To a suspension of Pd/C (300 mg) in methanol (20 ml) and ethyl acetate (10 ml) was added the title compound (1.2 g, 3.6 mmol) from Step B. The reaction mixture was purged with hydrogen and then stirred under a hydrogen balloon for 1 h. The mixture was filtered through celite and concentrated to give the title compound (1.1 g, 33 mmol). $^1$HNMR (200 MHz, CDCl$_3$): 7.50–7.42 (m, 1 H), 7.34–7.12 (m, 3 H), 4.22–4.04 (m, 3 H), 3.06–2.84 (m, 2 H), 2.40 (d, 2 H), 1.88–1.6 (m, 4 H), 1.50 (s, 9 H).

Step D: 2,3-Dihydrospiro[1H-indene-1,4'-piperidine]-3,1'-dicarboxylic acid1'-(1,1-dimethylethyl)3-(1-[(ethoxy)-carbonyl]ethyl)Diester To a solution of the intermediate from Step C. in toluene at 0° C. was added sodium hydride (99 mg, 80%, 3.3 mmol). The reaction mixture was stirred for 15 minutes and then DMF (0.050 ml) and oxalyl chloride (3.0 ml 2 N in methylene chloride) were added. The reaction mixture was stirred for 1 h and then concentrated. The residue was redissolved in toluene and cooled to −10° C. S-Ethyllactate (0.413 mmol, 3.6 mmol) was added followed immediately by N-methyl pyrrolididne (1.1 ml, 10.5 mmol). The reaction was stirred for three minutes and then quenched with an excess of dimethylamino propyl amine. The toluene layer was diluted with ethyl acetate and washed with 1 N HCl and saturated aqueous sodium chloride. The organic layer was dried over anhydrous magnesium sulfate, filtered and concentrated. Flash Chromatography ( silica gel, hexane/ethyl acetate 4:1) gave a 5:1 mixture of diastereomers (725 mg). The mixture could be enriched to almost 10:1 by MPLC (silica gel, hexane/ethyl acetate 10:1).

$^1$HNMR (200 MHz, CDCl$_3$): 7.58–7.49 (m, 1 H), 7.32–7.12 (m, 3 H), 5.15 (q, 4 H), 4.35–4.04 (m, 4 H), 3.08–2.85 (m, 2 H), 2.45–2.36 (m, 2 H), 1.94–1.60 (m, 4 H), 1.54 (d, 3 H), 1.50 (s, 9 H), 1.22 (t, 3 H).

Step E: 1'-[(1,1-Dimethylethoxy)carbonyl]-2,3-dihydrospiro(1H-indene-1,4'-piperidine]-3-carboxylic Acid Ethyl Ester Enantiomer 1

To a solution of the title compound from Step D (400 mg, 0.928 mmol) in ethanol (10 ml) was added titanium isopropoxide (0.303 ml, 1.02 mmol). The reaction mixture was heated to reflux until TLC analysis showed that the starting material had been consumed. The solvent was removed under vacuum and the residue was purified by flash chromatography (silica gel, hexane/ethyl acetate 6:1) to give the title compound (313 mg, 0.87 mmol)

EXAMPLE 7

Resolution of 1'-[(1,1-Dimethylethoxy)carbonyl]-2,3-dihydrospiro(1H-indene-1,4'-piperidine]-3-carboxylic Acid Ethyl Ester Method A Enantiomer 2

Step A: 2,3-Dihydrospiro[1H-indene-1,4'-piperidine]3,1'-dicarboxylic acid 1'-(1,1-dimethylethyl)3-(2-oxo-4,4-dimethyltetrahydrofuran-3-yl) Diester The title compound (437 mg, 0.98 mmol) was prepared from the intermediate prepared in Example 6, Step C (512 mg, 1.55 mmol), following the procedure used in Example 6, Step D, except that R-Pantolactone (242 mg, 1.86 mmol) was used instead of S-ethyllactate.

$^1$HNMR (200 MHz, CDCl$_3$): 7.58–7.48 (m, 1 H), 7.32–7.15 (m, 3 H), 5.42 (s, 1 H), 4.35–4.05 (m, 5 H), 3.05–2.85 (m, 2 H), 2.55–2.30 (m, 2 H), 2.0–1.60 (m, 2 H), 1.50 (s, 9 H), 1.32–1.18 (m, 2 H), 1.20 (s, 3 H), 1.08 (s, 3 H).

Step B: 1'-[(1,1-Dimethylethoxy)carbonyl]-2,3-dihydrospiro(1H-indene-1,4'-piperidine]-3-carboxylic Acid Ethyl Ester Enantiomer 2

The title compound (302 mg, 0.84 mmol) was prepared from the intermediate prepared in Step A (413 mg, 0.94 mmol) following the procedure used in Example 6, Step E.

EXAMPLE 8

Resolution of 1'-[(1,1-Dimethylethoxy)carbonyl]-2,3-dihydrospiro(1H-indene-1,4'-piperidine]-3-carboxylic Acid Ethyl Ester Method B Enantiomer 1

Step A: 1'-(1,1-Dimethylethyloxycarbonyl]-2,3-dihydrospiro[1H-indene-1,4'-piperidine]-3-carboxylic Acid Enantiomer 1

To a solution of the title compound from Example 6, Step C (2.5 g, 7.5 mmol) in toluene (10 ml) was added R-methyl benzylamine. The reaction mixture was warmed until a clear solution was obtained and then cooled to room temperature. A seed crystal (obtained from a similar experiment on a smaller scale) was added and the solution was stored for 18 h at room temperature and then for 1 h at 0° C. The crystals were recovered by filtration and then dissloved in 1 N HCl. The acid solution was extracted with ethyl acetate (3×1 Vol). The organic layer was washed with 1 N HCl (1×vol), saturated aqueous sodium chloride, dried over anydrous magnesium sulfate, filtered and concentrated to provide the title compound (800 mg, 2.4 mmol) as a white solid.

Step B: 1'-[(1,1-Dimethylethoxy)carbonyl]-2,3-dihydrospiro(1H-indene-1,4'-piperidine]-3-carboxylic Acid Ethyl Ester Enantiomer 1

To a solution of the title compound from Step A (800 mg, 2.4 mmol) in methylene chloride/ethanol 5:1 at 0° C. was added DMAP (30 mg, 0.245 mmol) and EDC (605 mg, 3.16 mmol). The reaction mixture was stirred for 1 h and then concentrated to one half of it's original volume and loaded onto a flash column. Flash chromatography (silica gel, hexane/ethyl acetate 4:1) gave the title compound (800 mg, 2.2 mmol). HPLC analysis (chiralcel OD, 98.5% hexane/1.5% isopropanol, 35° C., 1 ml/min. $E_1$ retention time 11.5 min; $E_2$ retention time 15.8 min) showed it to be approximately a 30:1 mixture of enantiomers.

EXAMPLE 9

Resolution of 1'-[(1,1-Dimethylethoxy)carbonyl]-2,3-dihydrospiro(1H-indene-1,4'-piperidine]-3-carboxylic Acid Ethyl Ester Methdd B Enantiomer 2

Step A: 1'-(1,1-Dimethylethyloxy)carbonyl]-2,3-dihydrospiro[1H-indene-1,4'-piperidine]-3-carboxylic Acid Enantiomer 2

The title compound from Example 6, Step C (2.63 g, 7.9 mmol) was resolved using the procedure described in Example 83D Step A except that S-methyl benzylamine (1.02 ml, 7.9 mmol) was used. The title compound (798 mg, 2.4 mmol) was obtained as a white solid.

Step B: 1'-[(1,1-Dimethylethoxy)carbonyl[-2,3-dihydrospiro(1H-indene-1,4'-piperidine]-3-carboxylic Acid Ethyl Ester Enantiomer 2

The title compound (623 mg ,1.73 mmol) was prepared from the title compound of Step A (601 mg ,1.81 mmol) and EDC (571 mg, 2.98 mmol) in a 5:1 mixture of methylene chloride and ethanol. HPLC analysis (chiralcel OD, [4.6 mm, 250 mm] 98.5% hexane/1.5% isopropanol, 35° C., 1 ml/min. $E_1$ retention time 11.5 min; $E_2$ retention time 15.8 min) showed it to be approximately a 35:1 mixture of enantiomers.

The absolute configuration of the compound prepared in Example 83E has been determined by single crystal X-ray analysis to be "R".Therefore all compounds prepared from 83E have R-stereochemistry at the spiroindane benzylic center and all compounds prepared from Example 8 have the S-configuration at this center.

EXAMPLE 10

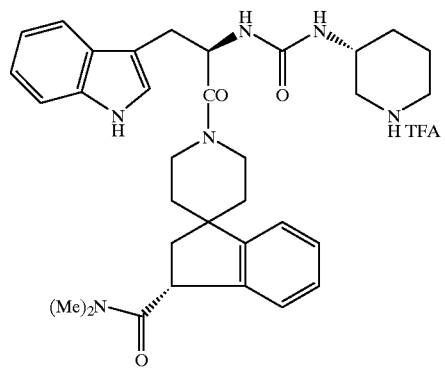

Step A:

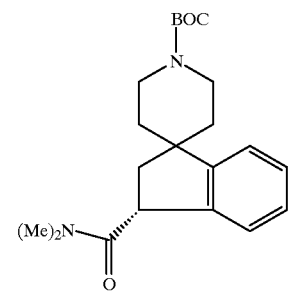

A solution of the title compound from Example 9 Step A (14.0 g, 42 mmol) in dichloromethane was cooled to 0° C. and dimethylamine (25.4 mL, 2M in THF) was added. The mixture was stirred for ten minutes at 0° C. and then EDC and DMAP were added. The reaction mixture was stirred for four hours at 0° C. and then quenched with 1 N HCl. The aqueous layers were extracted with dichloromethane and the combined organic layers were then washed with water and brine and dried over sodium sulfate. The crude product was purified by flash chromatography (dichloromethane/acetone 9:1) to give the title compound (12.2 g). HPLC analysis (chiralcel OD-R, 50% 0.5 N NaClO₄/50% acetonitrile, 0.5 ml/min. $E_1$ retention time 20.8 min, $E_1$ prepared from the intermediate in Example 83D Step A as in this example; $E_2$ retention time 24.7 min) showed it to be approximately a 1:200 mixture of enantiomers. ¹HNMR (400 MHz, CDCl₃): 7.25–7.05 (m, 4H), 4.35 (t, 1H), 4.20–4.10 (m, 2H), 3.25 (s, 3H), 3.05 (s, 3H), 2.90–2.85 (m, 2H), 2.42–2.28, (m, 2H), 1.95 (dt, 1H), 1.75–1.60 (m, 2H), 1.52–1.50 (m, 1H), 1.49 (s, 9H).

Step B:

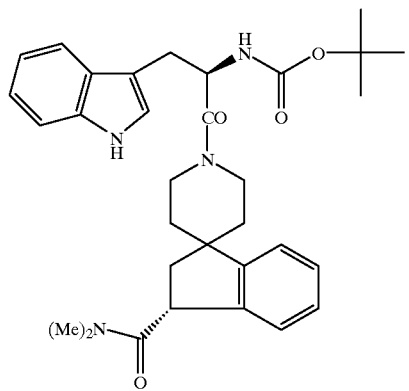

The title compound from Step A (6.4 g, 18.4 mMol) was stirred in ethyl acetate saturated with HCl for two hours and then concentrated and azeotroped from dichloromethane (2×) and toluene (1×). The residue was dissolved in dichloromethane, cooled to 0° C. and Boc-D- tryptophan (6.2 g, 20.2 mMol), NMM (2.0 mL, 18.4 mMol), HOBT (3.7 g, 27.6 mMol) and finally EDC (5.27 g, 27.6 mMol) were added. The reaction mixture was stirred at room temperature overnight and then poured into ethyl acetate. The organic layer was washed with saturated bicarb, 1 N HCl, water and finally brine. The organic layers were dried over magnesium sulfate, filtered and concentrated. Purification by. flash chromatography (ethyl acetate) gave the title compound (4.6 g).

Step C:

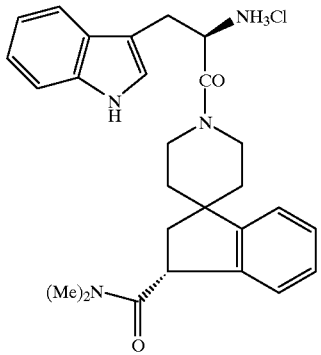

The title compound was prepared from the title compound of Step B by treatment with a saturated solution of HCl in ethyl acetate. Removal of the volatiles followed by azeotroping from dichloromethane and toluene provided the title compound as a white solid.

Step D:

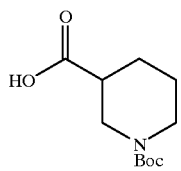

To ethyl-nipecotate (60 g, 0.382 m) in isopropanol (300 ml) was added 2 N NaOH (400 ml). The solution was stirred for 3 hrs and then di-t-butyl-dicarbonate (83.3 g, 0.382 m) was added. The reaction mixture was stirred overnight and the is propanol was removed in vacco. The mixture was made acidic with 1 N HCl and extracted with ethyl acetate (3×1 vol). The organic layer was washed with water and brine and then dried over MgSO$_4$. The dried organic layers were filtered and concentrated to give the title compound (77.8 g, 0.302 m).

Step E:

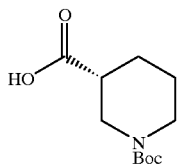

dl-N-Boc-nipecotic acid (78 g, 342 mmol) was dissolved in hot 9:1 ethyl acetate/methanol solution (1,600 mL). While stirring the solution, (S)-α-methyl-benzylamine (0.8 eq). was added in one portion. Stirring was discontinued after 1 minute and the mixture allowed to cool slowly to room temperature for 16 h. The precipitated salt was filtered and recrystallized from 9:1 ethyl acetate/methanol solution (900 mL). This was also allowed to cool to room temperature over several hours. The resulting precipitate was filtered. The filtrate was partitioned between ethyl acetate/1 N HCl, the phases separated and the aqueous portion extracted again with EtOAc. The combined organic portions were extracted once with 1 N HCl, water, washed with brine and dried over MgSO$_4$. The solvent was removed in vacuo to provide 14.65 g of the R-(+)-N-Boc-nipecotic acid. Rotation: $[\alpha]_D = +49.9°$ /methanol.

Step F:

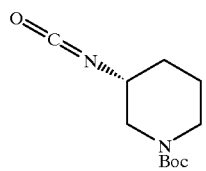

DPPA (5.8 ml, 27 mmol) and TEA (3.8 ml, 27 mmol) were added to the title compound from the previous step (5.0 g, 22 mmol) in toluene (78.4 ml) and the mixture was refluxed for 3 hrs. The toluene solution of isocyanate was used without characterization or purification.

Step G:

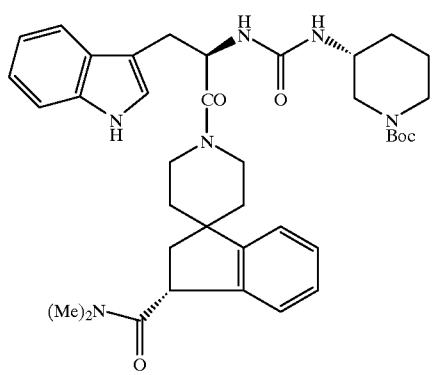

The intermediate from Step F above (0.92 ml, 0.25 M toluene, 2.29 mmol) was added to the title compound from Step C above (1.0 g, 2.08 mmol) and NMM (0.458 mg, 4.16 mmol) in dichloromethane at 0° C. The reaction mixture was stirred at room temperature for 2 hrs and then diluted with methylene choloride and washed with 1 N HCl, water, and brine. The organic layers were dried over MgSO$_4$, filtered and concentrated. Purification by flash chromatography (dichloromethane/acetone 3/1 to 1/1 ) gave the title compound (1.1 g, 1.64 mmol).

Step H:

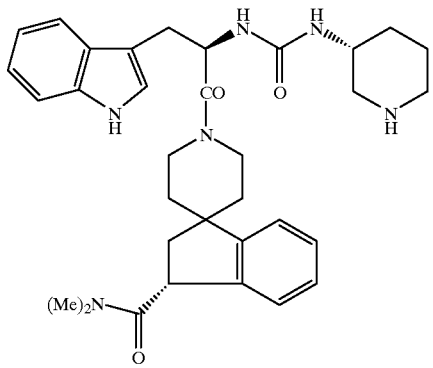

The title compound from the previous step (0.468 g, 0.696 mmol) was treated with dichloromethane/TFA (1:1) for 2 hrs. The solution was concentrated and azeotroped from toluene. Purification by MPLC (RP-18, 70% H$_2$O, 30% CH$_3$CN 1% TFA) followed by lyopholyzation gave the title compound (393 mg, 0.574 mmol). $^1$H NMR ($\delta$, CD$_3$OD, 500 MHz, mix of rotamers): 7.63 (d, J=7.8 Hz, 2/3H), 7.52 (d, J=8.0 Hz, 1/3H), 7.35 (m, 1H), 7.15 (m, 6H), 6.67 (d, J=7.5 Hz, 1H), 5.15 (m, 2/3H), 5.08 (m, 1/3H), 4.38 (m, 2H), 3.80 (m, 2H), 3.30 (m, 2H), 3.21 (s, 3H), 3.20 (m, 4H), 3.00 (m, 2H), 2.98 (s, 3H), 2.85 (m, 1H), 2.60 (m, 2H), 2.30 (m, 1H), 1.90 (m, 4H), 1.50 (m, 3H), 1.20 (m, 2/3H), 0.90 (d, J=2.1 Hz, 2/3H), −0.38 (m, 2/3H). MS-FAB: 571.3 (M+1).

EXAMPLE 11

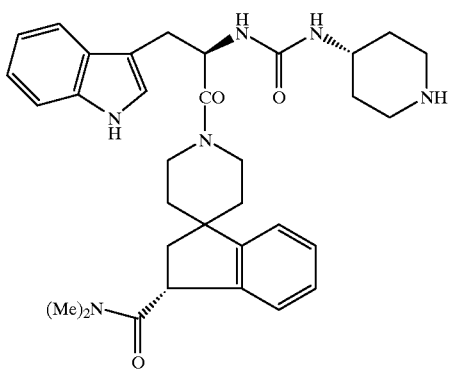

Step A:

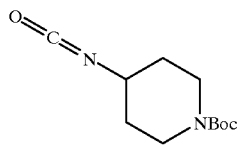

The title compound was prepared from N-Boc-isonipecotic acid according to the procedure described in Example 10 Step F.

Step B:

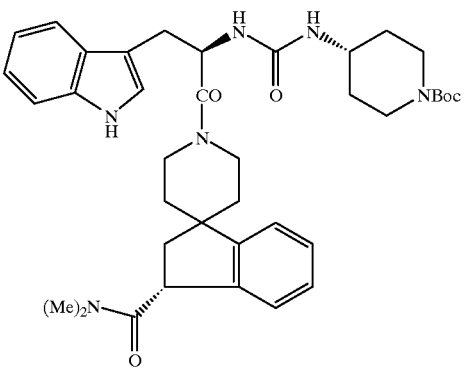

The title compound (68 mg, 0.1 mmol) was prepared from the title compound from Step A and the title compound from Example 10 Step C (80 mg, 0.17 mmol) according to the procedure described in Example 10 Step G.

Step C:

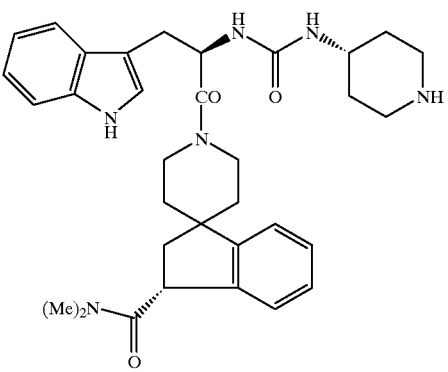

The title compound (69 mg) was prepared from the title compound (68 mg) of the previous step according to the procedure described in Example 10 Step H. Key $^1$H NMR ($\delta$, CD$_3$OD, 400 MHz, mixture of rotamers): 3.21 (s, 3H), 3.00 (s, 3H), 0.90 (m, 2/3H), −0.10 (m, 2/3H). MS-FAB: 571.3 (M+1).

EXAMPLE 12

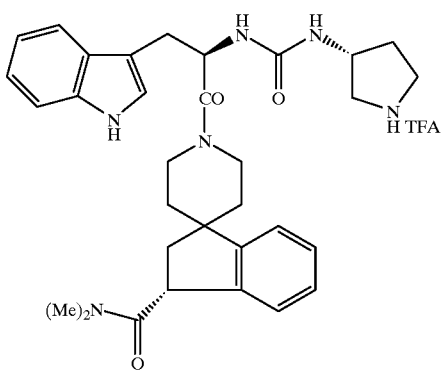

Step A:

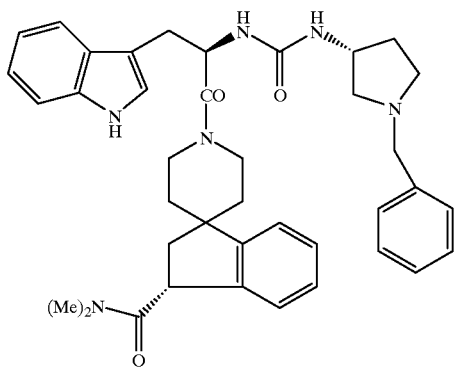

DSC (45 mg, 0.17 mmol) was added to R-1-benzyl-3-amino-pyrrolidine (30 mg, 0.17 mmol) and NMM (0.51 ml, 0.465 mmol) in dichloromethane. The reaction mixture was stirred for 2 hrs and then the intermediate prepared in Example 10 Step C (70 mg, 0.14 mmol) was added and the reaction mixture was stirred overnight. The reaction mixture was applied to a prep TLC plate and eluted with dichloromethane methanol (9:1) to give the title compound (67 mg).

Step B:

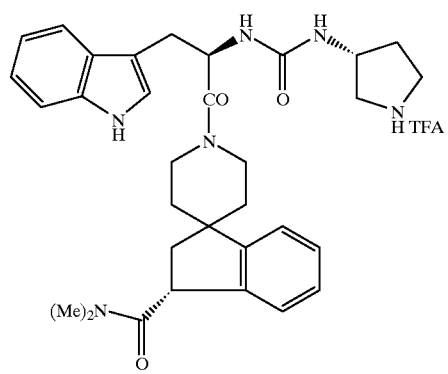

The title compound from Step A was hydrogenated with Pd/C for 4 hrs. The solution was filtered through celite and concentrated. The residue was treated with TFA and purified by MPLC (LH$_{20}$, methanol) to give the title compound. Key $^1$H NMR ($\delta$, CD$_3$OD, 400 MHz, mix of rotamers): 3.21 (s, 3H), 2.99 (s, 3H), 0.89 (m, 2/3H), −0.10 (m, 2/3H). MS-FAB: 557.4 (M+1).

EXAMPLE 13

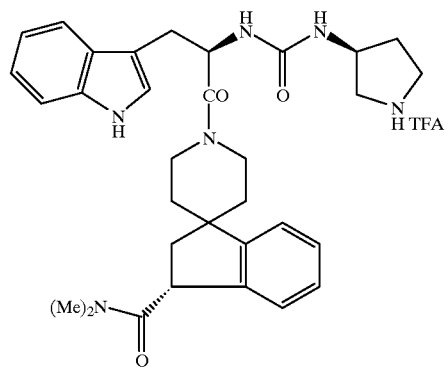

Step A:

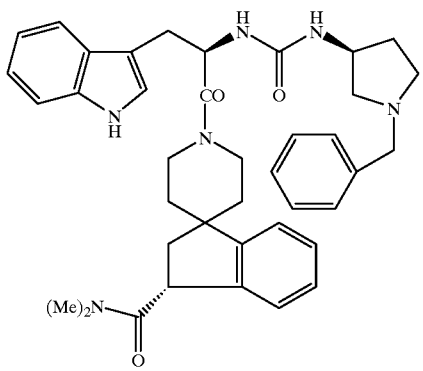

The title compound (50 mg) was prepared from the title compound of Example 10 Step C (70 mg, 014 mmol) and S-1-benzyl-3-aminopyrrolidine (30 mg, 0.17 mmol) according to the procedure described in Example 12 Step A.

Step B:

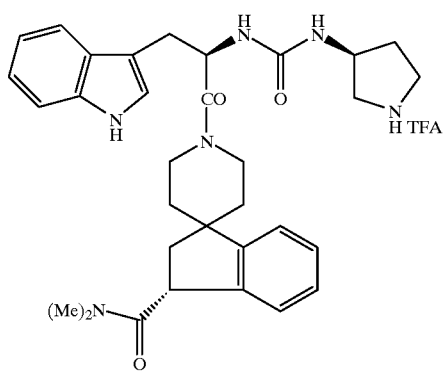

The title compound (16 mg) was prepared from the intermediate prepared in Step A according to the procedure described in Example 12 Step B. Key $^1$H NMR ($\delta$, CD$_3$OD, 400 MHz, mix of rotamers): 3.22 (s, 3H), 2.99 (s, 3H), 0.9 (m, 2/3H), −0.05 (m, 2/3H). MS-FAB: 557.2 (M+1).

EXAMPLE 14

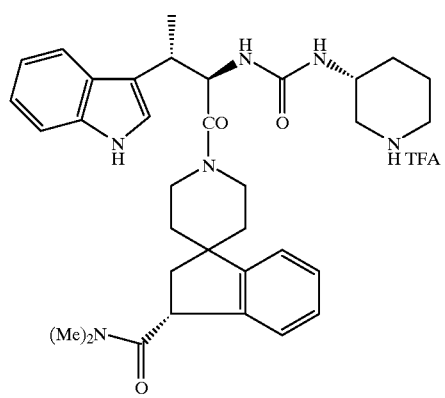

Step A:

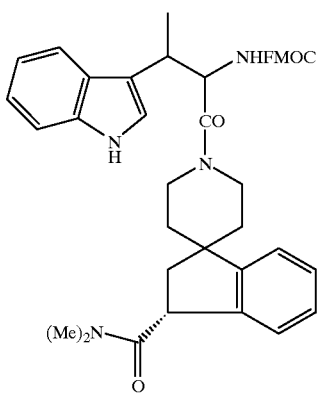

EDC was added to a mixture of the intermediate prepared in Example 10 Step A, NMM, HOBT, and FMOC-β-methyl tryptophan (R,S and S,R) (*J. AM. Chem. Soc.* 1957, 79, 2217) in dichloromethane at 0° C. The reaction mixture was stirred overnight at room temperature and then the solution was poured into ethyl acetate and washed with 1 N HCl, sat bicarb, and brine. The organic layers were dried over MgSO$_4$, filtered and concentrated. Purification by flash chromatography (ethyl acetate) gave the title compound (141 mg).

Step B:

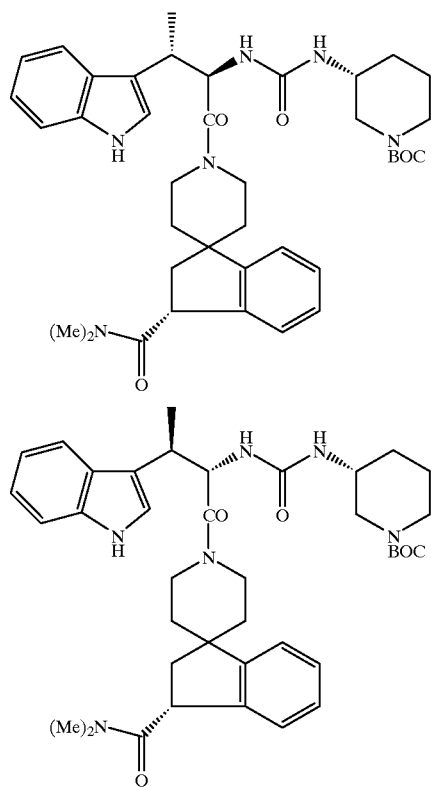

Diethylamine was added to the intermediate prepared in Step A in dichloromethane. The solution was stirred for 1 hr and then concentrated. The residue was dissolved in dichloromethane and the intermediate from Example 10 Step F was added. The reaction mixture was stirred for 1 hr and then diluted with dichloromethane and washed with 1 N HCl, water, and brine. The organic layer was dried over MgSO$_4$, filtered and concentrated. Purification by MPLC (ethyl acetate/methanol 94:6) gave d1 (38 mg) and d2 (35 mg).

Step C:

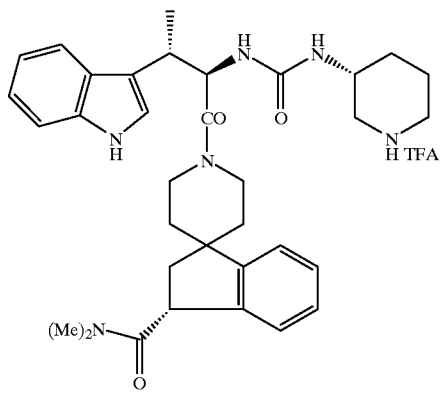

The title compound (22 mg) was obtained from d1 (28 mg) of the previous step according to the procedure described in Example 10 Step H. Key $^1$H NMR (δ, CD$_3$OD, 400 MHz, 3:1 mixture of rotamers): 7.66 (d, 3/4 H), 7.54 (d, 1/4 H), 5.00 (d, 3/4 H), 4.93 (d, 1/4 H),4.38–4.21 (m, 1H), 3.24 (s, 3/4 H); 3.21 (s, 9/4 H), 3.02 (3/4 H), 2.97 (9/4 H), 1.51–1.47 (m, 3 H), 1.99–1.87 (m, 3/4 H), 1.76 (dt, 3/4 H), −0.233 (dt, 3/4 H). ESI-MS: 585 (M+1).

EXAMPLE 15

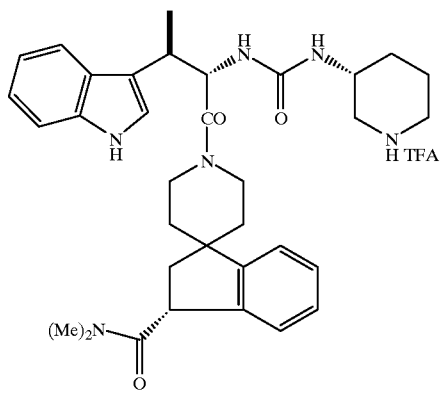

Step A:

The title compound was prepared from the intermediate prepared in Example 14 Step B d2(31 mg) according to the procedure of Example 14 Step C. Key $^1$H NMR (δ, CD$_3$OD, 400 MHz, 3:1 mixture of rotamers): 7.67 (d, 3/4 H), 7.56 (d, 1/4 H), 5.04 (d, 3/4 H), 4.95 (d, 1/4 H), 4.37 (t, 1 H), 3.24 (s, 3/4 H), 3.21 (s, 9/4 H), 3.01 (s, 3/4 H), 2.97 (s, 9/4 H), 2.59 (dt, 3/4 H), 1.0 (dd, 3/4 H), 0.42 (dt, 3/4 H), 0.14 (dt, 3/4 H). ESI-MS: 585 (M+1).

EXAMPLE 16

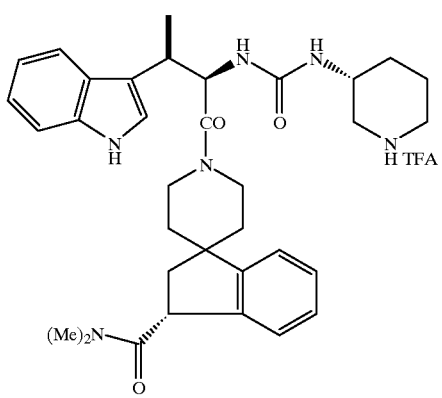

Step A:

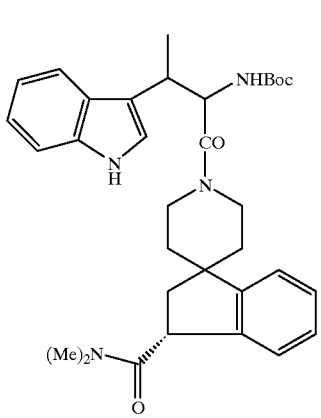

The title compound was prepared from FMOC β-methyl-tryptophan (R,R and S,S) and the intermediate prepared in Example 10 Step A according to the procedure of Example 14 Step A.

Step B:

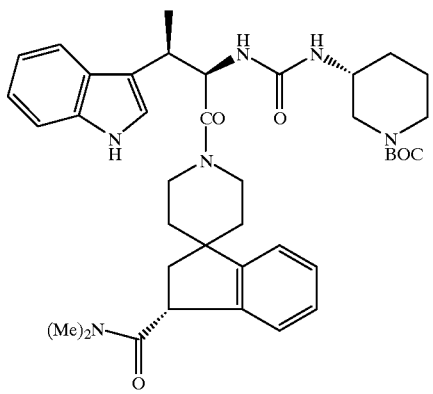

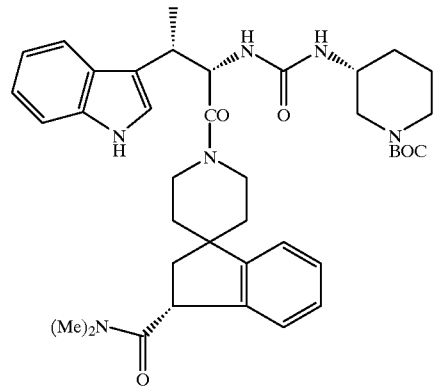

The title compound (d1 33 mg, d2 31 mg) was prepared from the intermediate prepared in the previous step according to the procedure described in Example 14 Step B.

Step C:

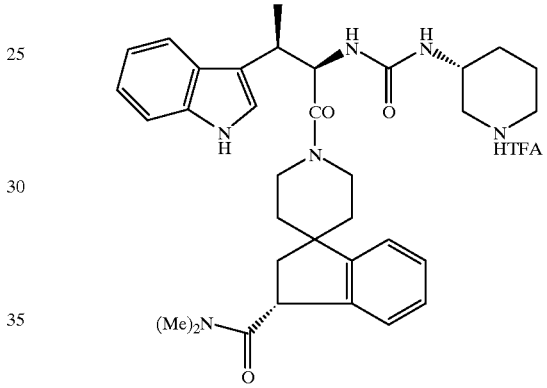

The title compound (23 mg) was prepared from d1 (30 mg) of the previous step according to the procedure of Example 14 Step C. Key $^1$H NMR (δ, CD$_3$OD, 400 MHz, 1:1 mixture of rotamers): 7.77 (d, 1/2 H), 7.56 (1/2 H), 5.25 (d, 1/2 H), 5.11 (d, 1/2 H), 3.24 (s, 3/2 H), 3.04 (s, 3/2 H), 3.01 (s, 3/2 H), 1.48 (d, 3/2 H), 1.42 (d, 3/2 H), 1.08–1.05 (m, 1/2 H), 0.69 (dt, 1/2 H). ESI-MS: 585 (M+1).

EXAMPLE 17

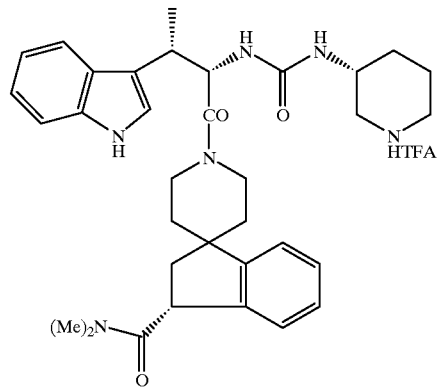

Step A:

The title compound (24 mg) was prepared from d2 (30 mg) of Example 16 Step B according to the procedure of Example 16 Step C. Key $^1$H NMR (δ, CD$_3$OD, 400 MHz, 1:1 mixture of rotamers): 7.79 (d, 1/2 H), 7.59 (d, 1/2 H), 5.29 (d, 1/2 H), 5.11 (d, 1/2 H), 3.26 (s 3/2 H), 3.03 (s, 3/2 H), 2.99 (s, 3/2 H), 1.48 (d, 3/2 H), 1.39(d, 3/2 H), 1.13–1.10 (m, 1/2 H), 1.01 (dt, 1/2 H). ESI-MS: 585 (M+1).

EXAMPLE 18

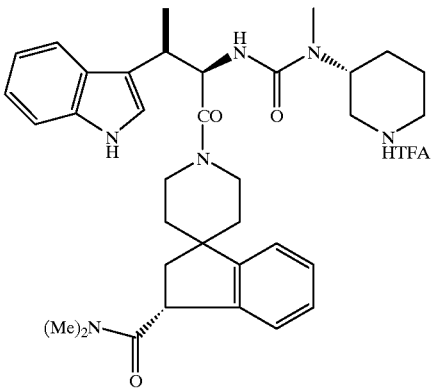

Step A: N-acetyl-Threo-(2R,3S)-β-methyltryptophanR-(+)-α-methylbenzylamine Salt

Racemic β-methyltryptophan was prepared by the method of Snyder and Matteson (*J. Am. Chem. Soc.* 1957, 79, 2217.) Isomer A (100 g) was suspended in 1.25L of 90/10 acetone water at 20° C. and 50 mL of R-(+)-α-methylbenzylamine was added in one portion. The suspension cleared briefly before a thick white suspension formed which quickly turned to a solid mass. After aging overnight, an additional 500 mL of acetone was added to facilitate agitation and filtration. The suspension was filtered and the cake washed with 500 mL of acetone and sucked to a damp cake. The solid was suspended in 2.5 L of 90/10 acetone/water and heated to boiling on a steam bath. The white slurry was allowed to cool to 20° C. overnight. The product was collected by filtration, washed with acetone and dried yielding 39.1 g of the title compound. α=+9.1° (c=1, MeOH). Stereochemical assignments were made by comparison to published compounds: *J. Org. Chem.* 1994, 59, 4239 and *J. Org. Chem.* 1995,60,4978.

Step B: N-acetyl-Threo-(2S,3R)-β-methyltryptophan S-(-)-α-methylbenzyl Amine Salt The mother liquors from the Step A were combined and concentrated to ca. 1 L and 400 mL of 1 N HCl was added. The resulting suspension was stirred for 1 hr initially at 20° C. then at 0° C. The product was filtered and washed with water until the filtrate was neutral. The product was sucked to a damp cake weighing 79 g. The solid was suspended in 1 L of 95% acetone/water and 40 mL of S-(-)-α-methylbenzylamine was added followed by 1 L of 90% acetone/water. After a few minutes a solid mass formed. An additional 500 mL of acetone was added and the mixture heated on a steam bath for ca. 0.5 hr. This was then allowed to stand at 20° C. overnight. The product was collected by filtration, washed with 500 mL of acetone, and sucked to a damp cake. The product was suspended in 2 L of 95% acetone/water and heated on a steam bath to boiling. The white suspension was allowed to cool to 20° C. overnight. The product was collected by filtration, washed with 500 mL of acetone and dried yielding 54 g. α=-9.0 ° (c=1, MeOH).

Step C: N-acetyl-Erythro (2R,3R)-β-methyltryptophan R-(+)-α-methylbenzylamine Salt 170 g of Isomer B (see ref. in Step A) which was a brittle foam containing ethyl acetate was dissolved in 2.5 L of ethyl acetate containing 100 mL of ethanol. To this was added 60 mL of R-(+)-α-methylbenzylamine. After 10 min, an additional 2 L of ethyl acetate was added and the resulting thick suspension was aged at 20° C. for 3 days. The product was collected by filtration, washed with ethyl acetate and sucked to a damp cake. The salt was reslurried four times with hot ethyl acetate containing 2% water (1×2.5 L, 2×6 L, and 1×8 L). The yield of dried product was 43.2 g of salt. α=-19.6° (c=1, MeOH).

Step D: N-acetyl-Erythro (2S,3S)-β-methyltryptophan S-(-)-α-methylbenzyl Amine Salt The mother liquors from the Step C were combined and concentrated to ca. 2 L and washed twice with 500 mL 1 N HCl. The washes were back extracted once with ethyl acatate, and the combined ethyl acetate extracts washed twice with brine. The solution was diluted to 6 L with ethyl acatate and 60 mL of S-(-)-α-methylbenzylamine was added. After 10 min the resulting suspension was heated to boiling. The suspension was allowed to cool to ambient temperature with stirring overnight. The product was collected by filtration washed with ethyl acetate and sucked to a damp cake. The salt was suspended in 6 L of ethyl acetate and suspension was heated to boiling. The suspension was allowed to cool to ambient temperature with stirring overnight. The product was collected by filtration washed with ethyl acetate and dried. The yield of dried product was 65.8 g of salt. α=+19.7° (c=1, MeOH).

Step E: N-acetyl-threo-(2S,3R)-β-methyltryptophan

The salt from Step B (53 g) was stirred with 400 mL 1 N HCl at 20° C. for 20 min. The suspension was filtered and the cake washed with water until the filtrate was neutral. The wet cake was used directly for the next reaction. A sample was dried affording the title compound. α=-26.4° (c=1, MeOH).

Step F: threo-(2S,3R)-β-methyltryptophan

The wet cake from Step E was suspended in with 400 mL of 1 N HCl and refluxed for 12 hours. The solution was cooled to 20° C., and half of the solution was used for Step G. The title compound isolated by adjusting the pH to 7.0 with sodium hydroxide, cooling the resulting suspension to 0° C., filtering, washing the cake with water and drying. α=-29.30° (c=0.9, H$_2$O).

Step G: N-t-BOC-threo-(2S,3R)-β-methyltryptophan

The pH of the aqueous solution from Step F was adjusted to 7 with sodium hydroxide and cooled to 0° C. 20 g of potassium carbonate, 19 g of di-t-butyldicarbonate, and 150 mL of THF were added. The mixture was allowed to warm slowly to ambient temperature overnight. The reaction was extracted twice with ether, the aqueous acidified with 2 N HCl and extracted twice with ethyl acetate. The combined ethyl acetate extracts were washed with brine, dried with MgSO$_4$, filtered and concentrated affording 21.2 g of the title compound.

Step H: N-acetyl-threo-(2R,3S)-β-methyltryptophan

The title compound was prepared following the procedure of Step E. α=+26.6° (c=1, MeOH).

Step I: threo-(2R,3S)-β-methyltryptophan

The title compound was prepared following the procedure of Step F. α=+30.6° (c=0.9, H$_2$O).

Step J: N-t-BOC-threo-(2R,3S)-β-methyltryptophan

The title compound was prepared following the procedure of Step G.

Step K: N-acetyl-Erythro (2S,3S)-β-methyltryptophan

The salt from Example 4 (65 g) was stirred with 250 mL 1 N HCl and 1.5 L of ethyl acetate at ambient temperature for 5 min. The layers were partitioned and the ethyl acetate layer was washed with 1 N HCl, H$_2$O and brine, dried with MgSO₄, filtered and concentrated to afford the title compound as a brittle foam.

Step L: Erythro (2S,3S)-β-methyltryptophan

The product from Step K was suspended in with 500 mL of 2 N HCl and refluxed for 4 hours. The solution was cooled to 20° C., and half of the solution was used for Step M. The title compound isolated as a foam by concentrating the solution in vacuo.

Step M: N-t-BOC-Erythro (2S,3S)-β-methyltryptophan

The pH of the aqueous solution from Step F was adjusted to 7 with sodium hydroxide and cooled to 0° C. 24 g of potassium carbonate, 22 g of di-t-butyldicarbonate, and 150 mL of THF were added. The mixture was allowed to warm slowly to ambient temperature overnight. The reaction was extracted twice with ether The aqueous acidified with 2 N HCl and extracted twice with ethyl acetate. The combined ethyl acetate extracts were washed with brine, dried with MgSO₄ filtered and concentrated. The solid was redissolved in ether, and the ether removed in vacuo while flushing with hexanes. The resulting slurry was filtered and dried affording 20.1 g of the title compound.

Step N: N-acetyl-threo-(2R,3R)-β-methyltryptophan

The title compound was prepared following the procedure of Step K. α=° (c=1, MeOH).

Step O: threo-(2R,3R)-β-methyltryptophan

The title compound was prepared following the procedure of Step L. α=° (c=0.9, H₂O).

Step P: N-t-BOC-threo-(2R,3R)-β-methyltryptophan

The title compound was prepared following the procedure of Step M.

Step Q:

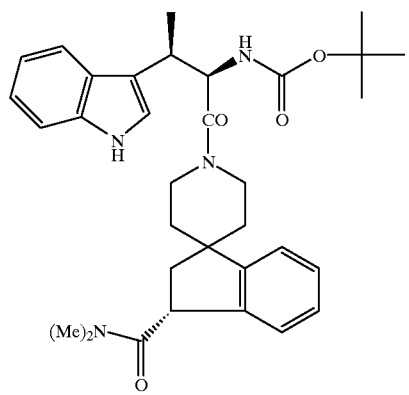

A sample of the title compound from Example 10 Step A was deprotected with a saturated solution of HCl in ethyl acetate as above to give the hydrochoride salt (6.3 g, 21 mmol). To this salt in dichloromethane at 0° C. was added (R,R)-β-methyltryptophan (7.0 g, 22 mmol), HOBT (4.4 g, 33 mmol), NMM (4.83 ml, 44 mmol) and finally EDC (6.3 g, 33 mmol). The reaction mixture was warmed to room temperature and stirred overnight. It was then poured into ethyl acetate and washed with 1 N HCl, saturated bicarb, and brine then dried over magnesium sulfate. The organic layer was filtered and concentrated. Purification by flash chromatography (ethyl acetate) provided the title compound (10 g, 17.9 mmol).

Step R:

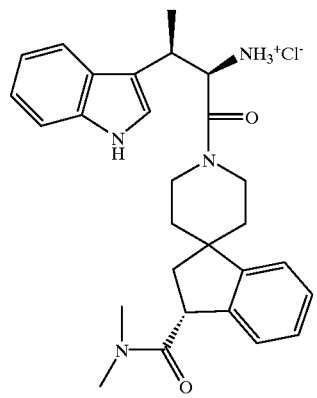

A solution of the N-Boc dipeptide from the previous step (1.32 g, 2.6 mmol)) in ethyl acetate (8 mL) was cooled to 0° C. While stirring, HCl/ethyl acetate was added to the mixture (10 mL). The reaction was stirred for 20 minutes, until TLC analysis indicated that the reaction was complete. The solution was then concentrated to afford 1.25 g of the product (100%). ESI-MS calc. for $C_{28}H_{33}N_4O_2$: 457; Found 458 (M+H).

Step S:

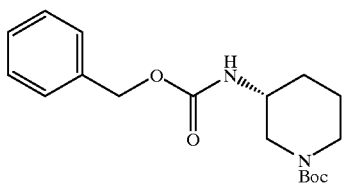

To a solution of the isocyanate prepared as in Example 10 Step F (85 ml, ~0.22 M) was added benzyl alcohol and the mixture was heated to reflux for 1 hr. The reaction mixture was cooled and concentrated to give crude product. Purification by flash chromatography (dichloromethane/ethyl acetate 3:1) gave the title compound (3.2 g , 9.6 mmol).

Step T:

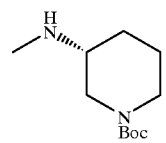

Potassium bis(trimethylsilyl)amide (1.5 eq) was added to the compound prepared in the previous step (1.85 g) in THF at 0° C. The mixture was stirred for 30 minutes and then iodomethane (2.0 eq) was added. The reaction was stirred for 3 hrs and then quenched with 1 N HCl. The aqueous layer was extracted with ethyl acetate (3×1 vol). The organic layer was washed with water and brine dried over MgSO₄, filtered and concentrated. Purification by flash chromatography (hexane/ethyl acetate 3:1) gave the methylated product (1.2 g). Hydrogenation with Pd/C under a hydrogen balloon provided the title compound (900 mg).

Step U:

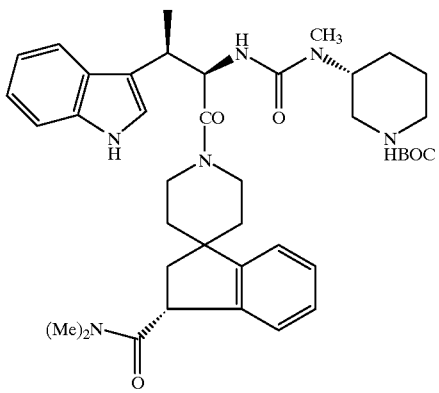

To the intermediate prepared in Step T (1.6 g, 7.47 mmol) in dichloromethane at −78° C. was added NMM (1.6 ml, 14.5 mmol) and phosgene (3.87 ml, 7.47 mmol). The reaction mixture was stirred for 1 hr at −78° C. and then for 10 minutes at 0° C. The intermediate from Step R above (3.6 g, 7.34 mmol) was added to the reaction mixture along with NMM (0.80 ml, 7.34 mmol). The mixture was stirred overnight and diluted with dichloromethane and washed with 1 N HCl, water, and brine. The organic layers were dried over $MgSO_4$, filtered and concentrated. Purification by flash chromatography (dichloromethane/acetone 3:1) gave the title compound (2.75 g, 4.10 mmol).

Step V:

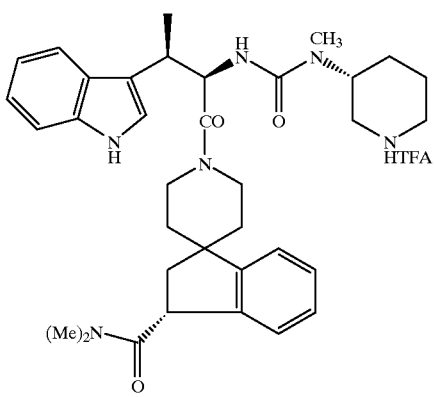

The title compound from the previous step (2.7 g, 4.10 mmol) was stirred in a 1:1 mixture of TFA/dichloromethane for 2 hrs. The solution was concentrated and azeotroped from toluene. Purification by prep HPLC (RP-18, $H_2O$ 1% TFA/$CH_3CN$ 1% TFA 70:30) gave the title compound after freeze drying (1.95 g, 2.85 mmol). Key 1H NMR (δ $CD_3OD$, 400 MHz, mixture of rotamers): 7.79 (d, 1/2 H), 7.63 (d, 1/2 H), 7.35–6.99 (m, 8 H), 5.86 (d, NH), 5.75 (d, NH), 5.23 (m, 1/2 H), 5.12 (m, 1/2 H), 4.59–4.47 (m, 2 H), 4.29–4.27 (m, 1 H), 4.08–4.00 (1/2 H), 3.80–3.75 (1/2 H), 3.68–3.59 (m, 1 H), 3.26 (s, 3/2 H), 3.16–3.03 (m, 2 H), 3.04 (s, 3/2 H), 3.01 (s, 3/2 H), 2.92–2.91 (m, 1 H)<2.84–2.80 (m, 1 H), 2.79 (s, 3/2 H), 2.66 (3/2 H), 2.64–2.56 (m, 1/2 H), 2.45–2.40 (m, 1/2 H), 2.16–1.97 (m, 3/2 H), 1.81 (dt, 1/2 H), 1.78–1.59 (m, 5 H), 1.51 (d, 3/2 H), 1.44 (d, 3/2 H), 1.20 (m, 1/2 H), 0.95 (dt, 1/2 H). FAB-MS: 599 (M+1).

EXAMPLE 19

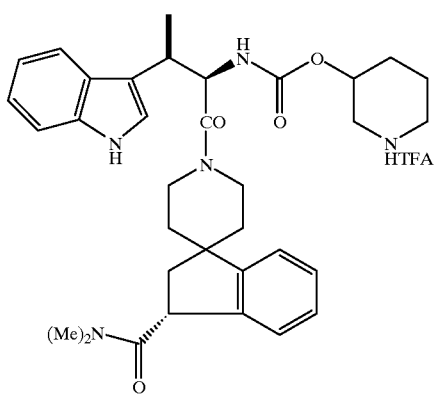

Step A:
Sodium cyanoborohydride (32 mg, 0.51 mmol) was added to a mixture of the title compound from Example 18 (110 mg, 0.17 mmol), formaldehyde (0.064 ml, 37% in $H_2O$) and sodium acetate (70 mg, 0.8 mmol) in methanol. The reaction mixture was stirred overnight and then concentrated. The residue was dissolved in 1 N NaOH and extracted with ethyl acetate. The ethyl acetate layers were concentrated and the residue was converted into the TFA salt with TFA in dichloromethane. Purification by MPLC ($LH_{20}$, methanol) gave the title compound (54 mg). ESI-MS: 599.3 (M+1).

EXAMPLE 20

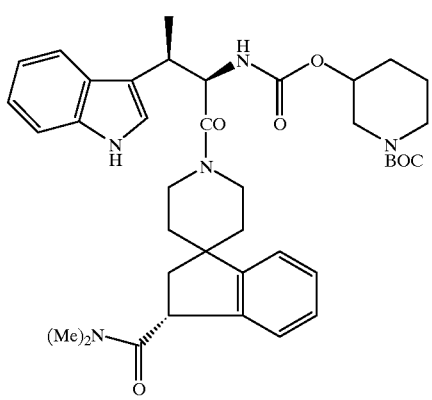

Step A:

CDI (20 mg, 0.12 mmol) was added to 3-hydroxy-Boc-piperidine (24.3 mg, 0.121 mmol) and NMM (0.039 ml, 0.36 mmol) in dichloromethane. The reaction mixture was stirred for 2 hrs and then the title compound from Example 18 Step R (60 mg) was added. The reaction mixture was stirred overnight and then loaded onto a flash column. Elution with-dichloromethane/ethyl acetate (1:1) gave the title compound (31 mg).

Step B:

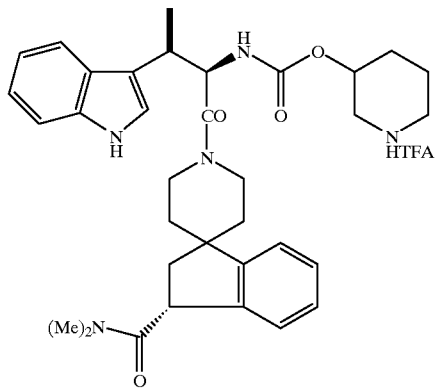

The title compound from the previous step was stirred in a mixture of TFA/dichloromethane for 1 hr and then concentrated. Purification by MPLC (LH$_{20}$, methanol) gave the title compound (22.3 mg). ESI-MS: 586 (M+1).

EXAMPLE 21

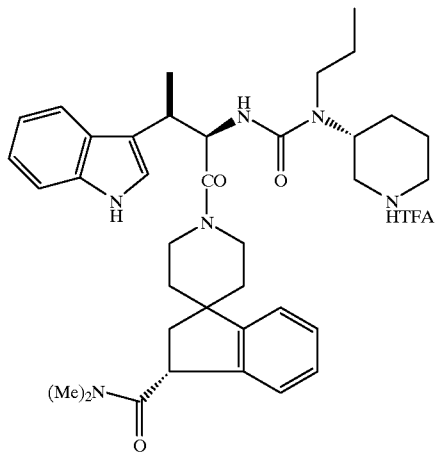

Step A:

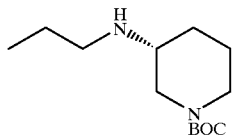

The title compound (52 mg) was prepared from the intermediate prepared in Example 18 Step S (200 mg) and allyl bromide according to the procedure described in Example 18 Step T.

Step B:

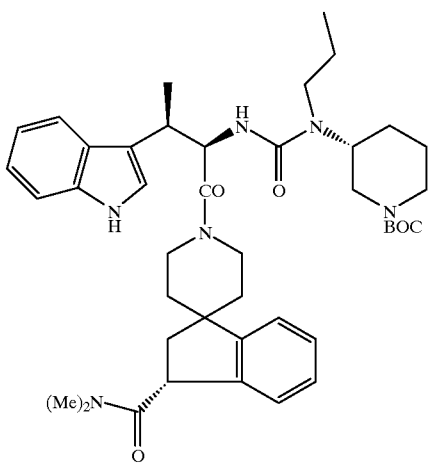

The title compound (27 mg) was prepared from the title compound (52 mg) of the previous step and the intermediate prepared in Example 18 Step R (100 mg).

Step C:

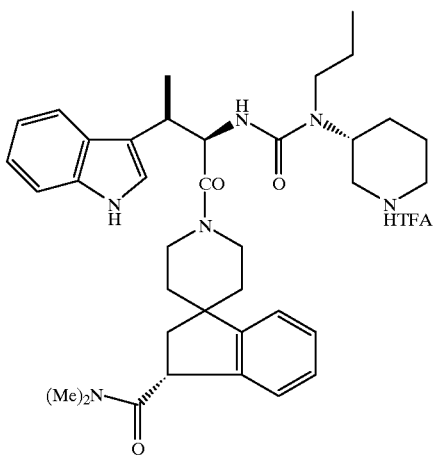

The title compound (12 mg) was prepared from the title compound (27 mg) of the previous step by treatment with TFA followed by MPLC purification (LH$_{20}$, methanol). Key $^1$H NMR (δ, CD$_3$OD, 400 MHz, mixture of rotamers): 3.28 (s, 3H), 3.05 (s, 3H), 1.5 (m, 3H), 0.79 (m, 3H). MS-FAB: 627.3 (M+1).

EXAMPLE 22

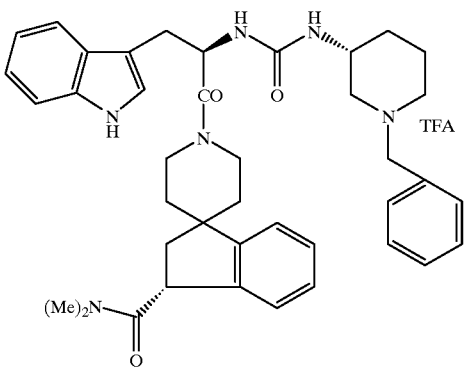

The title compound (27.8 mg) was prepared from the intermediate prepared in Example 10 Step H (80 mg) and benzaldehyde (0.6 ml) as in Example 19. Key $^1$H NMR (δ, CD$_3$OD, 400 MHz, mixture of rotamers): 4.30 (m, 2H), 3.22 (s, 3H), 3.00 (s, 3H), 0.90 (m, 2/3H), −0.08 (m, 2/3H). MS-FAB: 661.4 (M+1).

EXAMPLE 23

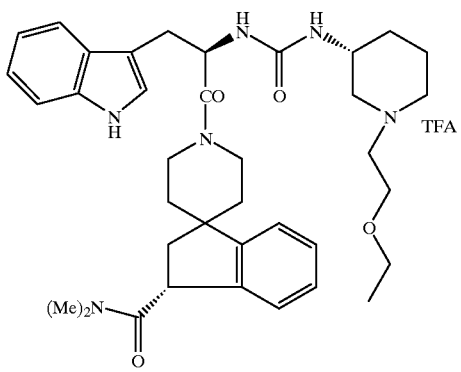

Step A:

To the title compound from Example 10 Step H (100 mg) in acetonitrile was added 2-bromo ethyl ether (0.02 ml) and triethylamine (0.041 ml). The reaction mixture was stirred overnight at room temperature and then for 3 hrs at 60° C. The reaction mixture was cooled and concentrated. Purification by flash chromatography (dichloromethane/methanol/ammonium hydroxide, 90:10:1) gave the amine which was treated with TFA in dichloromethane. MPLC purification (LH$_{20}$, methanol) gave the title compound (19.6 mg). FAB-MS: 643 (M+1).

EXAMPLE 24

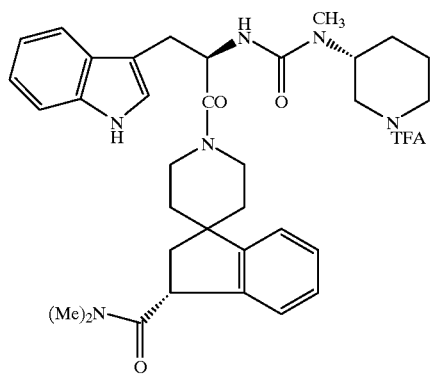

Step A:

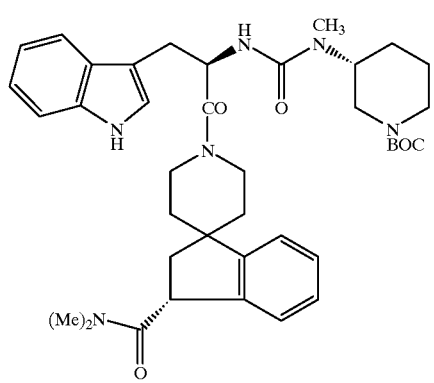

The title compound (50 mg) was prepared from the intermediate of Example 10 Step C (110 mg) and the intermediate from Example 18 Step T (55 mg) as in Example 18 Step U.

Step B:

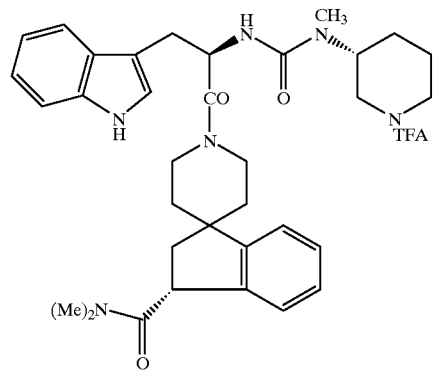

The title compound (39 mg) was prepared from the intermediate prepared in the previous step (50 mg) as in Example 10 Step H. Key $^1$H NMR (δ, CD$_3$OD, 400 MHz, mix of rotamers): 3.22 (s, 3H), 3.00 (s, 3H), 2.89 (s, 3H), 0.92 (m, 2/3H), −0.02 (m, 2/3H). MS-FAB: 585.2 (M+1).

EXAMPLE 25

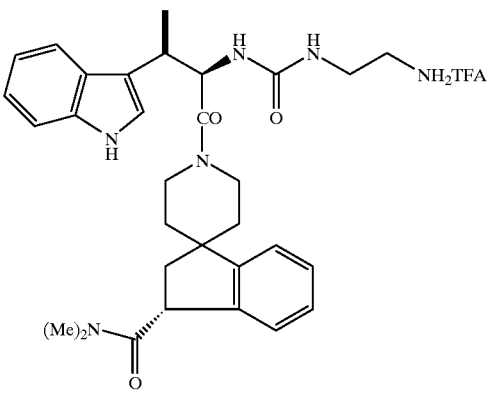

Step A:

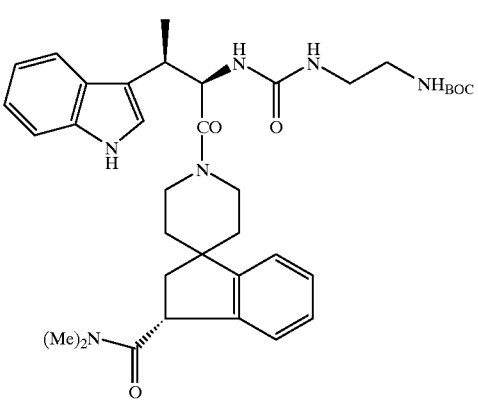

The title compound (49 mg) was prepared from the intermediate prepared in Example 18 Step R (80 mg, 0.16 mmol) and N-Boc-ethylene diamine (31 mg, 0.19 mmol) as in Example 12 Step A.

Step B:

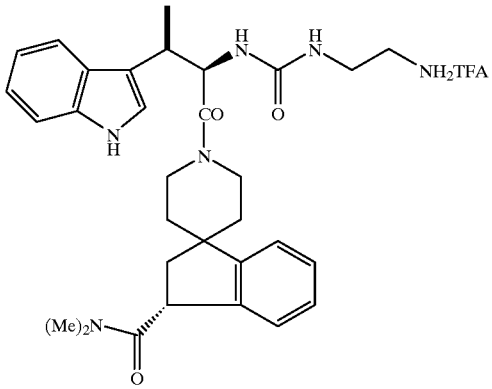

The title compound (39 mg) was prepared from the intermediate prepared in the previous step (49 mg) as in Example 10 Step H. Key $^1$H NMR ($\delta$, CD$_3$OD, 400 MHz, mix of rotamers): 3.25 (s, 3H), 3.05 (s, 3H), 1.50 (d, J=8.0 Hz, 3/2H), 1.41 (d, J=8.0 Hz, 3/2H), 1.08 (m, 1/2H), 0.69 (m, 1/2H). MS-FAB: 545.4 (M+1).

EXAMPLE 26

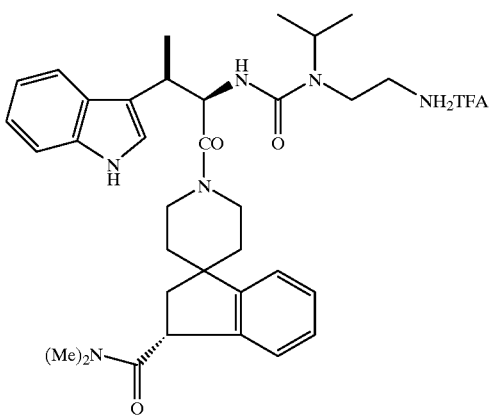

Step A:

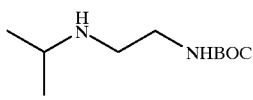

Sodium cyanoborohydride (0.41 g, 6.6 mmol) was added to a mixture of N-t-butoxycarbonyl-2-aminoethanal (0.71 g, 4.46 mmol), isopropyl amine (0.56 ml, 6.6 mmol), and sodium acetate (1.0 g, 13.3 mmol) in ethanol. The reaction mixture was stirred at room temperature overnight and then concentrated. The residue was dissolved in 1 N NaOH and extracted with ethyl acetate. The organic layers were washed with brine, dried over Na$_2$SO$_4$, filtered and concentrated. Purification by flash chromatography (dichloromethane/methamol/ammonia; 90:10:1) provided the title compound (463 mg) as an oil.

Step B:

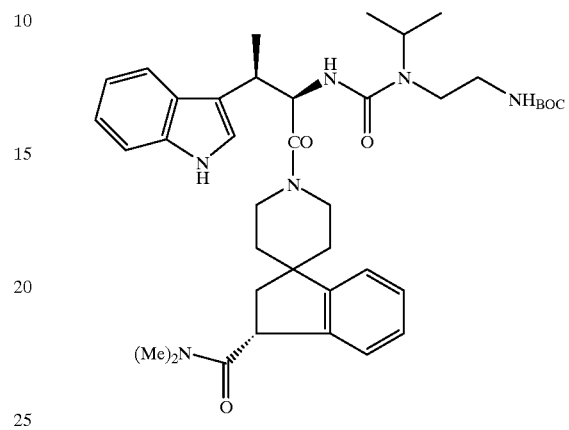

To a mixture of the intermediate from Example 18 Step R (250 mg, 0.5 mmol) and NMM (0.22 ml, 2.0 mmol) in dichloromethane at −78° C. was added phosgene (0.26 ml 0.5 mmol). The reaction mixture was stirred for 1 hr and then the intermediate from the previous step (0.112 g, 0.55 mmol) in dichloromethane was added. The mixture was allowed to warm to room temperature overnight. The reaction mixture was concentrated and loaded onto a Prep TLC plate. Prep TLC purification (dichlormethane/acetone, 4:1) gave the title compound (58 mg).

Step C:

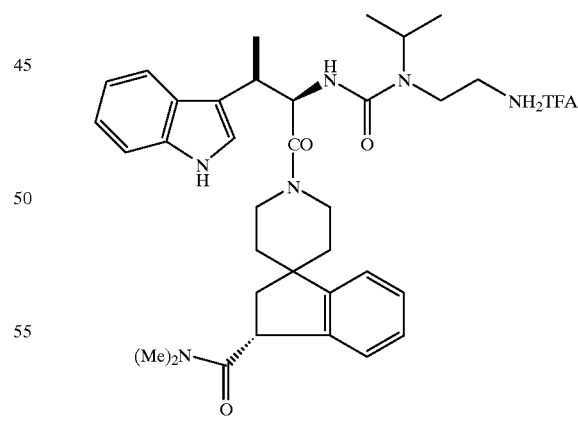

The title compound (47 mg) was obtained from the intermediate of the pervious step (58 mg) as in Example 10 Step H. Key $^1$H NMR ($\delta$, CD$_3$OD, 400 MHz, mix of rotamers): 3.30 (s, 3H), 3.02 (s, 3H), 1.52 (d, J=8.0 Hz, 3/2H), 1.45 (d, J=8.0 Hz, 3/2H), 1.10 (m, 3H), 1.00 (d, J=8.0 Hz, 3/2H), 0.90 (d, J=8.0 Hz, 3/2H). MS-FAB: 687.6 (M+1).

EXAMPLE 27

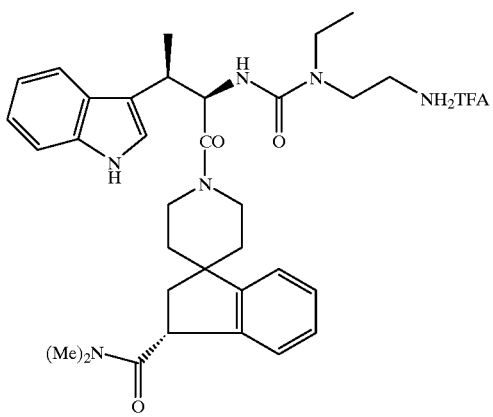

Step A:

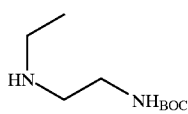

The title compound was prepared from ethylamine and N-t-butoxycarbonyl-2-aminoethanal as in Example 26 Step A.

Step B:

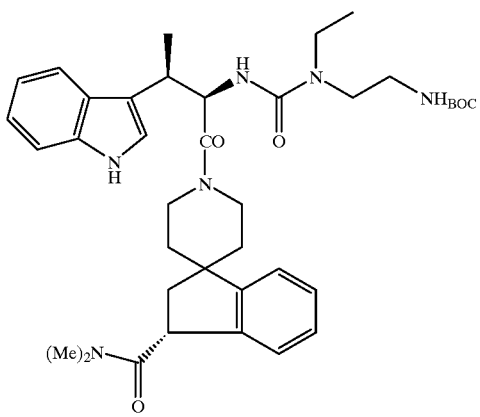

The title compound (59 mg) was prepared from the title compound of Example 18 Step R (99 mg, 0.2 mmol) and the intermediate from the previous step as in Experiment 170 Step B.

Step C:

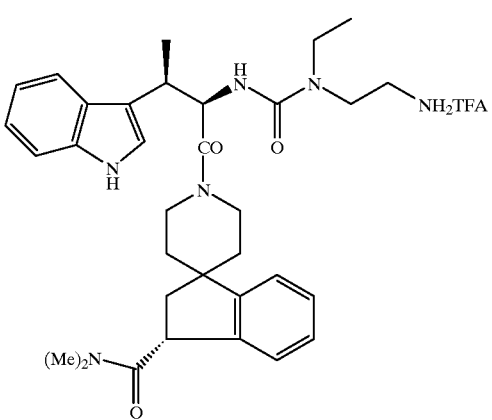

The title compound (38 mg) was prepared from the intermediate from the previous step (57 mg) as in Example 10 Step H. Key $^1$H NMR ($\delta$, CD$_3$OD, 400 MHz, 1:1 mixture of rotamers): 7.80–7.79 (m0, 7.64–7.62 (m0, 7.36–7.01 (m0, 5.18 (d), 5.06 (d), 4.61–4.47 (m), 3.63–3.58 (m), 3.05 (s), 3.01 (s), 1.52 (d), 1.46 (d), 1.3–1.2 (m), 0.99 (t), 0.92 (t).

EXAMPLE 28

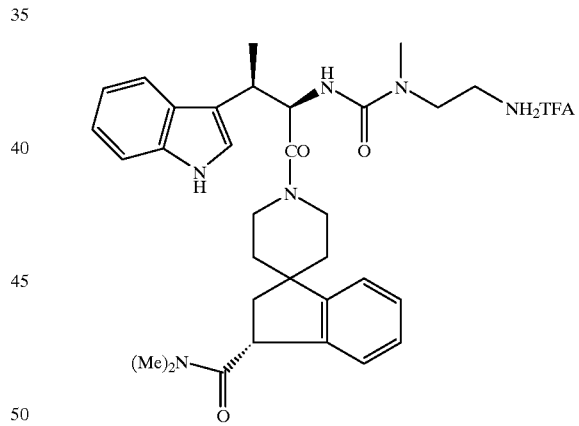

Step A:

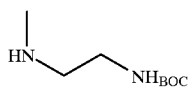

The title compound was prepared from methylamine and N-t-butoxycarbonyl-2-aminoethanal as in Example 26 Step A.

Step B:

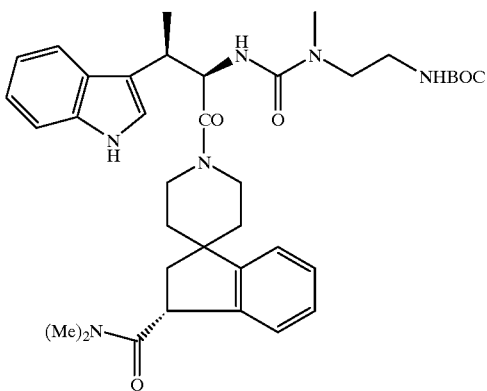

The title compound was prepared from the title compound of Example 18 Step R and the intermediate from the previous step as in Experiment 170 Step B.

Step C:

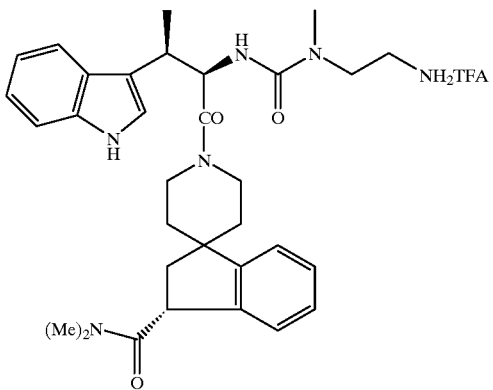

The title compound was prepared from the intermediate from the previous step as in Example 10 Step H. Key $^1$H NMR (δ, CD$_3$OD, 400 MHz, mix of rotamers): 3.40 (s, 3H), 3.05 (s, 3H), 2.90 (s, 3/2H), 2.85 (s, 3/2H), 1.55 (d, J=8.0 Hz, 3/2H), 1.47 (d, J=8.0 Hz, 3/2H). MS-FAB: 559.5 (M+1).

EXAMPLE 29

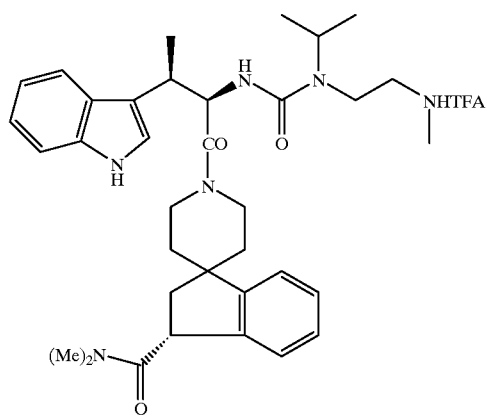

Step A:

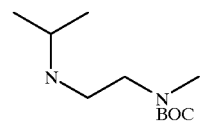

The title compound (120 mg) was prepared from N-t-butoxycarbonyl-2-methylaminoethanal (200 mg) and iso-propylamine (100 mg) according to the procedure described in Example 26 Step A.

Step B:

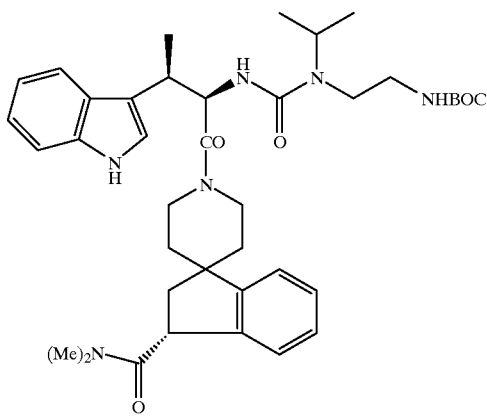

The title compound (57 mg) was prepared from the title compound of Example 18 Step R (150 mg, 0.3 mmol) and the intermediate from the previous step (73 mg, 0.36 mmol) as in Example 26 Step B.

Step C:

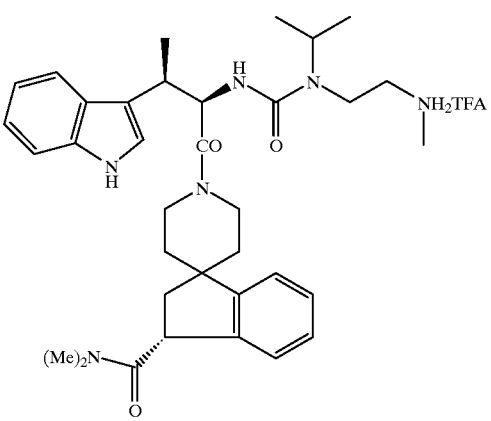

The title compound (40 mg) was prepared from the intermediate from the previous step (57 mg) as in Example 10 Step H. Key $^1$H NMR (δ, CD$_3$OD, 400 MHz, mix of rotamers): 3.31 (s, 3/2 H), 2.97 (s, 3/2 H), 3.05 (s, 3/2 H), 3.02 (s, 3/2 H), 2.62 (s, 3/2 H), 2.59 (s, 3/2 H), 1.53 (d, J=8.0 Hz, 3/2 H), 1.45 (d, J=8.0 Hz, 3/2 H), 1.12 (m, 3 H), 1.00 (d, J=8.0 Hz, 3/2 H), 0.90 (d, J=8.0 Hz, 3/2 H). MS-FAB: 601.3 (M+1).

EXAMPLE 30

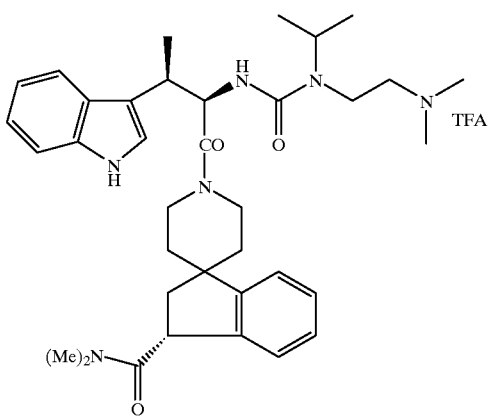

The title compound (9.6 mg) was prepared from the title compound from Example 26 Step C (25 mg) as in Example 19 Step A. Key $^1$H NMR (δ, CD$_3$OD, 400 MHz, mix of rotamers): 3.30 (m, 3 H), 3.00 (m, 3 H), 2.58 (m, 6H), 1.50 (m, 3/2 H), 1.42 (m, 3/2 H), 1.10 (m, 3 H), 1.00 (m, 3 H). MS-FAB: 615.4 (M+1).

EXAMPLE 31

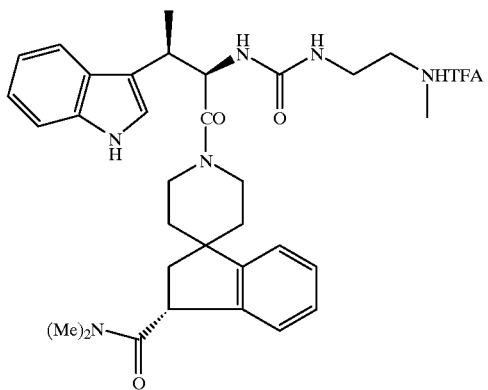

Step A:

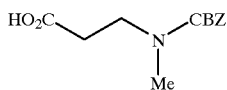

To a suspension of oil free NaH (144 mg) in THF (20 ml) was added CBZ-β-Ala-OMe (1.19 g) in THF (10 ml) slowly at room temperature. After stirring for 30 minutes MeI (0.37 ml) was added and then the mixture was stirred for another 30 minutes. The mixture was poured into water and extracted with ether, dried over sodium sulfate, filtered and concentrated. The mixture was purified by chromatatron (hexanes/ethyl acetate=6/1). To this residue in methanol was added 6 N NaOH and stirred for 30 minutes. The mixture was poured into water and extracted with ether. The organic layer was discarded. The aqueous layer was acidified with 6 N HCl to pH=1.0 and extracted with ether. The organic layer was washed with brine, dried over sodium sulfate, filtered and concentrated to give the desired product (603 mg).

Step B:

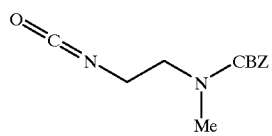

To the intermediate prepared from Step A (603 mg) in methylene chloride was added triethylamine (0.7 ml), and ethyl chloroformate (0.29 ml) at 0° C. After stirring for 1 the mixture was poured into 1N HCl and extracted with methylene chloride, dried over sodium sulfate, filtered and concentrated. To this residue in acetone (7 ml) was added sodium azide (812 mg) in water (7 ml) at room temperature. After 10 minutes, this mixture was poured into ether and washed with water and brine. The organic layer was dried over magnesium sulfate, filtered and concentrated. The residue was dissolved in 10 ml of toluene which was refluxed for 1 hour to give the isocyanate (0.25 N in toluene).

Step C:

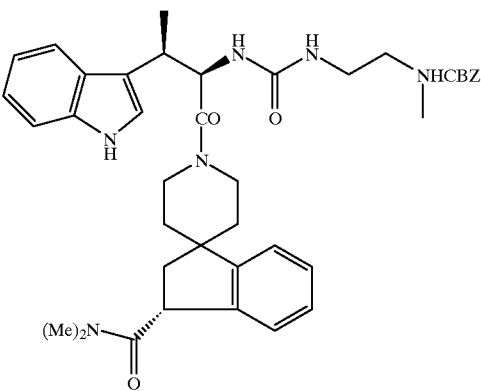

The title compound (37 mg) was prepared from the intermediate from the previous step and the intermediate from Example 18 Step R (38 mg).

Step D:

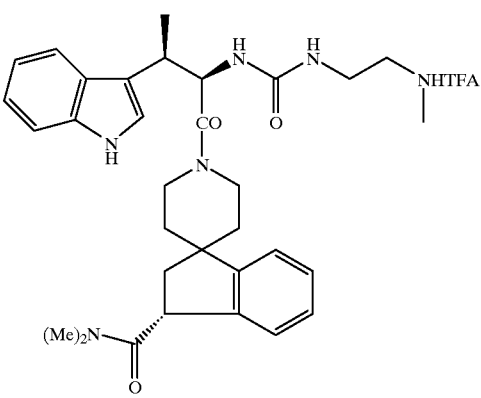

Hydrogenation of the intermediate (37 mg) from the previous step followed by salt formation with TFA and finally MPLC purification (LH$_{20}$, methanol) gave the title compound (17 mg). Key $^1$H NMR (δ, CD$_3$OD, 400 MHz, mix of rotamers): 3.30 (s, 3/2 H), 3.28 (s, 3/2 H), 3.04 (s, 3/2 H), 3.00 (s, 3/2 H), 2.68 (s, 3/2 H), 2.67 (s, 3/2 H), 1.50 (d, J=8.0 Hz, 3/2 H), 1.42 (d, J=8.0 Hz, 3/2H), 1.10 (m, 1/2 H), 0.70 (m, 1/2 H). MS-FAB: 559.5 (M+1).

EXAMPLE 32

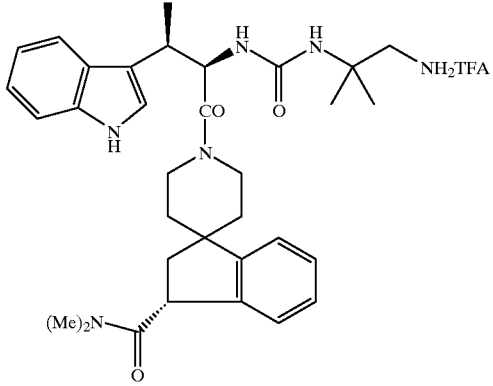

Step A:

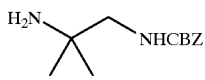

To a solution of the diamine (2.0 g, 22.7 mmol) in dichloromethane at 0° C. was added benzylchloroformate (3.24 ml, 22.7 mmol) and triethylamine 93.79 ml, 27.2 mmol). The reaction mixture was stirred overnight and then filtered and concentrated. Purification by flash chromatography (dichloromethane/methanol 9:1) gave the title compound (2.42 g).

Step B:

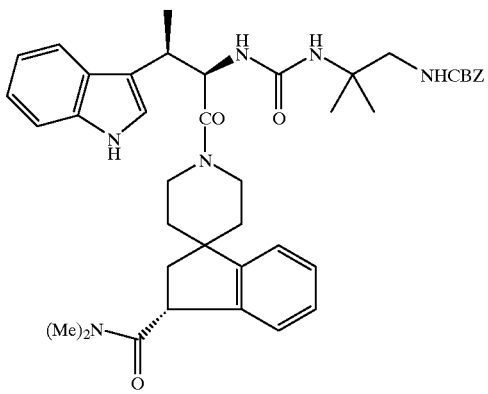

The title compound (63 mg) was prepared from the intermediate prepared in Example 18 Step R (80 mg, 0.16 mmol) and the product from the previous step (40 mg, 0.19 mmol) as in Example 12 Step A.

Step C:

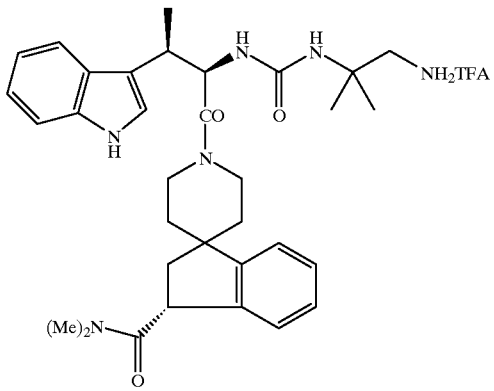

The title compound (20 mg) was prepared from the intermediate of the previous step (60 mg) according to the procedure described in Example 31 Step D. Key ¹H NMR (δ, CD₃OD, 400 MHz, mix of rotamers): 3.30 (s, 3/2 H), 3.25 (s, 3/2 H), 3.04 (s, 3/2 H), 3.00 (s, 3/2 H), 1.50 (d, J=8.0 Hz, 3/2 H), 1.40 (d, J=8.0 Hz, 3/2 H), 1.30 (m, 6 H). MS-FAB: 573.3 (M+1).

EXAMPLE 33

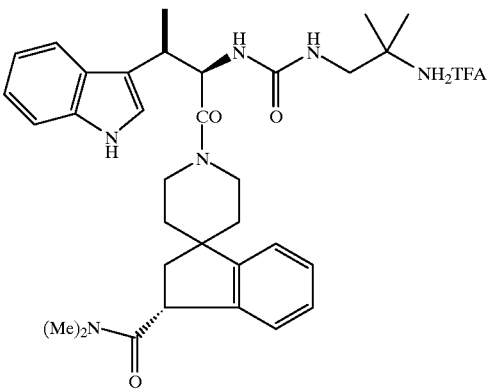

Step A:

To a solution of the intermediate prepared in Example 32 Step A (1.0 g, 4.76 mmol) and sodium hydroxide (0.76 g, 19 mmol) in isopropyl alcohol/water was added di-t-butyl dicarbonate (2.0 g, 9.5 mmol). The reaction mixture was stirred overnight and the isopropanol was removed. The aqueous layer was extracted with ethyl acetate. The organic layer was dried over MgSO₄, filtered and concentrated. The residue (0.96 g) was hydrogenated to give the title compound (0.54 g).

Step B:

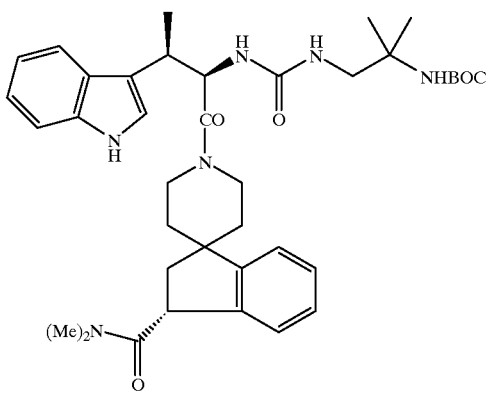

The title compound (58 mg) was prepared from the intermediate prepared in Example 18 Step R (80 mg, 0.16 mmol) and the product from the previous step (36 mg, 0.19 mmol) as in Example 12 Step A.

Step C:

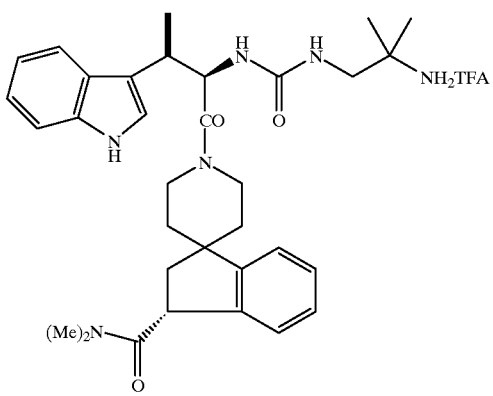

The title compound (41 mg) was prepared from the title compound from the previous step (58 mg) as in Example 10 Step H. Key $^1$H NMR (δ, CD$_3$OD, 400 MHz, mix of rotamers): 3.32 (s, 3/2 H), 3.25 (s, 3/2 H), 3.05 (s, 3/2 H), 3.02 (s, 3/2 H), 1.50 (d, J=8.0 Hz, 3/2 H), 1.41 (d, J=8.0 Hz, 3/2 H), 1.25 (m, 6H). MS-FAB: 573.2 (M+1).

EXAMPLE 34

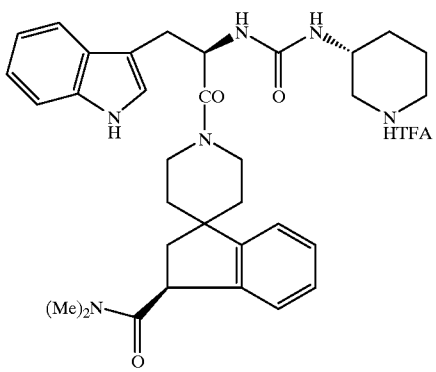

Step A:

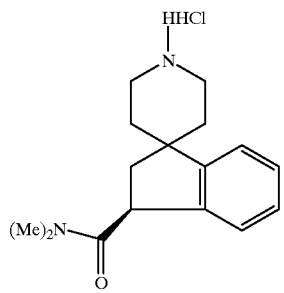

The title compound was prepared from the title compound from Example 83D Step A according to the procedure described in Example 10 Step A followed by removal of the Boc with ethyl acetate/HCl.

Step B:

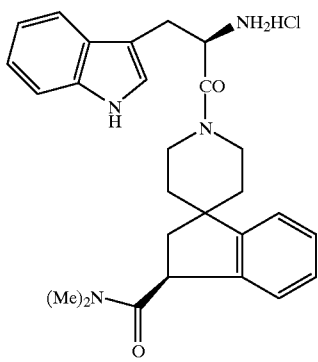

The title compound was prepared from the title compound of the previous step and the Boc-D-tryptophan according to the procedure described in Example 10 Step B followed by removal of the Boc with ethyl acetate/HCl.

Step C:

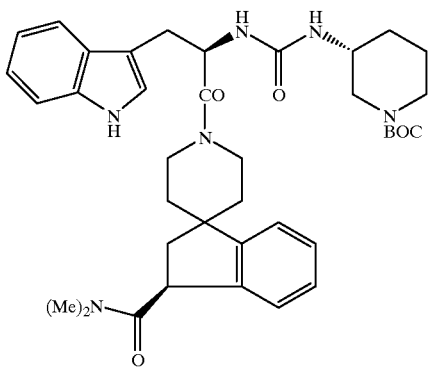

The title compound (38 mg) was prepared from the title compound of the previous step (69 mg) and the intermediate from Example 10 Step F (1.0 ml, 0.25 M toluene) according to the procedure described in Example 10 Step G.

Step D:

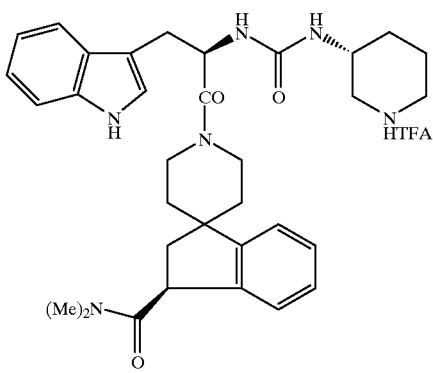

The title compound (29 mg) was prepared from the title compound (35 mg) of the previous example according to the procedure described in Example 10 Step H. Key ¹H NMR (δ, CD$_3$OD, 400 MHz, mix of rotamers): 3.22 (s, 3/3 H), 3.20 (s, 6/3 H), 3.02 (s, 3/3 H), 2.95 (s, 6/3 H), 1.00 (m, 2/3 H), 0.83 (m, 2/3 H), 0.30 (m, 2/3 H). MS-FAB: 571.3 (M+1).

EXAMPLE 35

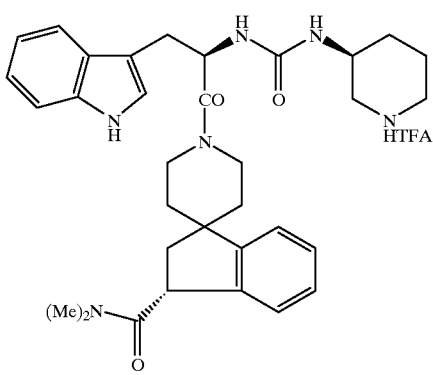

Step A:

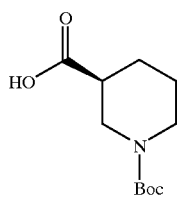

dl-N-Boc-nipecotic acid (14 g, 61 mmol) was dissolved in hot 9:1 ethyl acetate/methanol solution, (460 mL). While stirring the solution, R-(+)-α-methyl-benzylamine (1.0 eq) was added in one portion. Stirring was discontinued after 1 minute and the mixture allowed to cool slowly to room temperature for 16 h. The precipitated salt was filtered and recrystallized from 9:1 ethyl acetate/methanol solution (250 mL). This was also allowed to cool to room temperature over several hours. The resulting precipitate was filtered. The filtrate was crystallized a third time in the same manner (175 mL 9:1 EtOAc/CH$_3$OH). The filtrate was partitioned between ethyl acetate/1 N HCl, the phases separated and the aqueous portion extracted again with EtOAc. The combined organic portions were extracted once with 1 N HCl, water, washed with brine and dried over MgSO$_4$. The solvent was removed in vacuo to provide 9.90 g of the S-(−)-N-Boc-nipecotic acid. Rotation: [α]$_D$=−50.6°/methanol.

Step B:

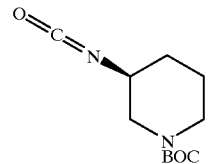

The isocyanate was prepared from the intermediate from the previous step and DPPA according to the procedure described in Example 10 Step F.

Step C:

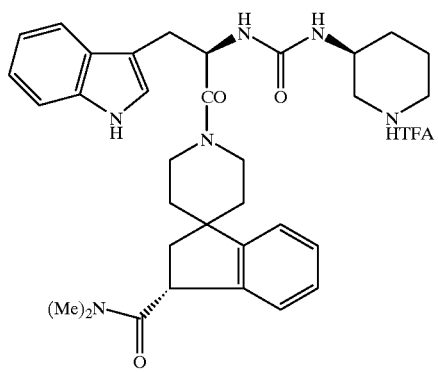

The title compound (80 mg) was prepared from the intermediate from Example 10 Step C (100 mg) and the compound from the previous step (1.0 ml, 0.25 M in toluene) as in Example 10 Step G.

Step D:

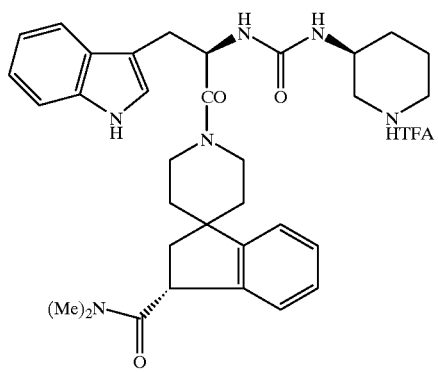

The title compound (66 mg) was prepared from the intermediate of the previous step (78 mg) as in Example 10 Step H. Key 1H NMR (δ, CD$_3$OD, 400 MHz, mix of rotamers): 3.25 (s, 3/3 H), 3.21 (s, 6/3 H), 3.02 (s, 3/3 H), 3.00 (s, 6/3 H), 0.90 (m, 2/3 H), −0.10 (m, 2/3 H). MS-FAB: 571.3 (M+1).

EXAMPLE 36

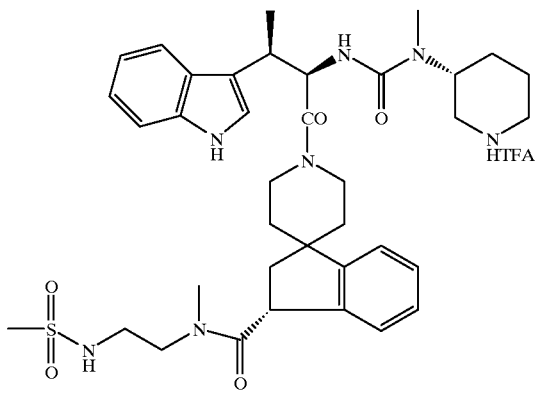

Step A:

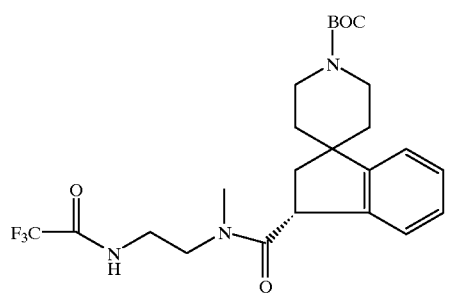

The title compound (458 mg) was prepared from the intermediate from Example 9, Step A (1.5 g) and N-trifluroacetamide-2-methylaminoethanediamine (910 mg) as in Example 10 Step A.

Step B:

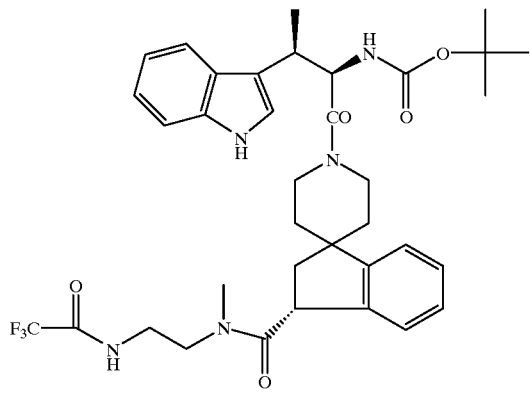

The title compound (450 mg) from the previous step was deprotected with ethyl acetate/HCl and then coupled to the intermediate from Example 18 Step P as in Example 18 Step Q to give the title compound (248 mg) as a white foam.

Step C:

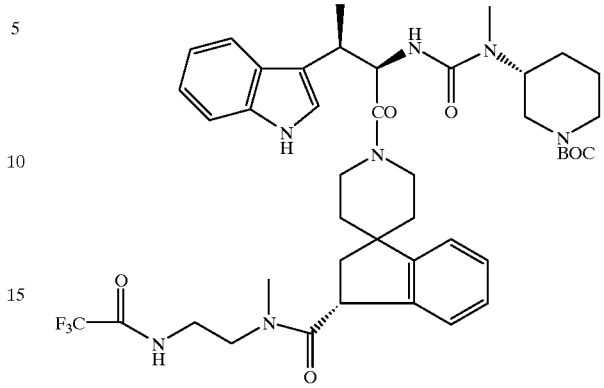

The title compound (242 mg) from the previous step was deprotected with ethyl acetate/HCl and then treated with phosgene (0.184 ml, 0.354 mmol) and NMM (0.155 ml, 1.41 mmol) at −78° C. The reaction mixture was stirred for 30 minutes at that temperature and then for 10 minutes at 0° C. The intermediate prepared in Example 18 Step T was added and the whole was stirred overnight. The reaction mixture was then poured into ethyl acetate and washed with 1 N HCl, water, and brine. The organic layers were dried over $MgSO_4$, filtered and concentrated. Purification by flash chromatography (dichloromethane/acetone 1:1) gave the title compound (138 mg).

Step D:

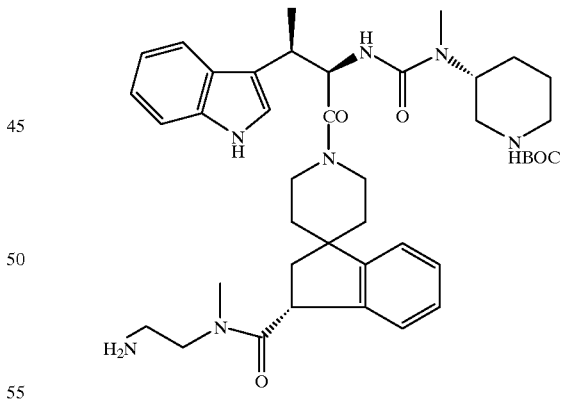

To a solution of the title compound from the previous step (130 mg) in methanol/$H_2O$ was added $K_2CO_3$. After 1 hr TLC analysis showed starting material was still present so ammonium hydroxide was added (2.0 ml) and the mixture was stirred for 1 hr. The mixture was concentrated and the residue was partitioned between dichloromethane and water. The organic layer was dried over $NaSO_4$, filtered, and concentrated to give the title compound (43 mg).

Step E:

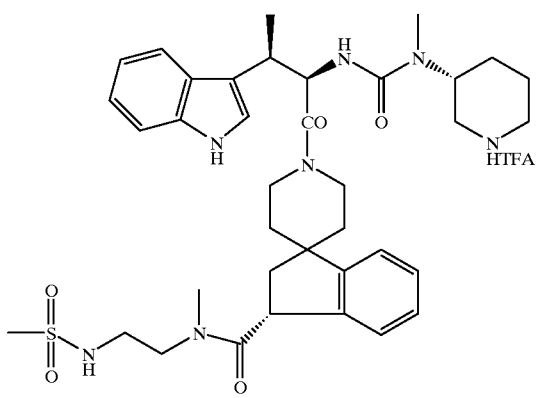

To a solution of the title compound from the previous step (28 mg, 0.035 mmol) in dichloromethane and NMM (0.004 ml, 0.038 mmol) at 0° C. was added mesyl chloride (0.003 ml, 0.038 mmol). The reaction mixture was stirred for 1 hr and then more mesyl chloride was added (0.003 ml). After stirring for 1 hr the solution was loaded onto a flash column. Elution (dichloromethane/acetone 3:2) gave the Boc protected title compound (23 mg). This material was dissolved in TFA/dichloromethane (1:1) and the solution was stirred for 1 hr. Concentration followed by MPLC purification (LH$_{20}$, methanol) gave the title compound (19.8 mg). Key $^1$H NMR (δ, CD$_3$OD, 400 MHz, mix of rotamers): 7.80–7.78 (m), 7.62 (d), 7.34–6.99 (m), 5.24–5.19 (m), 5.10–5.07 (m), 3.04 (s), 3.01 (s), 2.98 (s), 2.95 (s), 2.92 (m), 2.73 (m), 2.67 (m), 1.50 (d), 1.44 (d), 0.96–0.92 (m). Fab-MS; 706 (M+1).

EXAMPLE 37

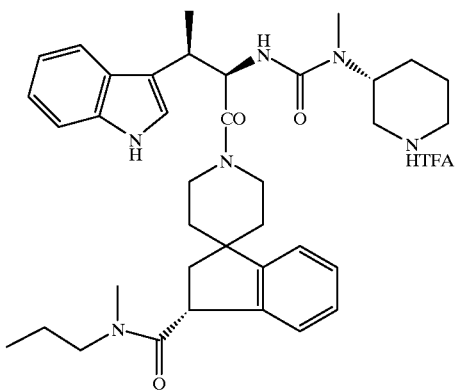

Step A:

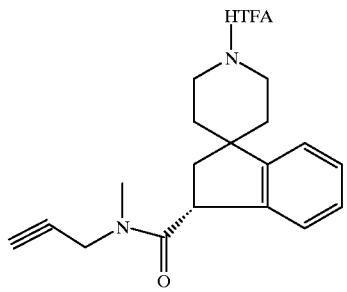

The title compound was prepared from the intermediate from Example 83 E Step A (600 mg, 1.81 mmol) and methyl propargyl amine as in Example 10 Step A, followed by treatment with TFA/dichloromethane.

Step B:

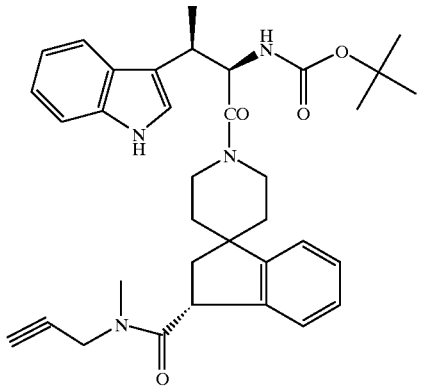

The title compound (382 mg) was prepared from the intermediate from above and the title compound from Example 18 Step P as in Example 18 Step Q.

Step C:

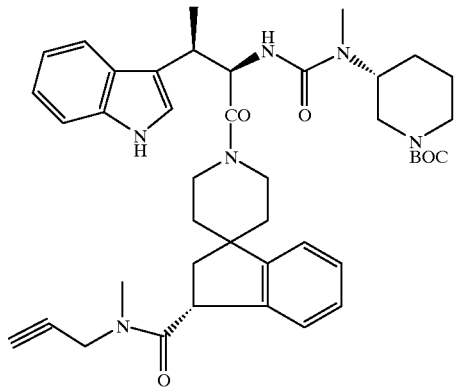

The title compound (370 mg) was deprotected with TFA/dichloromethane and the residue was reacted with the intermediate from Example 18 Step T as in Example 36 Step C to give the title compound (160 mg).

Step D:

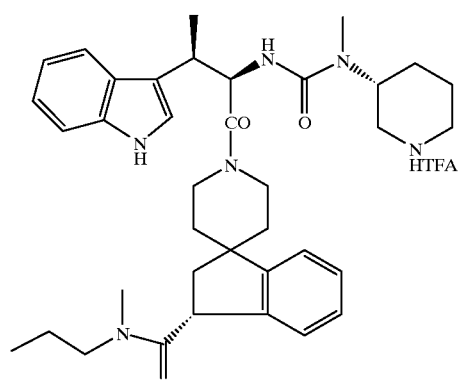

Hydrogenation of the intermediate (21 mg) from above over Pd/C for 3 hrs followed by stirring with TFA/dichloromethane gave the title compound (12 mg). Key ¹H NMR (δ, CD₃OD, 400 MHz, mixture of rotamers): 7.8 (d), 7.65 (d), 7.45–7.0 (m), 5.25–5.2 (m), 5.18–5.08 (m), 4.6–4.45 (m), 3.21 (s), 2.9 (s), 2.75 (s), 2.6 (s), 1.5 (d), 1.45 (d), 1.0–0.8 (m). Fab-MS; 627 (M+1).

EXAMPLE 38

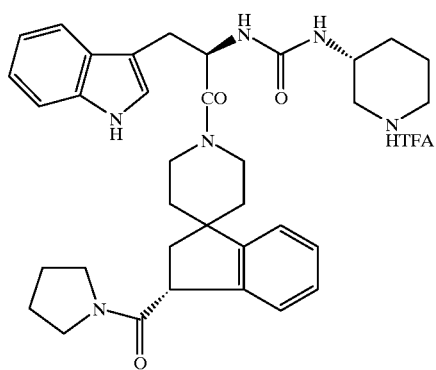

Step A:

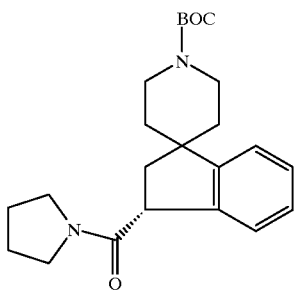

The title compound (542 mg) Was prepared from the intermediate from Example 9 Step A (500 mg, 1.51 mmol) and pyrrolidine (0.14 ml, 1.66 mmol) according to the procedure described in Example 10 Step A.

Step B:

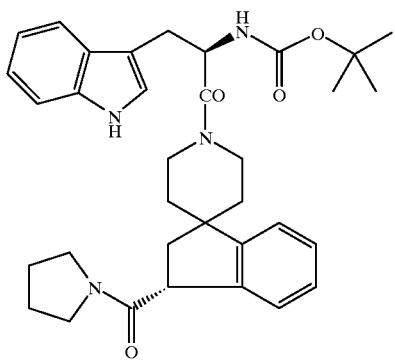

The title compound (100 mg) from the previous step was deprotected with ethyl acetate/HCl and the residue was reacted with Boc-D-tryptophan (95 mg) as in Example 10 Step B to give the title compound (58 mg).

Step C:

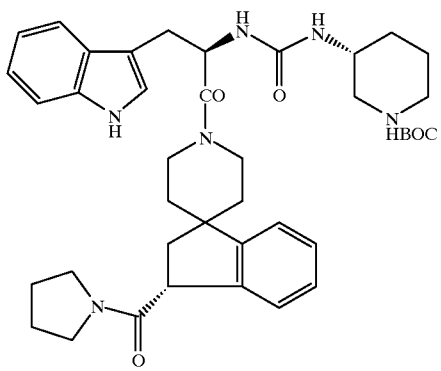

The title compound (56 mg) from the previous step was deprotected with ethyl acetate/HCl and the residue was reacted with the intermediate from Example 10 Step F as in Example 10 Step G to give the title compound (58 mg).

Step D:

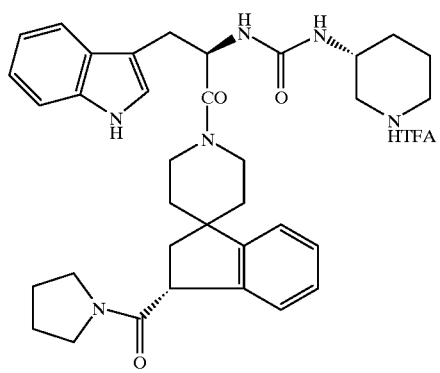

The title compound (39 mg) was prepared from the title compound of the previous step (47 mg) as in Example 10 Step H. Key ¹H NMR (δ, CD₃OD, 400 MHz, mix of rotamers): 5.14 (m, 2/3 H), 5.05 (m, 1/3 H), 2.00 (m, 6 H), 0.88 (m, 2/3 H), −0.10 (m, 2/3 H). MS-FAB: 597.3 (M+1).

EXAMPLE 39

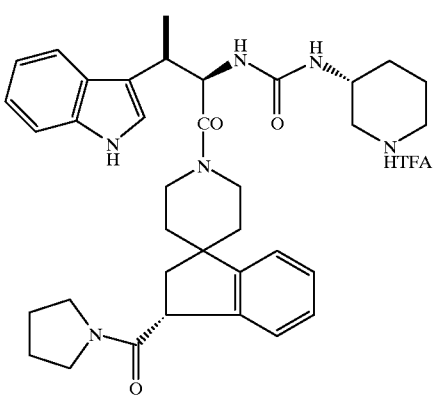

Step A:

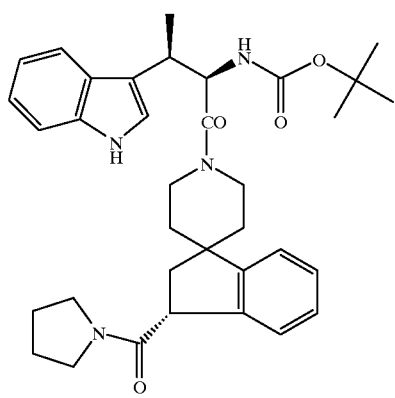

The title compound (262 mg) was prepared from the intermediate from Example 38 Step A (150 mg) and (R,R)-β-methyltryptophan as in Example 38 Step B.

Step B:

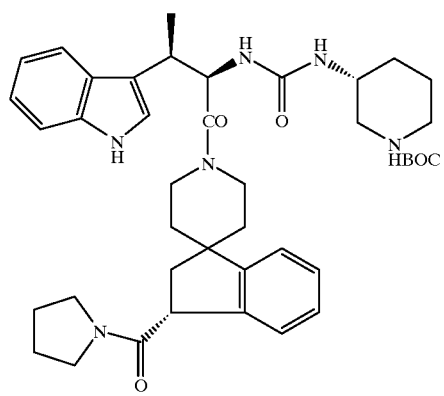

The title compound (100 mg) from the previous step was deprotected with ethyl acetate/HCl and the residue was reacted with the intermediate from Example 10 Step F as in Example 10 Step G to give the title compound (100 mg).

Step C:

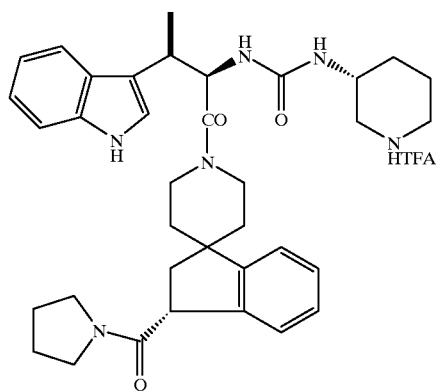

The title compound (76 mg) was prepared from the title compound of the previous step (100 mg) as in Example 10 Step H. Key $^1$H NMR (δ, CD$_3$OD, 400 MHz, mix of rotamers): 5.28 (m, 1/2 H), 5.12 (m, 1/2 H), 2.00 (m, 6 H), 1.50 (d, J=8.0 Hz, 3/2 H), 1.42 (d, J=8.0 Hz, 3/2 H), 1.07 (m, 1/2 H), 0.68 (m, 1/2 H). MS-FAB: 611.3 (M+1).

EXAMPLE 40

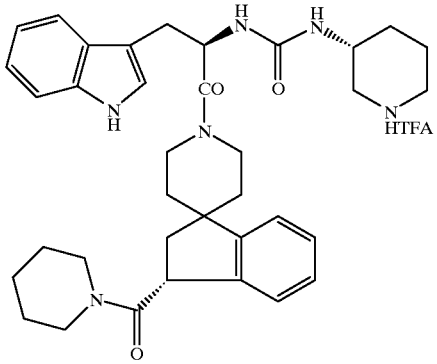

Step A:

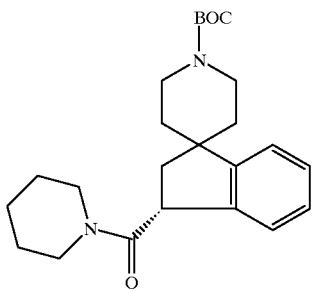

The title compound (236 mg) was prepared from the intermediate from Example 9 Step A (200 mg) and piperidine (0.06 ml) according to the procedure described in Example 10 Step A.

Step B:

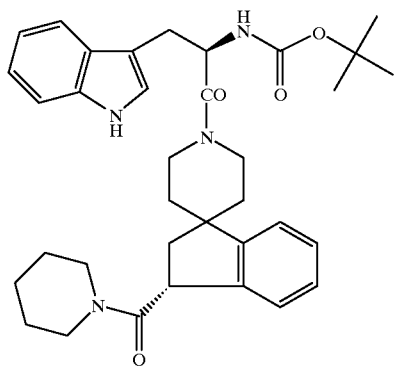

The title compound (200 mg) from the previous step was deprotected with ethyl acetate/HCl and the residue was reacted with Boc-D-tryptophan (180 mg) as in Example 10 Step B to give the title compound (160 mg).

Step C:

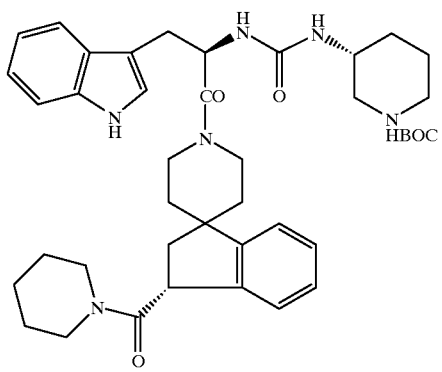

The title compound (80 mg) from the previous step was deprotected with ethyl acetate/HCl and the residue was reacted with the intermediate from Example 10 Step F as in Example 10 Step G to give the title compound (63 mg).

Step D:

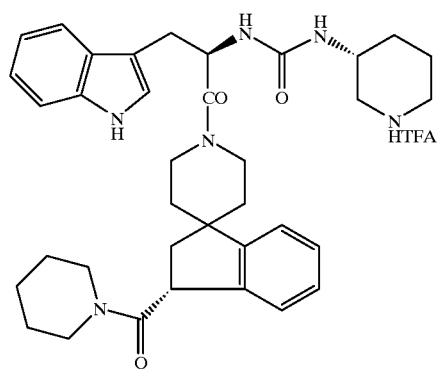

The title compound (47 mg) was prepared from the title compound of the previous step (62 mg) as in Example 10 Step H. Key $^1$H NMR (δ, CD$_3$OD, 400 MHz, mix of rotamers): 5.15 (m, 2/3 H), 5.05 (m, 1/3 H), 2.00 (m, 2 H), 1.70 (m, 6 H), 0.90 (m, 2/3 H), −0.08 (m, 2/3 H). MS-FAB: 611.4 (M+1).

EXAMPLE 41

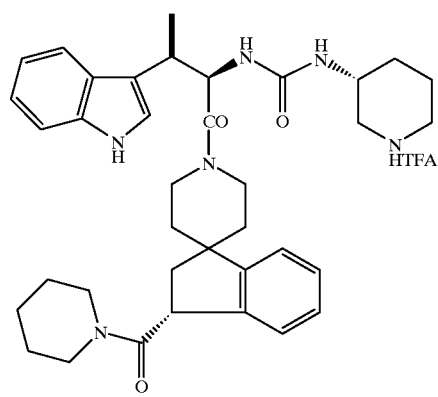

Step A:

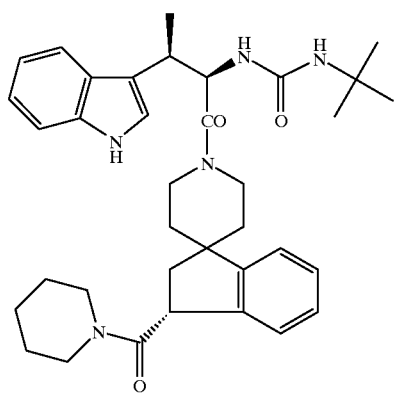

The title compound from Example 40 Step A was deprotected with ethyl acetate/HCl and the residue was reacted with the intermediate from Example 18 Step P as in Example 18 Step Q to give the title compound.

Step B:

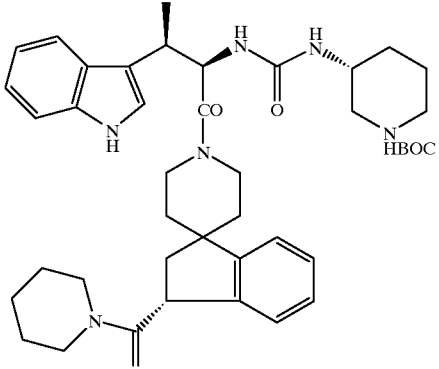

The title compound (80 mg) from the previous step was deprotected with ethyl acetate/HCl and the residue was reacted with the intermediate from Example 10 Step F as in Example 10 Step G to give the title compound (80 mg).

Step C:

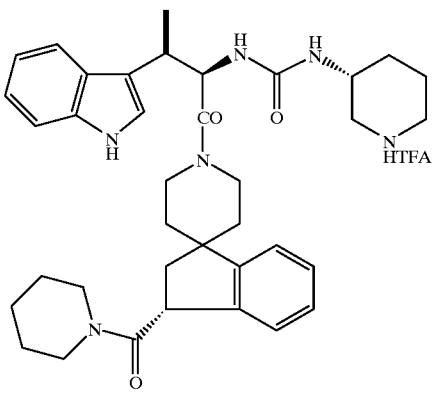

The title compound (60 mg) was prepared from the title compound of the previous step (80 mg) as in Example 10 Step H. Key $^1$H NMR (δ, CD$_3$OD, 400 MHz, mix of rotamers): 5.28 (m, 1/2 H), 5.12 (m, 1/2 H), 2.00 (m, 2 H), 1.65 (m, 6 H), 1.48 (d, J=8.0 Hz, 3/2 H), 1.41 (d, J=8.0 Hz, 3/2 H), 1.10 (m, 1/2 H), 0.70 (m, 1/2 H). MS-FAB: 625.5 (M+1).

EXAMPLE 42

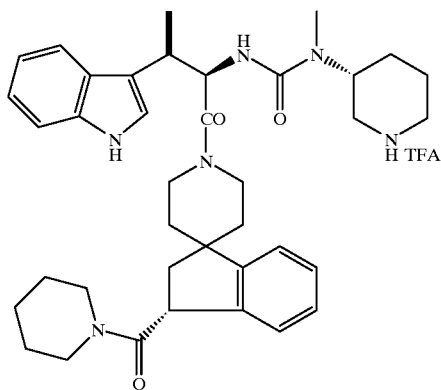

Step A:

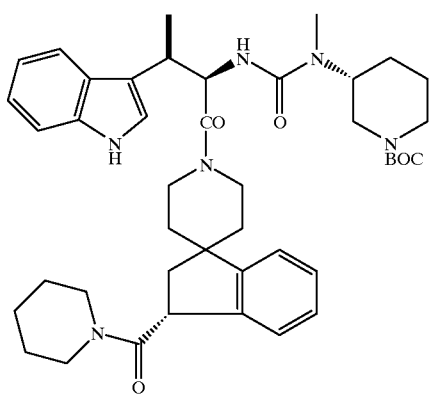

The title compound from Example 41 Step A was deprotected with ethyl acetate/HCl and the residue was reacted with the intermediate from Example 18 Step T as in Example 18 Step U to give the title compound.

Step B:

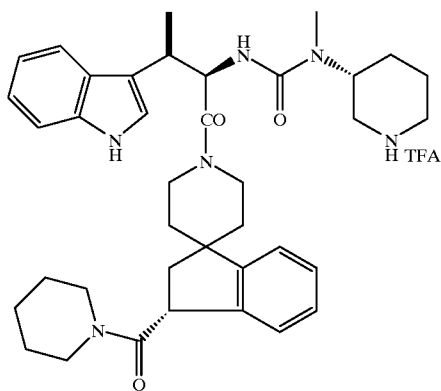

The title compound (91 mg) was prepared from the title compound of the previous step (120 mg) as in Example 10 Step H. Key $^1$H NMR ($\delta$, CD$_3$OD, 400 MHz, mix of rotamers): 5.22 (m, 1/2 H), 5.10 (m, 1/2 H), 2.75 (s, 3/2 H), 2.68 (s, 3/2 H), 2.00 (m, 2 H), 1.70 (m, 6 H), 1.50 (d, J=8.0 Hz, 3/2 H), 1.45 (d, J=8.0 Hz, 3/2 H), 1.22 (m, 1/2 H), 0.95 (m, 1/2 H). MS-FAB: 639.4 (M+1).

EXAMPLE 43

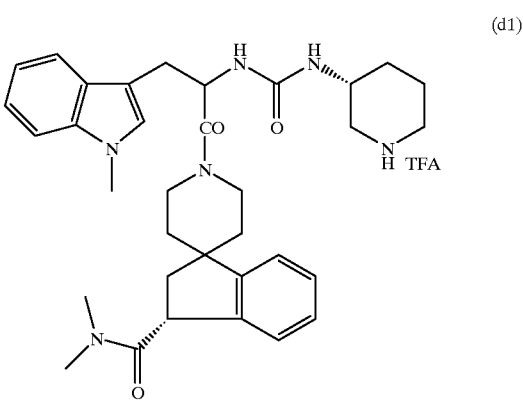

(d1)

Step A:

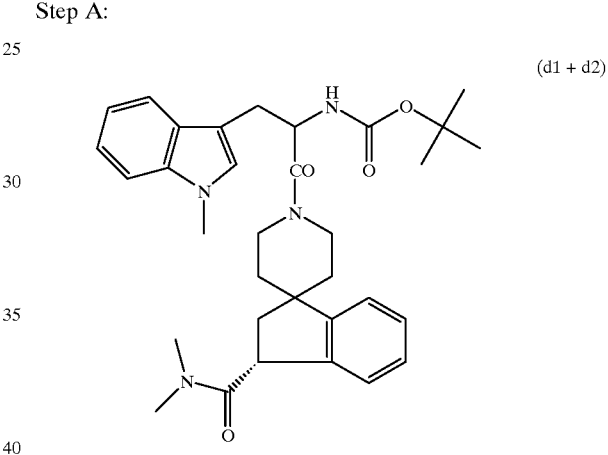

(d1 + d2)

The title compound was prepared from the title compound from Example 10 Step A and Boc-1-methyltryptophan as in Example 10 Step B.

Step B:

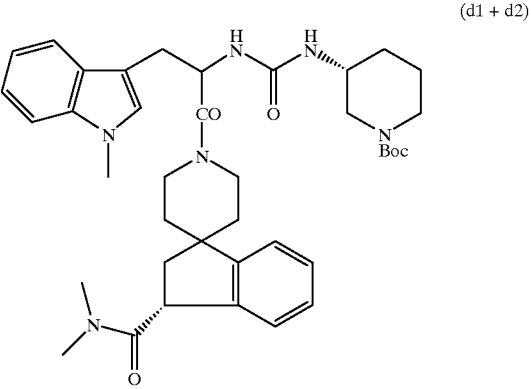

(d1 + d2)

The intermediate from the previous step was deprotected with ethyl acetate/HCl and the residue was treated with the isocyanate from Example 10 Step F to give the title compound d1 (60 mg) and d2 (54 mg).

Step C:

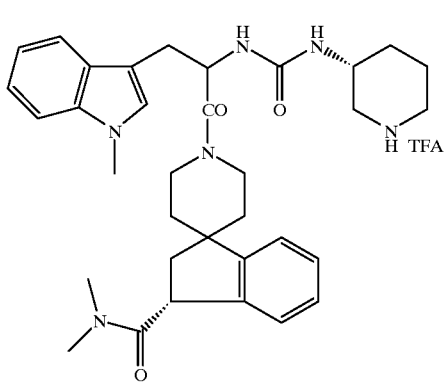
(d1)

The title compound (55 mg) was prepared from the intermediate above (d1, 60 mg) as in Example 10 Step H. Key ¹H NMR (δ, CD₃OD, 400 MHz, mix of rotamers): 5.10 (m, 2/3 H), 5.05 (m, 1/3H), 3.78 (s, 3/3 H), 3.75 (s, 6/3 H), 3.28 (s, 3/3 H), 3.20 (s, 6/3 H), 3.03 (s, 3/3 H), 2.98 (s, 6/3 H), 0.99 (m, 2/3 H), 0.00 (m, 2/3 H). MS-FAB: 585.4 (M+1).

EXAMPLE 44

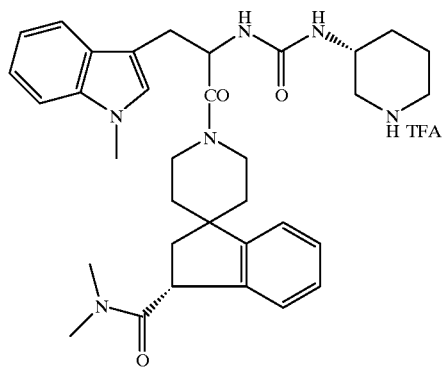
(d2)

Step A:
The title compound (49 mg) was prepared from the intermediate above (d2, 52 mg) as in Example 10 Step H. Key ¹H NMR (δ, CD₃OD, 400 MHz, mix of rotamers): 5.15 (m, 2/3 H), 5.06 (m, 1/3 H), 3.81 (s, 6/3 H), 3.76 (s, 3/3 H), 3.22 (s, 3/3 H), 3.21 (s, 6/3 H), 3.04 (s, 3/3 H), 2.99 (s, 6/3 H), 0.81 (m, 2/3 H), 0.35 (m, 2/3 H). MS-FAB: 585.4 (M+1).

EXAMPLE 45

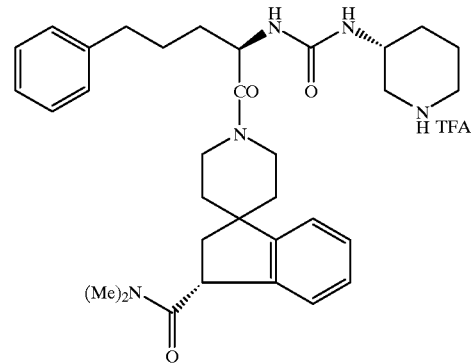

Step A:

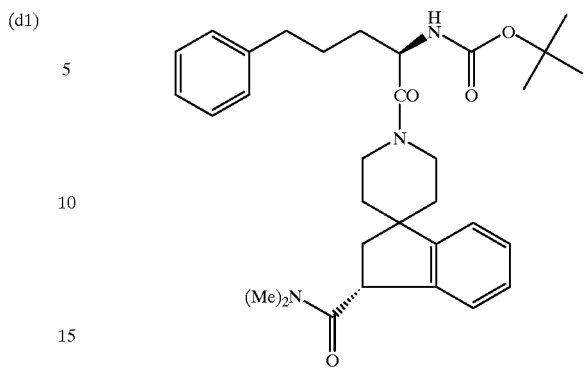

The title compound was prepared from the intermediate from Example 10 Step A and (2R)-N-t-Boc-5-phenylpentanoic acid as in Example 10 Step B.

Step B:

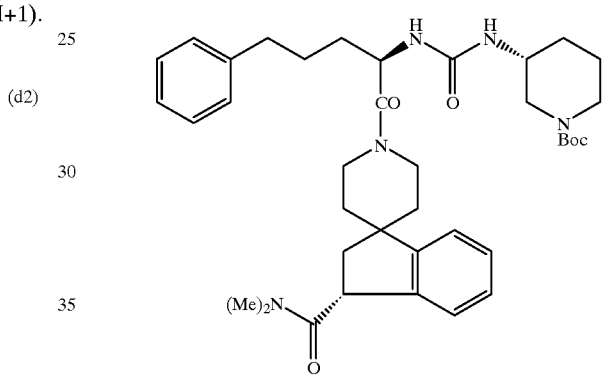

The intermediate from the previous step was deprotected with ethyl acetate/HCl and the residue was treated with the isocyanate from Example 10 Step F to give the title compound.

Step C:

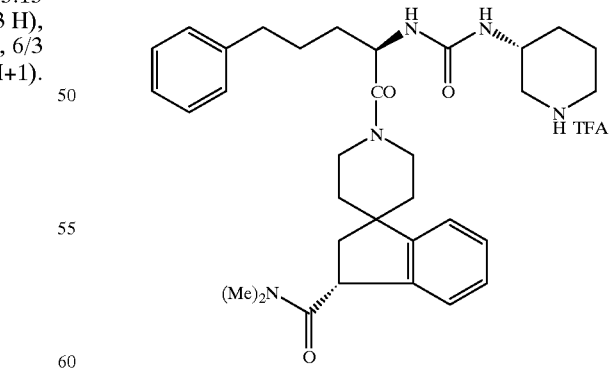

The title compound (33 mg) was prepared from the intermediate above (36 mg) as in Example 10 Step H. Key ¹H NMR (δ, CD₃OD, 400 MHz, mix of rotamers): 4.78 (m, 1/2 H), 4.70 (m, 1/2 H), 3.33 (s, 3/2 H), 3.31 (s, 3/2 H), 3.04 (s, 3/2 H), 3.02 (s, 3/2 H). MS-FAB: 560.2 (M+1).

EXAMPLE 46

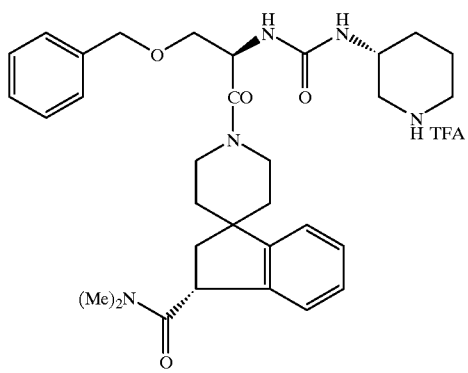

Step A:

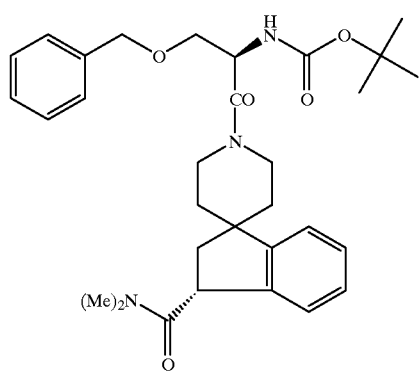

The title compound was prepared from the intermediate from Example 10 Step A and Boc-D-O-benzylserine as in Example 10 Step B.

Step B:

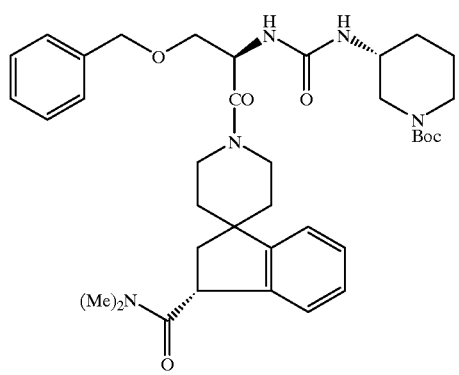

The intermediate from the previous step was deprotected with ethyl acetate/HCl and the residue was treated with the isocyanate from Example 10 Step F to give the title compound.

Step C:

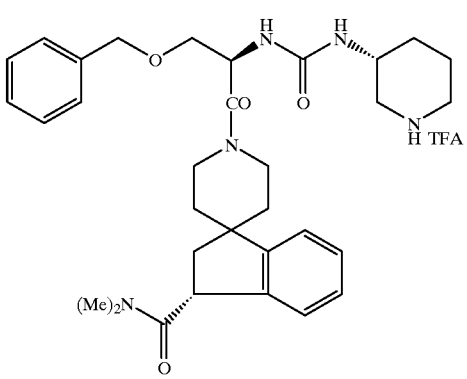

The title compound was prepared from the intermediate above as in Example 10 Step H. ESI-MS; 562 (M+1).

EXAMPLE 47

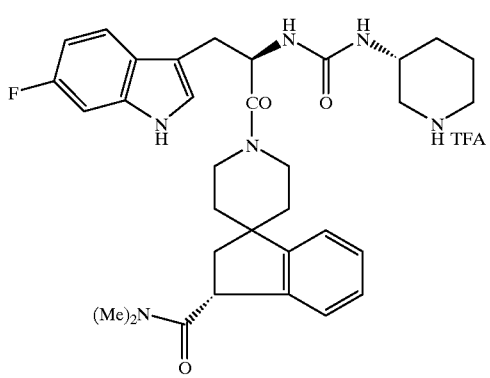

Step A:

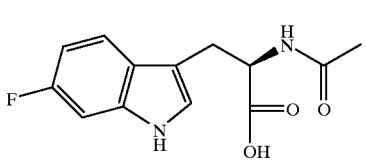

To a solution of 6-flurotrytophan (2.0 g, 7.5 mmol) in ethyl acetate (30 ml) was added R-methylbenzylamine (0.97 ml, 7.5 mmol). Ethanol (~20 ml) was added to dissolve the gel like salt. The solution was stored in a freezer overnight and the crystals that had formed were then filtered and washed with ethyl acetate. The crystals were then redissolved in ethyl acetate (20 ml)/ethanol (1 ml) and stored in a freezer for 5 hrs. The crystals were filtered and washed with ethyl acetate. The free acid (0.79 g) was obtained by suspending the salt in ethyl acetate and washing with 1 N HCl.

Step B:

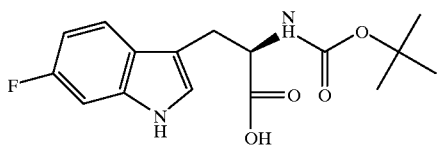

The intermediate from the previous step was dissolved in 1 N HCl (50 ml) and the solution was heated to reflux for 20 hrs. The solution was cooled to room temperature and brought to ~pH 11 with KOH. A solution of di-t-butyl-dicarbonate in isopropanol was added and the mixture was stirred for 8 h. The aqueous was extracted with hexane and then the pH was adjusted to 3. The resulting slurry was extracted with ethyl acetate and the ethyl acetate layers were washed with brine and dried over Na$_2$SO$_4$. The title compound (860 mg) was obtained as a white solid.

Step C:

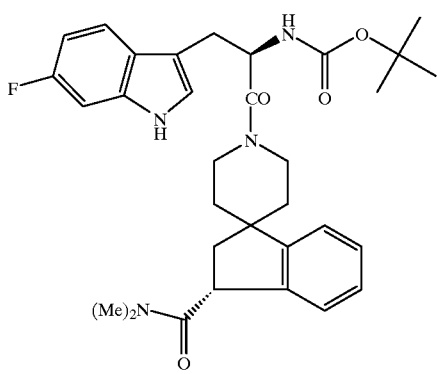

The title compound was prepared from the intermediate from Example 10 Step A and the intermediate from the previous step as in Example 10 Step B.

Step D:

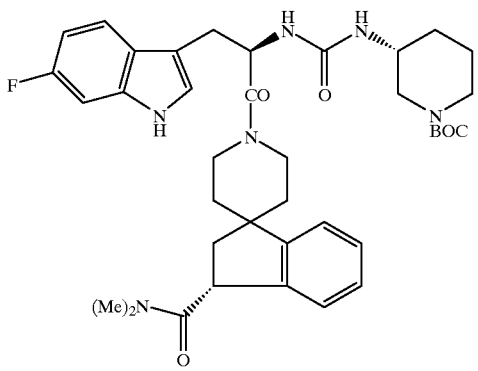

The intermediate from the previous step was deprotected with ethyl acetate/HCl and the residue was treated with the isocyanate from Example 10 Step F to give the title compound.

Step E:

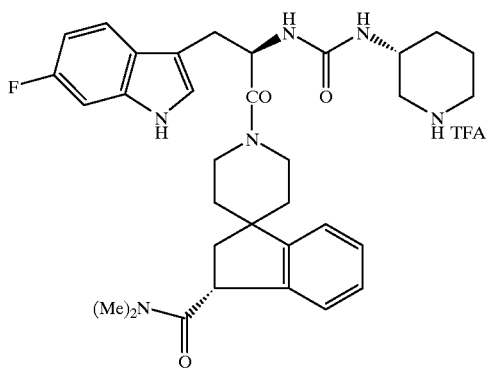

The title compound was prepared from the intermediate above as in Example 10 Step H. Key $^1$H NMR (δ, CD$_3$OD, 400 MHz, mix of rotamers): 5.10 (m, 2/3 H), 5.04 (m, 1/3 H), 3.26 (s, 3/3 H), 3.21 (s, 6/3 H), 3.03 (s, 3/3 H), 2.98 (s, 6/3 H), 0.99 (m, 2/3 H), −0.02 (m, 2/3 H). MS-FAB: 589.3 (M+1).

EXAMPLE 48

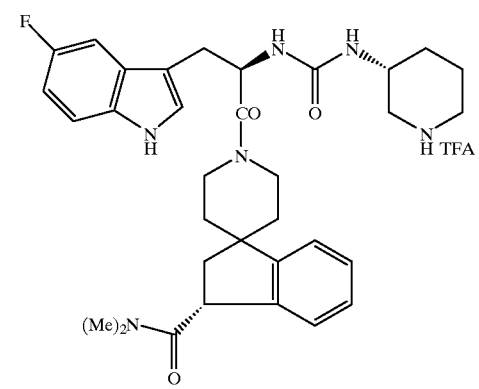

Step A:

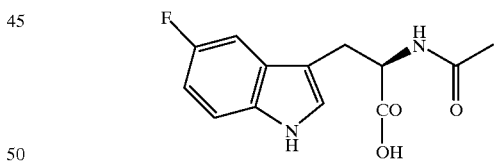

The title compound was obtained from 5-flurotryptophan and R-methyl benzylamine according to the procedure of Example 47 Step A.

Step B:

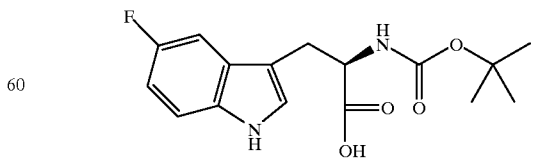

The title compound (1.26 g) was obtained from the intermediate from the previous step (1.72 g) as in Example 47 Step B.

Step C:

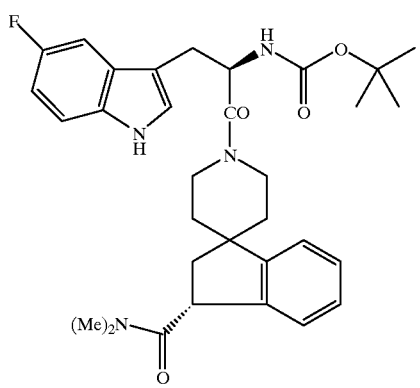

The title compound (110 mg) was prepared from the intermediate from Example 10 Step A and the intermediate from the previous step (98 mg) as in Example 10 Step B.

Step D:

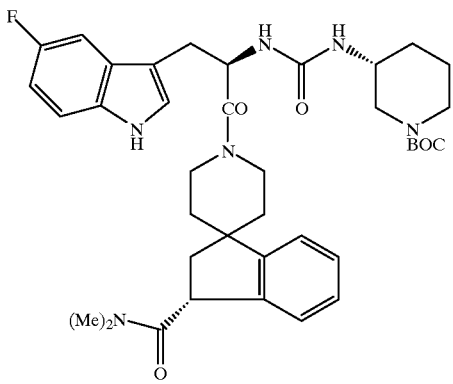

The intermediate from the previous step (110 mg) was deprotected with ethyl acetate/HCl and the residue was treated with the isocyanate from Example 10 Step F to give the title compound (45 mg).

Step E:

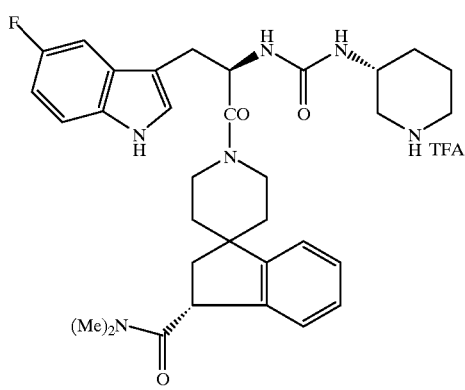

The title compound (12 mg) was prepared from the intermediate above (15 mg) as in Example 10 Step H. Key ¹H NMR (δ, CD$_3$OD, 400 MHz, mix of rotamers): 5.10 (m, 2/3 H), 5.05 (m, 1/2 H), 3.28 (s, 3/3 H), 3.20 (s, 6/3H), 3.02 (s, 3/3 H), 2.99 (s, 6/3 H), 1.00 (m, 2/3 H), 0.00 (m, 2/3 H). MS-FAB: 589.3 (M+1).

EXAMPLE 49

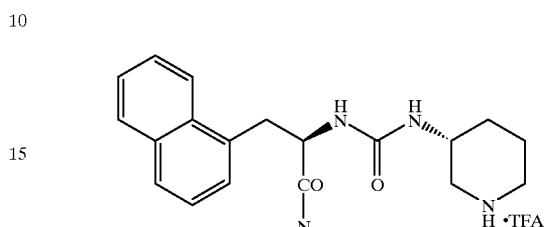

Step A:

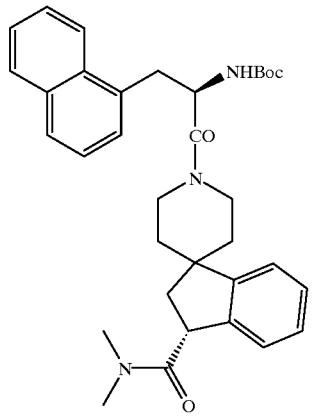

To a solution of the (1-napthyl)glycine (537 mg, 1 eq), the hydrochloride salt from Example 10 Step A (1 eq.), HOBT (1 eq.), and N-methyl morpholine (2 eq.) in dichloromethane cooled to 0° C. was added EDCI (2.0 eq.). The reaction mixture was allowed to warm to r.t. while stirring overnight. The mixture was concentrated and chromatographed (SiO$_2$, 4:1 CH$_2$Cl$_2$/acetone) to provide 370 mg of the title compound. ESI-MS calc. for C$_{34}$H$_{41}$N$_3$O$_4$ 555; Found 556 (M+H), 456. Key ¹HNMR: (CDCl$_3$; 400 MHz); 8.29 (d, 1 H), 6.68 (d, 1 H), 3.15 (s, 3 H), 3.00 (s, 3 H), 2.075 (d, 1 H), 1.49 (s, 9 H), 0.59 (d, 1 H).

Step B:

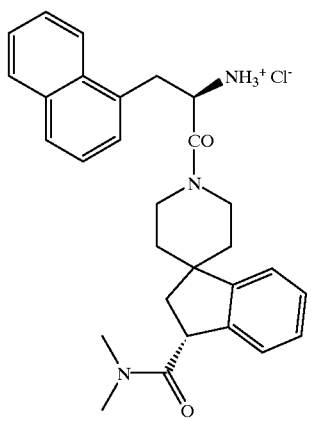

A solution of the N-Boc dipeptide from the previous step (370 mg, 0.68 mmol)) in ethyl acetate (8 mL) was cooled to 0° C. While stirring, HCl-EtOAc was added to the mixture (10 mL). The reaction was stirred for 20 minutes, until HPLC analysis indicated that the reaction was complete. The mixture was concentrated in vacuo to remove the ethyl acetate affording 302 mg of the title compound. ESI-MS calc. for $C_{29}H_{33}N_3O_2$ 455; Found 456 (M+H). Key $^1$HNMR: (CD$_3$OD; 400 MHz); 8.14 (d, 1 H), 6.61 (d, 1 H), 3.28 (d, 3 H), 2.99 (d, 3 H), 0.97 (dt, 1 H), 0.65 (dd, 1 H).

Step C:

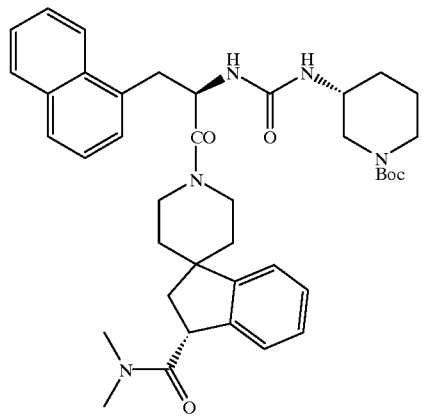

To a solution of the intermediate from above (100 mg, 0.210 mmol), NMM (2.0 eq) and dichloromethane (2.5 mL) was added the isocyanate from Example 10 Step F (1.2 eq). The mixture was stirred 16 hr, concentrated and the residue chromatographed (SiO$_2$, 4:1 CH$_2$Cl$_2$/acetone) to provide 76 mg of the title compound. ESI-MS calc. for $C_{40}H_{51}N_5O_5$ 681; Found 682 (M+H), 582, 456. Key $^1$HNMR: (CDCl$_3$; 500 MHz); 8.43 (d, 1H), 7.80–7.00 (m, 9H), 6.68 (d, 1H), 3.21–3.00 (m, 7H), 0.58 (d, 1H), −0.58 (dt, 1H; J=4 Hz).

Step D:

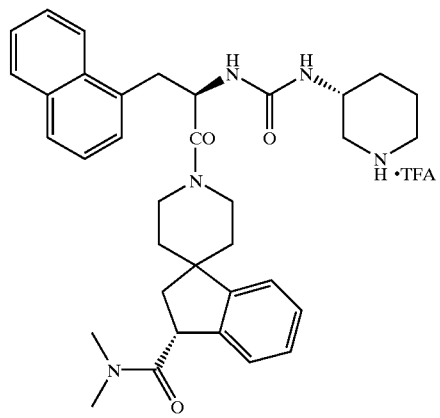

A solution of the intermediate from the previous step (76 mg, 0.11 mmol) in dichloromethane (3 mL) was treated with TFA (3 mL). The reaction was stirred for 20 minutes, until HPLC analysis indicated that the reaction was complete. The solvent was removed in vacuo and purified by MPLC (LH$_{20}$, methanol) affording 65 mg of the title compound. ESI-MS calc. for $C_{35}H_{43}N_5O_3$ 581; Found 582 (M+H). Key $^1$HNMR: (CDCl$_3$; 500 MHz); 8.26 (d, 1 H), 7.85–6.95 (m, 8 H), 6.68 (d, 1 H), 3.25–2.95 (m, 6 H), 0.64 (d, 1 H), −0.55 (dt, 1 H; J=4 Hz).

EXAMPLE 50

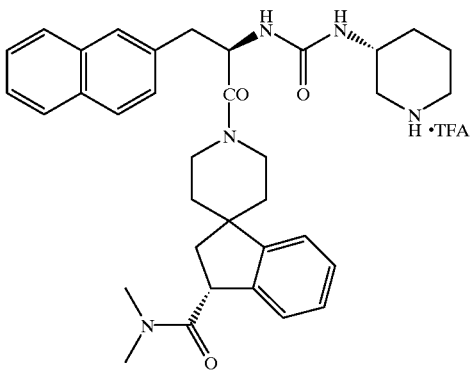

Step A:

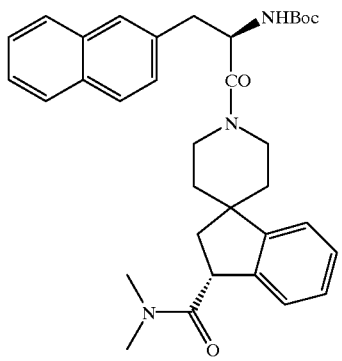

To a solution of the (2-napthyl)glycine (537 mg, 1.70 mmol), the N,N-dimethylcarboxamido spiroindane (1 eq.), HOBT (1 eq.), and N-methyl morpholine (2 eq.) in dichloromethane cooled to 0° C. was added EDC (2.0 eq.). The reaction mixture was allowed to warm to r.t. while stirring overnight. The mixture was concentrated and chromatographed (SiO$_2$, 4:1 CH$_2$Cl$_2$/acetone) to provide 650 mg of the title compound. ESI-MS calc. for C$_{34}$H$_{41}$N$_3$O$_4$ 555; Found 556 (M+H), 456. Key $^1$HNMR: (CDCl$_3$; 400 MHz); 7.90–6.80 (m, 11 H), 3.24–2.97 (m, 7 H), 2.12 (d, 1 H), 1.47–1.38 (m, 9 H), 0.93 (d, 1 H), –0.90 (d, 1 H).

Step B:

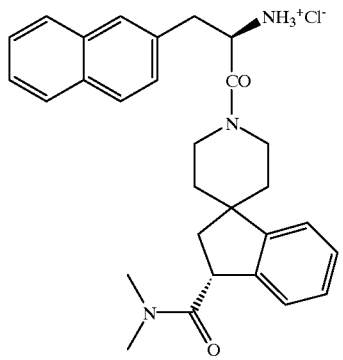

A solution of the N-Boc dipeptide from above (650 mg, 1.20 mmol)) in ethyl acetate (8 mL) was cooled to 0° C. While stirring, HCl-EtOAc was added to the mixture (10 mL). The reaction was stirred for 20 minutes, until HPLC analysis indicated that the reaction was complete. The mixture was concentrated in vacuo to remove the ethyl acetate affording 518 mg of the title compound.

Step C:

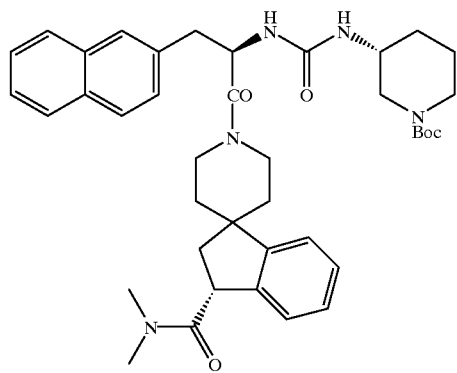

To a solution of the above intermediate (100 mg, 0.210 mmol), NMM (2.0 eq) and dichloromethane (2.5 mL) was added the isocyanate from Example 10 Step F (1.2 eq). The mixture was stirred 16 hr, concentrated and the residue chromatographed (SiO$_2$, 4:1 CH$_2$Cl$_2$/acetone) to provide 84 mg of the title compound. ESI-MS calc. for C$_{40}$H$_{51}$N$_5$O$_5$ 681; Found 682 (M+H), 582, 456. Key $^1$HNMR: (CDCl$_3$; 500 MHz); 7.86–6.87 (m, 10 H), 3.28–3.00 (m, 7 H), 0.99 (d, 1 H), –0.05 (dt, 1 H; J=4 Hz).

Step D:

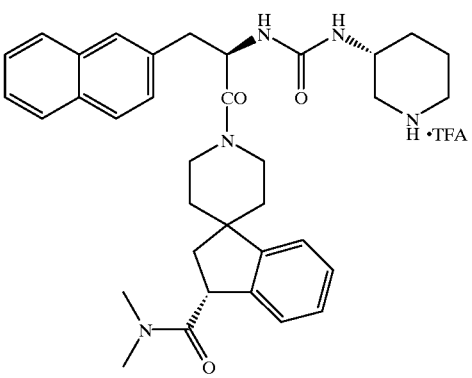

A solution of the intermediate from the previous step (84 mg, 0.13 mmol) in dichloromethane (3 mL) was treated with TFA (3 mL). The reaction was stirred for 20 minutes, until HPLC analysis indicated that the reaction was complete. The solvent was removed in vacuo and purified by MPLC (LH$_{20}$, methanol) affording 65 mg of the title compound. ESI-MS calc. for C$_{35}$H$_{43}$N$_5$O$_3$ 581; Found 582 (M+H). Selected $^1$HNMR: (CDCl$_3$; 500 MHz); 7.89–6.90 (m, 10 H), 3.30–2.96 (m, 7 H), 1.03 (d, 1 H), –0.04 (dt, 1 H; J=4 Hz).

EXAMPLE 51

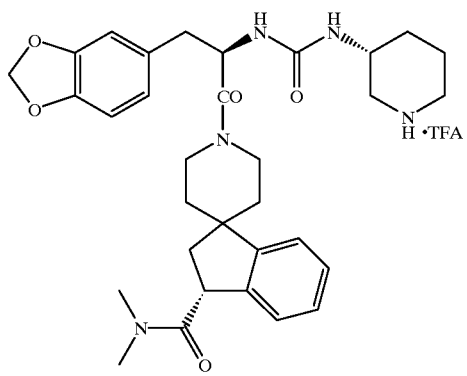

Step A:

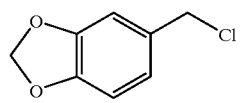

To a stirred solution of piperonyl alcohol (10 g, 65.7 mmol) in carbon tetrachloride (60 mL) triphenylphosphine (23 g, 85.4 mmol) is added in one portion. The reaction mixture is refluxed 2 hr then cooled while stirring. 70 mL of pentane is added to the mixture and stirred an additional 5 min. then filtered. The organic layer is then concentrated and chromatographed (SiO$_2$, hexane) to provide 1.4 g of the title compound. $^1$HNMR: (CDCl$_3$; 300 MHz) 6.88–6.72 (m, 3H), 5.95 (s, 2H), 4.51 (s, 2H).

Step B:

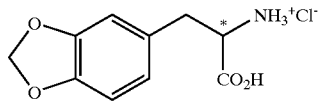

To a stirred solution of piperonyl chloride (1.4 g, 8.2 mmol), tetrabutylammonium chloride (0.1 eq), potassium carbonate (3.0 eq) in dry acetonitrile (15 mL) was added (N-diphenylmethylene) glycine ethyl ester (1.0 eq) and the mixture refluxed 16 hr. Remove the solvent in vacuo and stir in 1 N HCl (15 mL) 1 hr and then extract with ether. Add conc. HCl (25 mL) and reflux 16 hr. Extract with ether and remove the solvent in vacuo to provide 1.02 g of the title compound. ESI-MS calc. for $C_{10}H_{11}NO_4$:HCl 209; Found 210 (M+H). $^1$HNMR: ($CD_3OD$; 500 MHz); 5.94 (s, 2H), 4.20 (t, 1H), 3.61 (dd, 2H).

Step C:

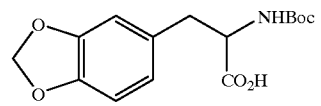

To a stirred solution of the intermediate from above (1.023 g, 4.15 mmol) in 1 N NaOH/dioxane (35 ml) at 0° C. was added di-t-butoxydicarbonate (0.95 g, 4.57 mmol). The reaction mixture was allowed to warm to r.t. overnight. The mixture was concentrated, acidified to pH 1 and extracted with EtOAc (3×50 mL), dried over $MgSO_4$ and the solvent removed in vacuo to afford 900 mg of the title compound. $^1$HNMR: ($CDCl_3$; 500 MHz) 5.87 (s, 2 H), 4.27 (t, 1 H), 2.94 (dd, 2 H), 1.38 (s, 9 H).

Step D:

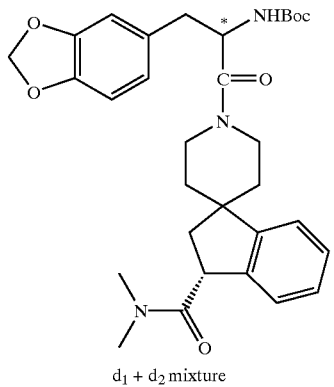

d$_1$ + d$_2$ mixture

To a solution of the amino acid from above (7.16 mg, 2.44 mmol), the hydrochloride salt from Example 10 Step A (1 eq.), HOBT (1 eq.), and N-methyl morpholine (2 eq.) in dichloromethane cooled to 0° C. was added EDC (2.0 eq.). The reaction mixture was allowed to warm to r.t. while stirring 16 hr. The mixture was concentrated and chromatographed ($SiO_2$, 4:1 $CH_2Cl_2$/acetone) to provide 500 mg of the title compound. ESI-MS calc. for $C_{31}H_{39}N_3O_6$ 549; Found 550 (M+H), 450. Key $^1$HNMR: ($CDCl_3$; 500 MHz); 6.00–5.90 (m, 2 H), 3.16 (dd 6 H), 1.45 (s, 9 H), 0.91 (dt, 1 H).

Step E:

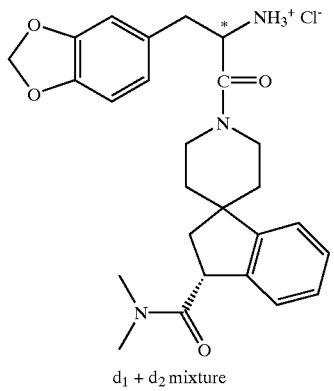

d$_1$ + d$_2$ mixture

A solution of the N-Boc dipeptide from above (480 mg, 0.87 mmol)) in ethyl acetate (4 mL) was cooled to 0° C. While stirring, HCl-EtOAc was added to the mixture (5 mL). The reaction was stirred for 20 minutes, until HPLC analysis indicated that the reaction was complete. The mixture was concentrated in vacuo to remove the ethyl acetate affording 440 mg of the title compound. ESI-MS calc. for $C_{26}H_{31}N_3O_{64}$ 449; Found 450 (M+H), 316, 259.

Step F:

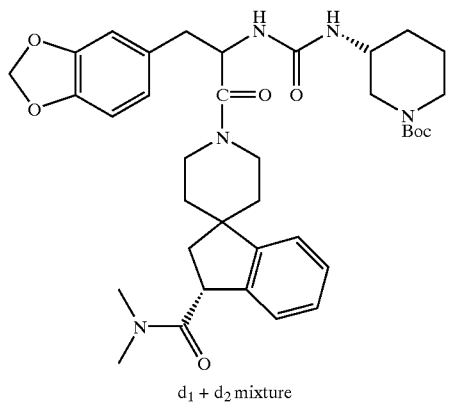

d$_1$ + d$_2$ mixture

To a solution of the compound prepared in the previous step (130 mg, 0.268 mmol), NMM (1.5 eq) and dichloromethane (2.5 mL) was added the isocyanate from Example 10 Step F (1.5 eq). The mixture was stirred 16 hr, concentrated and the residue chromatographed ($SiO_2$, 4:1 $CH_2Cl_2$/acetone) to provide 120 mg of the title compound. ESI-MS calc. for $C_{37}H_{49}N_5O_7$ 675; Found 676 (M+H).

Step G:

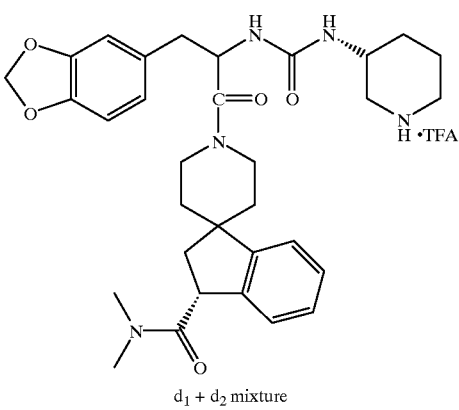

d$_1$ + d$_2$ mixture

103

A solution of the compound from the previous step (120 mg, 0.18 mmol) in dichloromethane (3 mL) was treated with TFA (3 mL). The reaction was stirred for 20 minutes, until HPLC analysis indicated that the reaction was complete. The solvent was removed in vacuo and purified by MPLC (LH$_{20}$, methanol) affording 80 mg of the title compound. ESI-MS calc. for C$_{32}$H$_{41}$N$_5$O$_5$ 575; Found 576 (M+H), 289. Selected $^1$HNMR: (CDCl$_3$; 500 MHz); 7.24–6.65 (m, 7 H), 5.89 (s 2 H), 3.30–3.01 (m, 7 H), 0.71 (dt, 1 H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

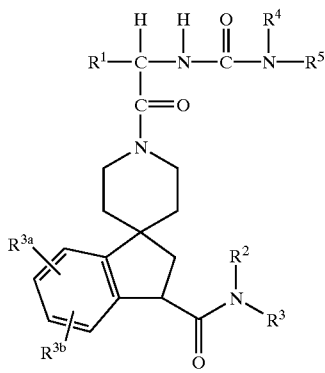

wherein:

R$^1$ is selected from the group consisting of:

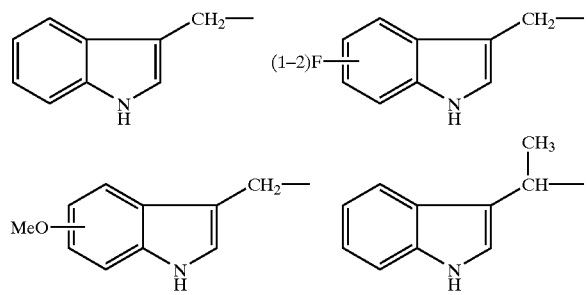

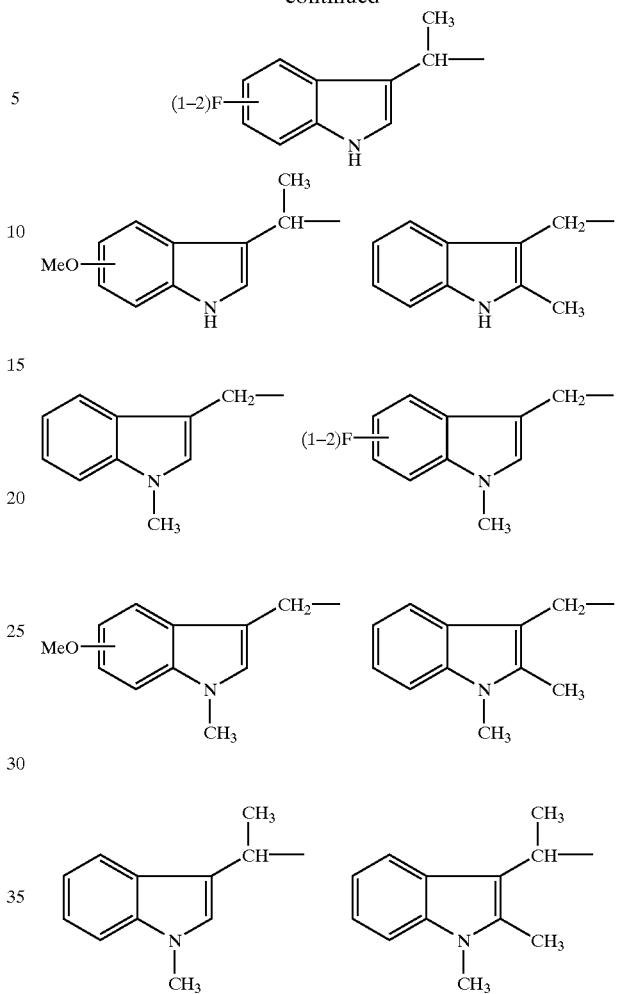

or their regioisomers where not specified;

R$^2$ and R$^3$ are independently selected from the group consisting of: hydrogen, —C$_1$–C$_6$ alkyl, —C$_3$–C$_7$ cycloalkyl, and —CH$_2$-phenyl, wherein the alkyl, the cycloalkyl and the phenyl are unsubstituted or substituted with —OR$^{2a}$, —C(O)OR$^{2a}$, —C(O)N(R$^{2a}$)(R$^{2b}$), halogen, —C$_1$–C$_4$ alkyl, —S(O)$_n$R$^{2a}$, —NHS(O)$_2$(R$^{2a}$), and wherein R$^2$ and R$^2$ are optionally joined to form a C$_4$–C$_5$ cyclic ring being selected from the group consisting of pyrrolidine, piperidine, piperazine, morpholine, and thiomorpholine;

R$^{2a}$ and R$^{2b}$ are independently selected from: hydrogen and C$_1$–C$_6$ alkyl;

R$^{3a}$ and R$^{3b}$ are independently selected from: hydrogen, —C$_1$–C$_6$ alkyl, —OR$^2$, and halogen;

R$^4$ is selected from: hydrogen, C$_1$–C$_6$ alkyl, and substituted C$_1$–C$_6$ alkyl where the substituents on alkyl are selected from halo, —OR$^2$, phenyl, C$_1$–$_6$ alkoxycarbonyl, —S(O)$_n$R$^{2a}$, and —NHS(O)$_n$(R$^{2a}$);

R$^5$ is selected from:
hydrogen,
C$_1$–C$_6$ alkyl,
substituted C$_1$–C$_6$ alkyl where the substituents on alkyl are selected from halo, —OR$^2$, phenyl, —S(O)$_n$R$^{2a}$, —NHS(O)$_n$(R$^{2a}$),

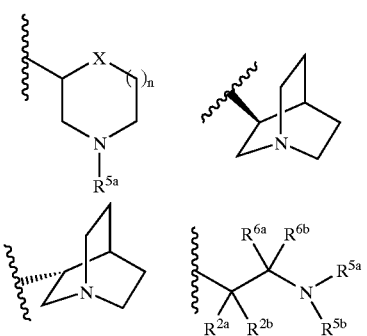

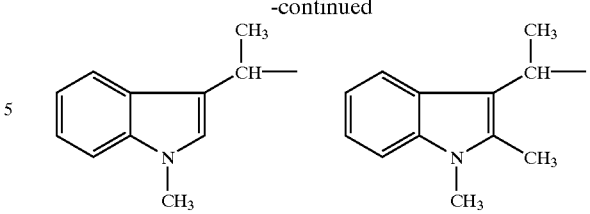

R$^{5a}$ and R$^{5b}$ are independently selected from: hydrogen, C$_{1-6}$ alkyl, or substituted C$_1$–C$_6$ alkyl where the substituents are selected from: halo, —OR$^2$, C$_1$–C$_6$ alkoxy, phenyl, C$_1$–C$_6$ alkoxycarbonyl, —S(O)$_n$R$^{2a}$, —NHS(O)$_n$(R$^{2a}$);

R$^{6a}$ and R$^{6b}$ are independently selected from: hydrogen, C$_1$–C$_6$ alkyl, or trifluoromethyl;

X is selected from —CH$_2$—, —O— and —S—;

n is independently 0, 1 or 2;

and pharmaceutically acceptable salts and individual diastereomers thereof.

2. The compound of claim 1 wherein:

R$^1$ is selected from the group consisting of:

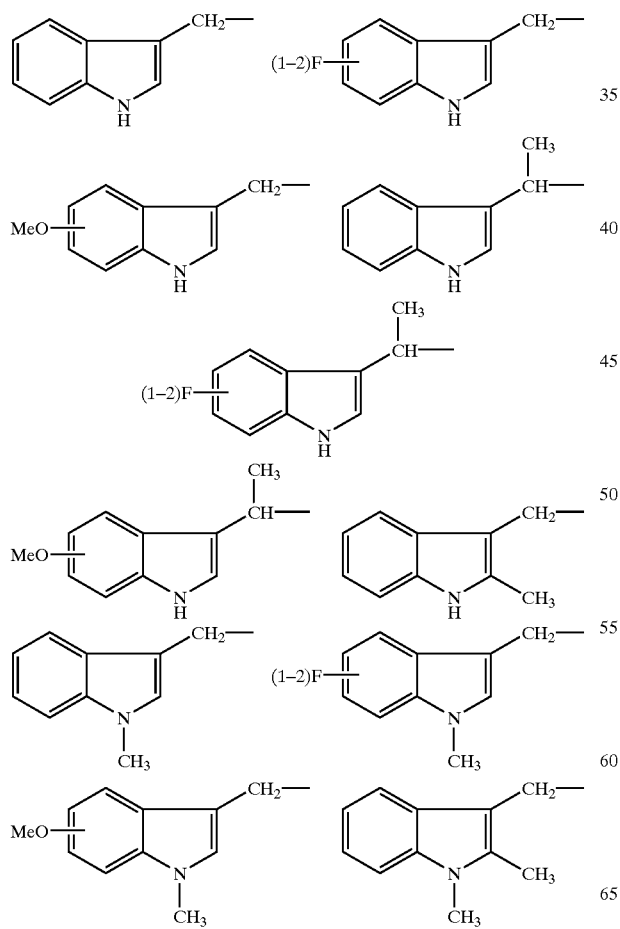

or their regioisomers where not specified;

R$^2$ and R$^3$ are independently selected from the group consisting of: hydrogen, —C$_1$–C$_6$ alkyl, —C$_3$–C$_7$ cycloalkyl, and —CH$_2$-phenyl, wherein the alkyl, the cycloalkyl and the phenyl are unsubstituted or substituted with —OR$^{2a}$, —C(O)OR$^{2a}$, —C(O)N(R$^{2a}$)(R$^{2b}$), halogen, —C$_1$–C$_4$ alkyl, —S(O)$_n$R$^{2a}$, —NHS(O)$_2$(R$^{2a}$), and wherein R$^2$ and R$^2$ are optionally joined to form a C$_4$–C$_5$ cyclic ring being selected from the group consisting of pyrrolidine, piperidine, piperazine, and morpholine;

R$^{2a}$ and R$^{2b}$ are independently selected from: hydrogen and C$_1$–C$_4$ alkyl;

R$^{3a}$ and R$^{3b}$ are independently selected from: hydrogen, —C$_1$–C$_6$ alkyl, —OR$^2$, and halogen;

R$^4$ is selected from: hydrogen, C$_1$–C$_6$ alkyl, and substituted C$_1$–C$_6$ alkyl where the substituents on alkyl are selected from halo, hydroxy, and —S(O)$_n$R$^{2a}$;

R$^5$ is selected from:

hydrogen,

C$_1$–C$_6$ alkyl, substituted C$_1$–C$_6$ alkyl where the substituents on alkyl are selected from halo, hydroxy, phenyl, —S(O)$_n$R$^{2a}$, —NHS(O)$_n$(R$^{2a}$),

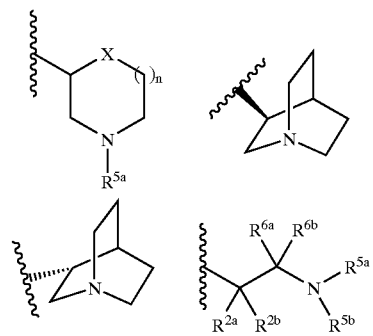

R$^{5a}$ and R$^{5b}$ are independently selected from: hydrogen, C$_1$–C$_6$ alkyl, or substituted C$_1$–C$_6$ alkyl where the substituents are selected from: halo, hydroxy, C$_1$–C$_6$ alkoxy, phenyl, —S(O)$_n$R$^{2a}$, and —NHS(O)$_n$(R$^{2a}$);

R$^{6a}$ and R$^{6b}$ are independently selected from: hydrogen, C$_1$–C$_6$ alkyl, or trifluoromethyl;

X is selected from —CH$_2$—, —O— and —S—;

n is independently 0, 1 or 2;

and pharmaceutically acceptable salts and individual diastereomers thereof.

3. The compound of claim 1 wherein:
R¹ is selected from the group consisting of:

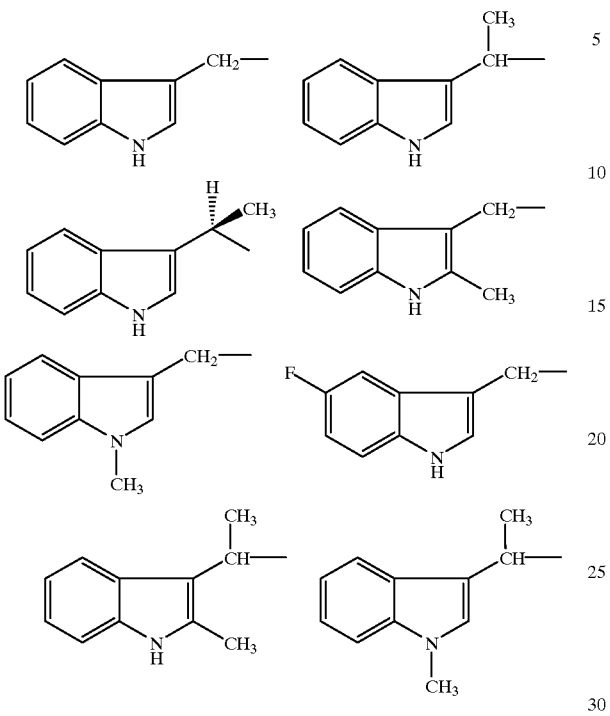

R² and R³ are independently selected from the group consisting of:
  hydrogen and —C₁–C₆ alkyl, wherein the alkyl is unsubstituted or substituted with —OR²ᵃ, —S(O)₂R²ᵃ, and —NHS(O)₂CH₃, and wherein R² and R² are optionally joined to form a 5- or 6-membered ring selected from the group consisting of pyrrolidine, piperidine, piperazine, and morpholine;
R²ᵃ and R²ᵇ are independently selected from: hydrogen and C₁–C₄ alkyl;
R³ᵃ and R³ᵇ are independently selected from: hydrogen and halogen;
R⁴ is selected from: hydrogen or C₁–C₄ alkyl;
R⁵ is selected from:
  hydrogen,
  C₁–C₆ alkyl,
  substituted C₁–C₆ alkyl where the substituents on alkyl are selected from halo, hydroxy, phenyl, —NHS(O)₂(R²ᵃ),

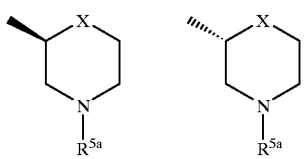

and

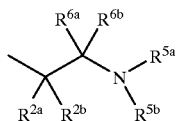

R⁵ᵃ and R⁵ᵇ are independently selected from:
  hydrogen, C₁–C₆ alkyl, or substituted C₁–C₆ alkyl where the substituents are selected from: halo, hydroxy, C₁–C₆ alkoxy, phenyl, —S(O)ₙR²ᵃ, and —NHS(O)ₙ(R²ᵃ);
R⁶ᵃ and R⁶ᵇ are independently selected from: hydrogen, C₁–C₆ alkyl, or trifluoromethyl;
X is selected from —CH₂— and —O—;
n is 0, 1 or 2;
and pharmaceutically acceptable salts and individual diastereomers thereof.

4. A compound which is selected from the group consisting of:

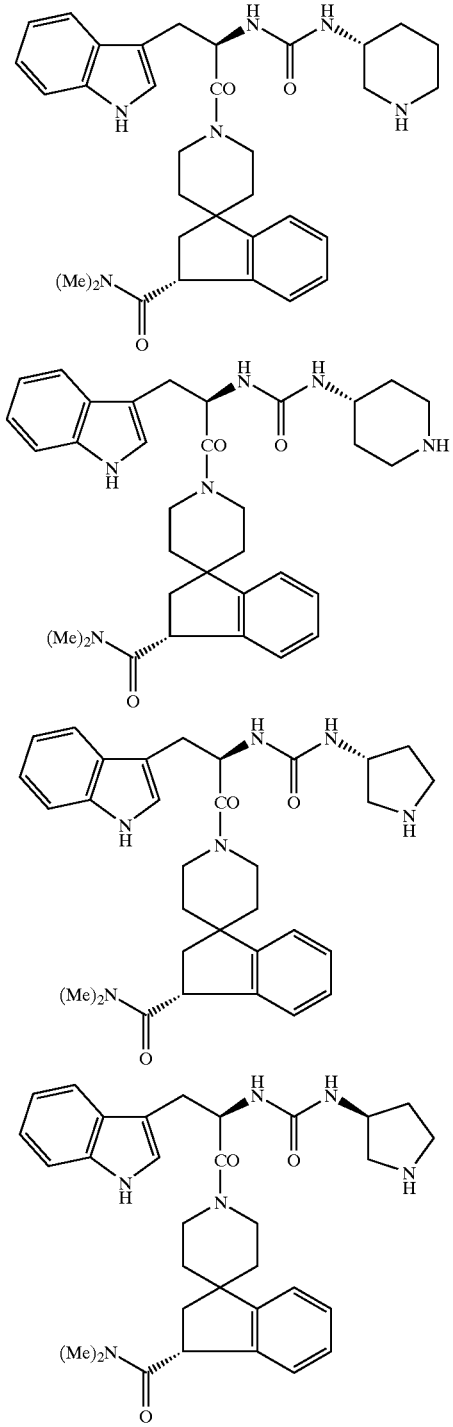

-continued
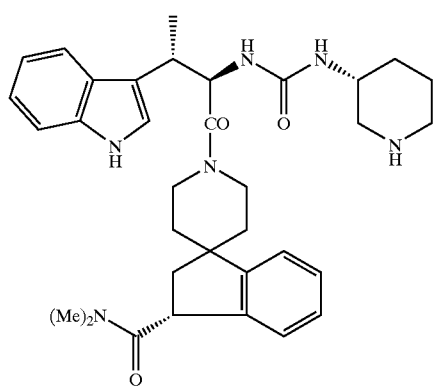
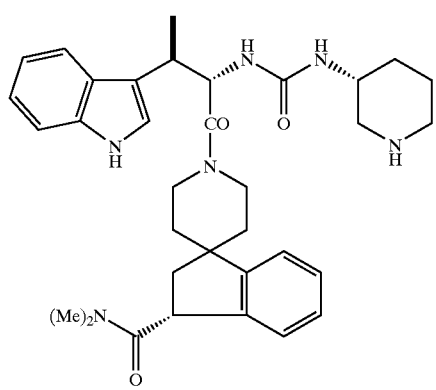
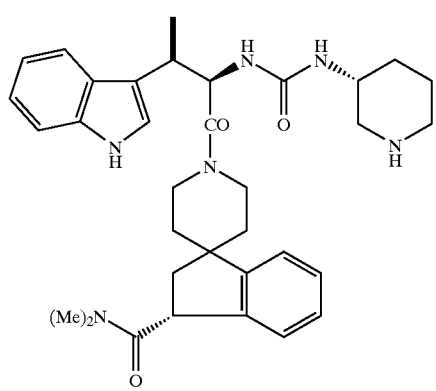
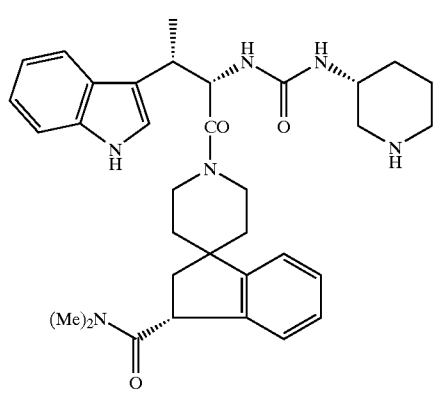
-continued
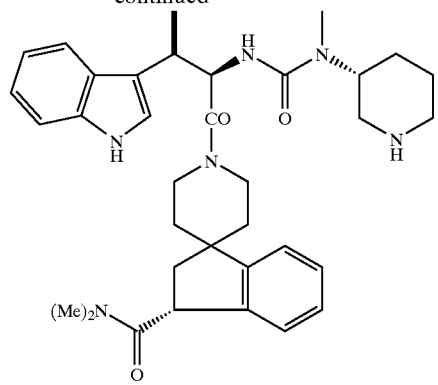
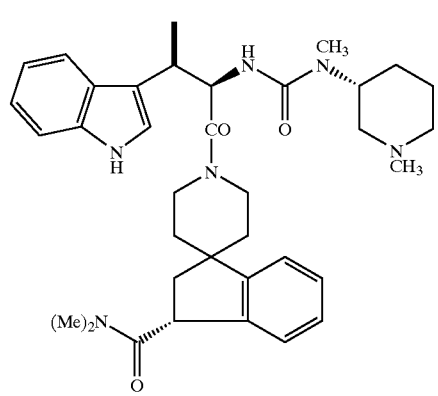
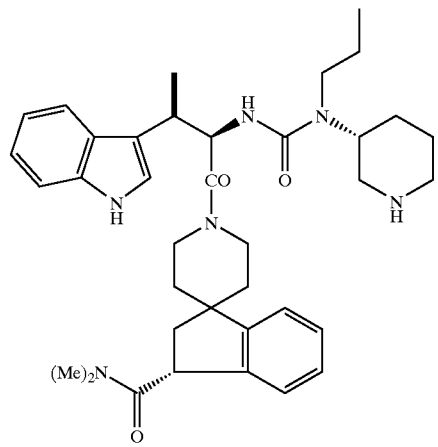
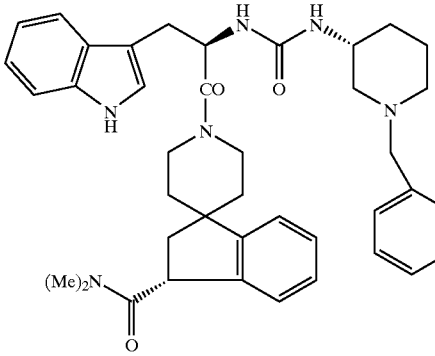

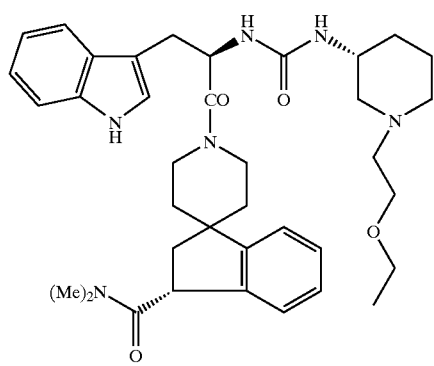
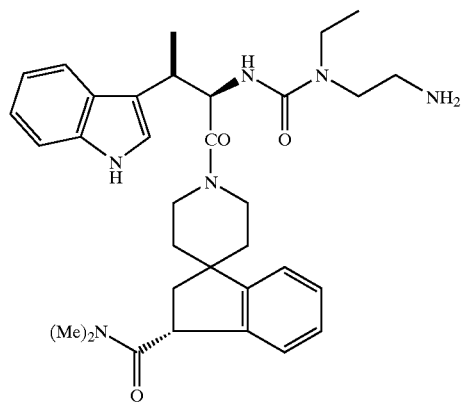
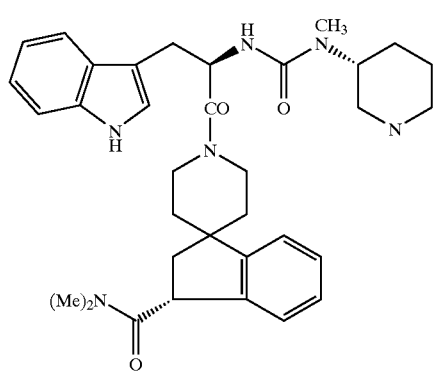
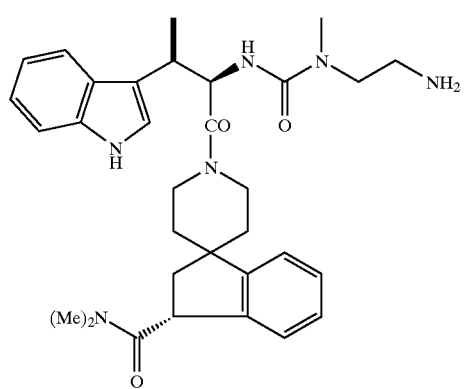
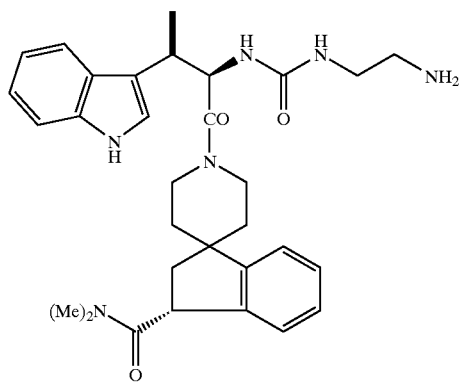
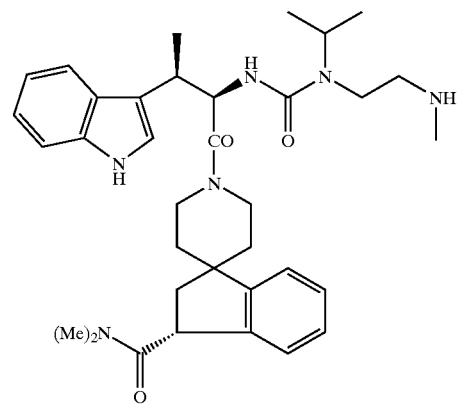
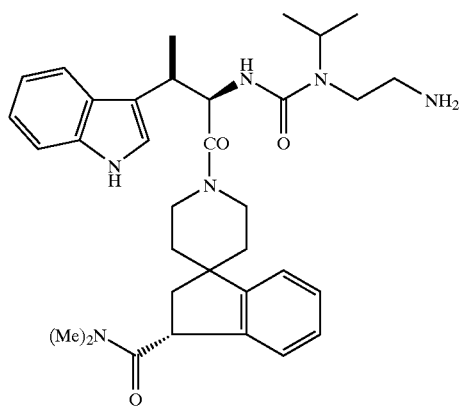
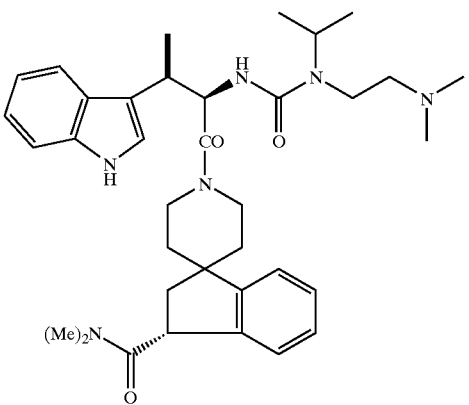

113
-continued
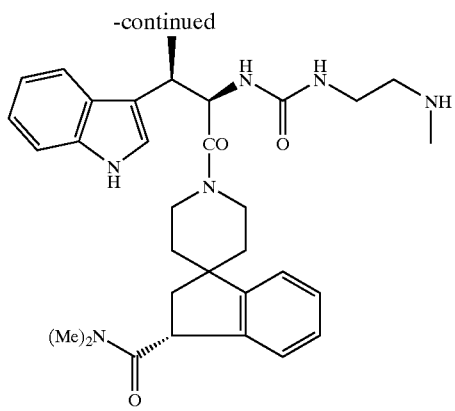
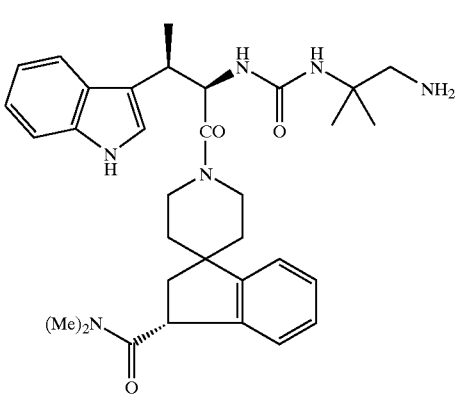
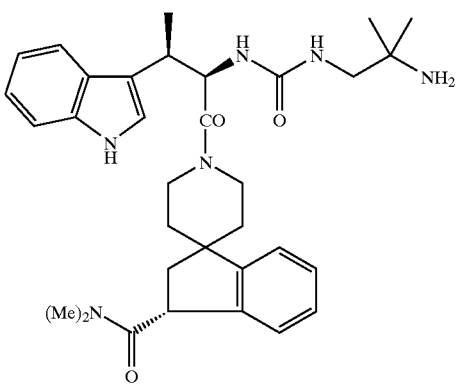
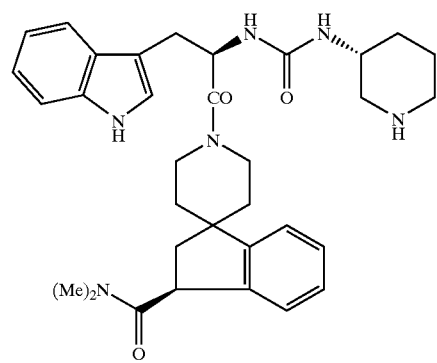
114
-continued
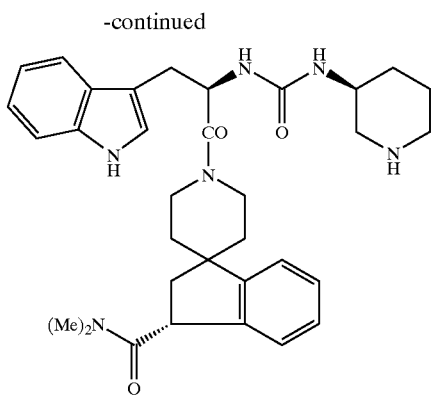
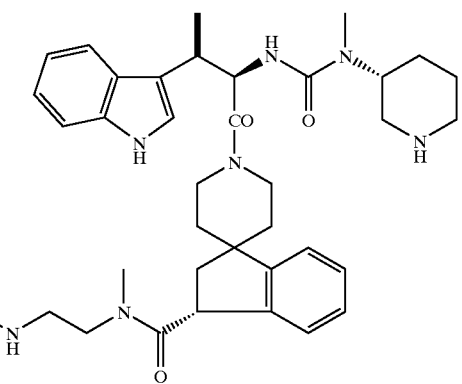
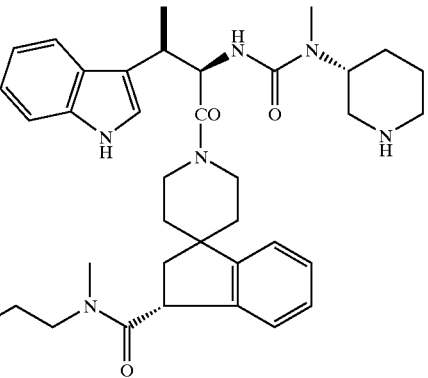
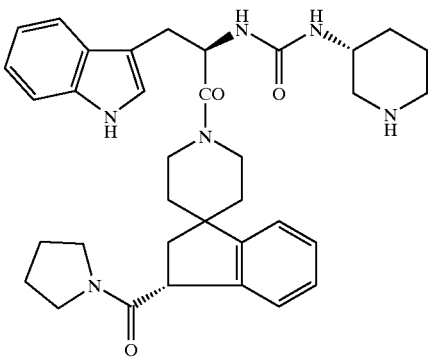

115
-continued
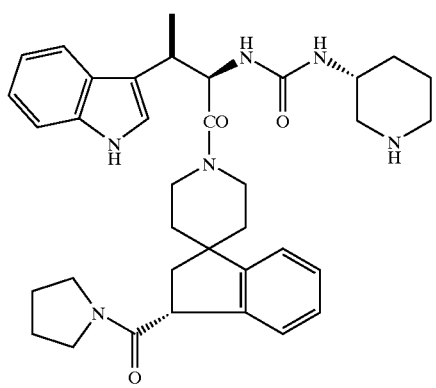
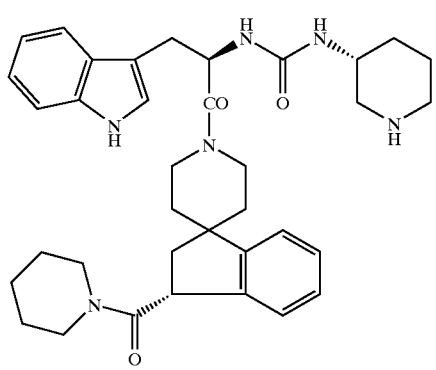
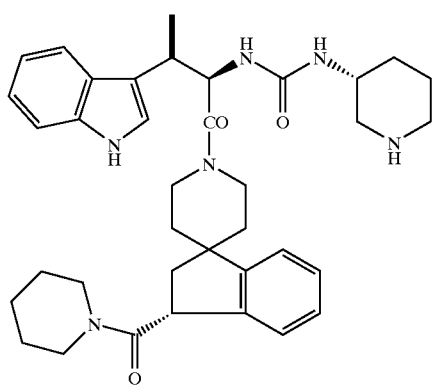
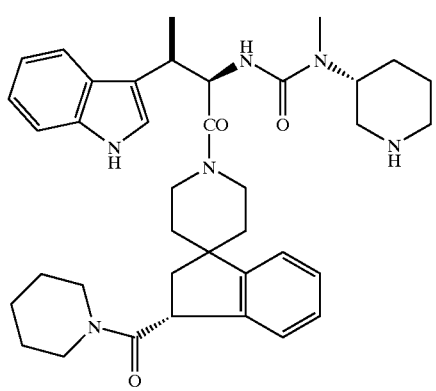
116
-continued
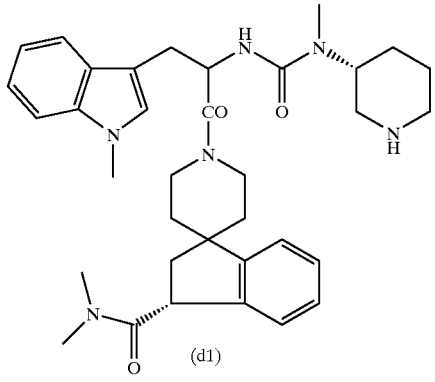
(d1)
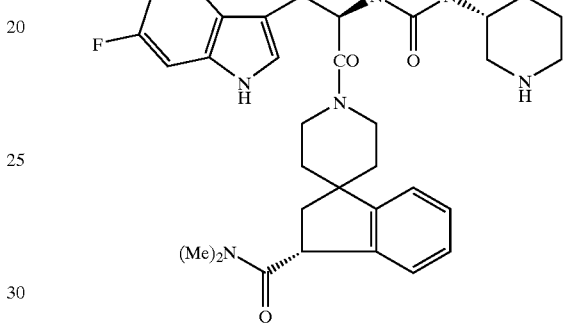
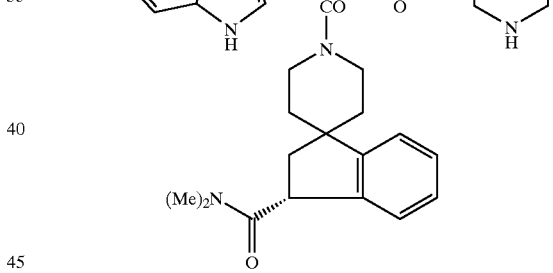
and pharmaceutically acceptable salts and individual diastereomers thereof where not otherwise specified.
5. A compound which is selected from the group consisting of:
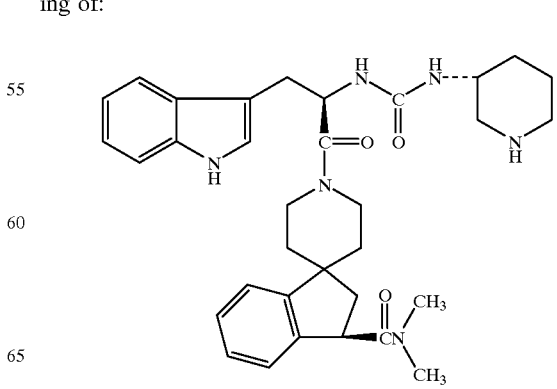

117
-continued
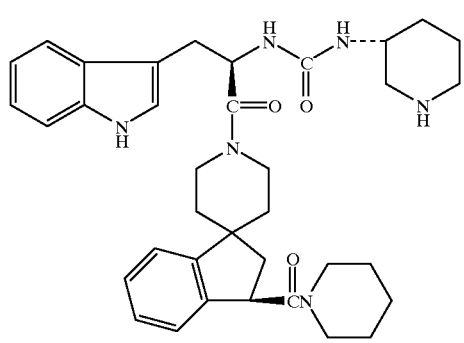
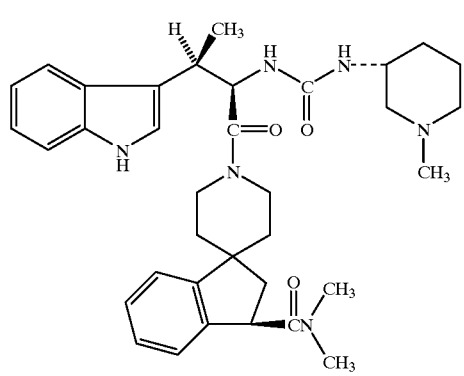
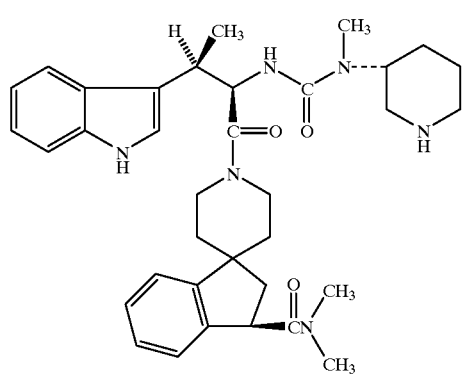
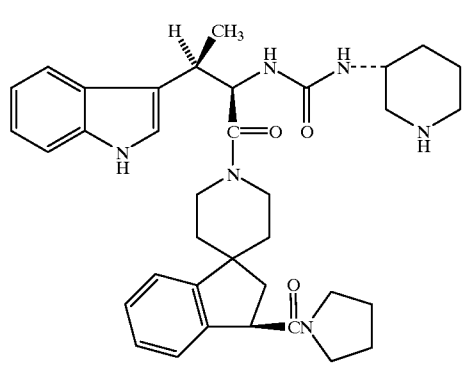
118
-continued
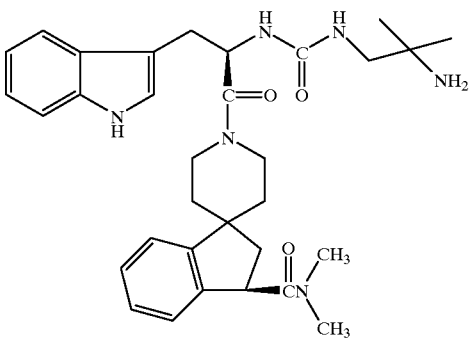
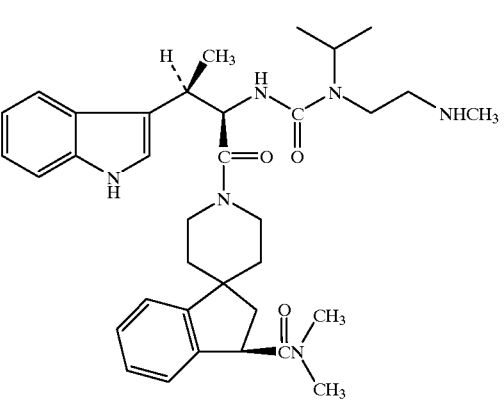
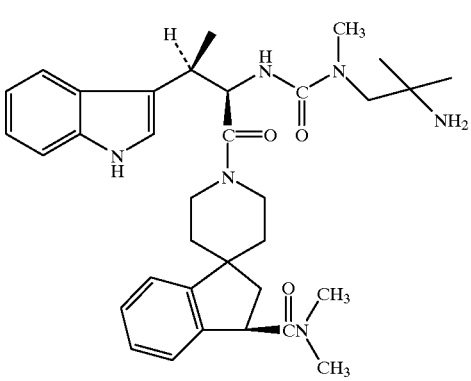
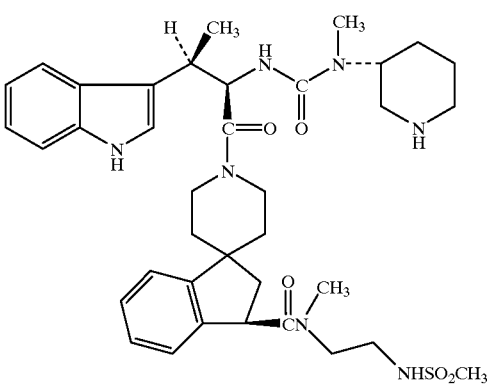

-continued

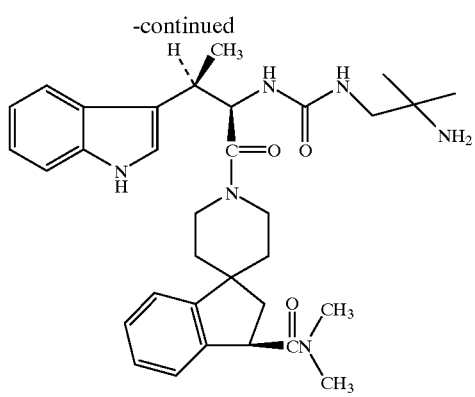

and their pharmaceutically acceptable salts and individual diastereomers thereof where not otherwise specified.

6. A pharmaceutical composition which comprises an inert carrier and a compound of claim 1.

7. A method for the treatment of a disease or a condition which is benefited by the anabolic effects of enhanced growth hormone levels that comprises administering to a patient in need thereof an effective amount a compound of claim 1.

* * * * *